US011974552B2

(12) United States Patent
Imam et al.

(10) Patent No.: US 11,974,552 B2
(45) Date of Patent: May 7, 2024

(54) TRANSGENIC C57BL6-BTBR MOUSE WITH A HUMANIZED MHC II GENE THAT EXPRESSES GAD65

(71) Applicant: The University of Toledo, Toledo, OH (US)

(72) Inventors: Shahnawaz Imam, Toledo, OH (US); Maria Alfonso-Jaume, Toledo, OH (US); Juan Carlos Jaume, Toledo, OH (US)

(73) Assignee: The University of Toledo, Toledo, OH (US)

( * ) Notice: Subject to any disclaimer, the term of this patent is extended or adjusted under 35 U.S.C. 154(b) by 320 days.

(21) Appl. No.: 16/530,452

(22) Filed: Aug. 2, 2019

(65) Prior Publication Data
US 2020/0037586 A1 Feb. 6, 2020

Related U.S. Application Data

(60) Provisional application No. 62/713,827, filed on Aug. 2, 2018.

(51) Int. Cl.
*A01K 67/027* (2024.01)
*A01K 67/0275* (2024.01)
*A61K 49/00* (2006.01)

(52) U.S. Cl.
CPC ...... *A01K 67/0275* (2013.01); *A61K 49/0008* (2013.01); *A01K 2217/05* (2013.01); *A01K 2227/105* (2013.01); *A01K 2267/0362* (2013.01)

(58) Field of Classification Search
None
See application file for complete search history.

(56) References Cited

U.S. PATENT DOCUMENTS 8,293,500 B2 * 10/2012 Wiley ............... A61P 13/12
435/70.1
2012/0321648 A1 * 12/2012 Hutton ............... A61P 31/04
424/184.1

OTHER PUBLICATIONS

Hutchings (Eur. J. Immunol. 1992, vol. 22, p. 1913-1918).*
Boyton (International Immunology, 1998, vol. 10, No. 12, p. 1765-1776.*
Wicker et al., "Naturally Processed T cell Epitopes from Human Glutamic Acid Decarboxylase Identified Using Mice Transgenic for the Type I Diabetes-associated Human MHC Class II Allele, DRB1*0401," J. Clin. Invest. 98:2597-603 (Dec. 1996).*
Wikipedia description of GAD, 2021.*
Ranheim (Arterioscler Thromb Vasc Biol. 1997, vol. 17, p. 3286-3293).*
Nabozny, J. Exp. Med., 1996, vol. 183, p. 27-37.*
Cheng (European J. Immunogenetics, 1996, vol. 23, p. 15-20).*
Wikipedia definition of HLA-DQ8, 2023.*
IPD-IMGT/HLA Allele Query Tool description of and DQB1*0302, 2023.*
IPD-IMGT/HLA Allele Query Tool description of DQA1*0301, 2023.*
Jackson Lab description of C57BL/6, 2023.*
Jackson Lab description of BTBR mice, 2023.*

* cited by examiner

*Primary Examiner* — Michael C Wilson
(74) *Attorney, Agent, or Firm* — MacMillan, Sobanski & Todd, LLC

(57) ABSTRACT

A mouse model that develops type 1 diabetes spontaneously and used thereof are described. In some embodiments, the mouse model expresses a combination of HLA-DQ8 and GAD65 in a C57BL/6-BTBR congenic background, where the GAD65 is expressed under the rat insulin promoter.

11 Claims, 47 Drawing Sheets
(43 of 47 Drawing Sheet(s) Filed in Color)
Specification includes a Sequence Listing.

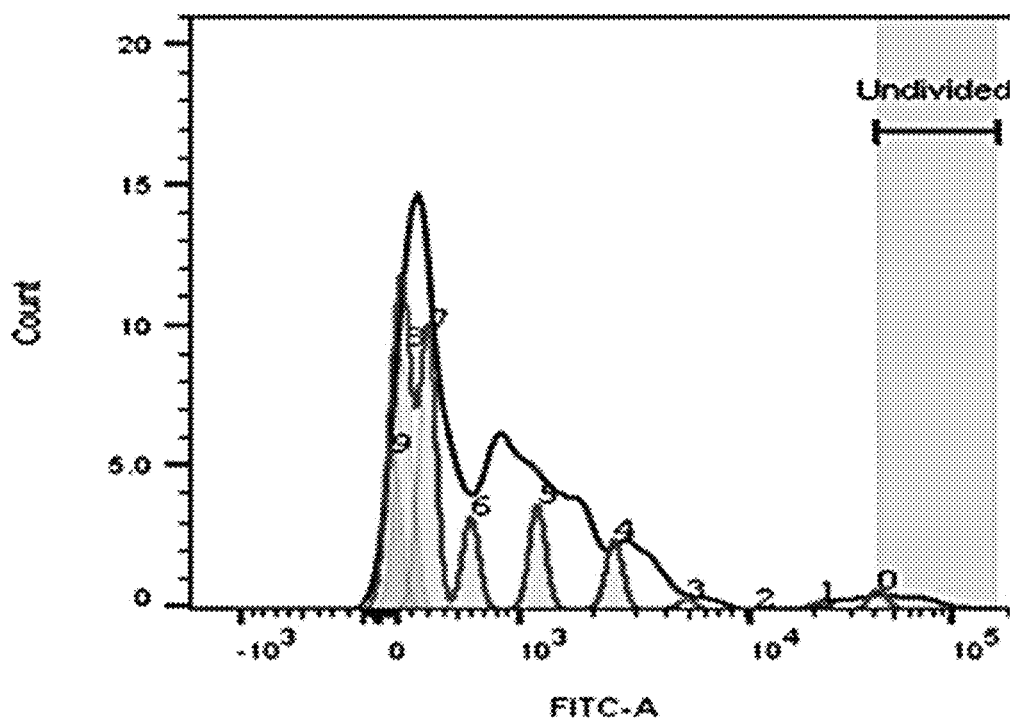
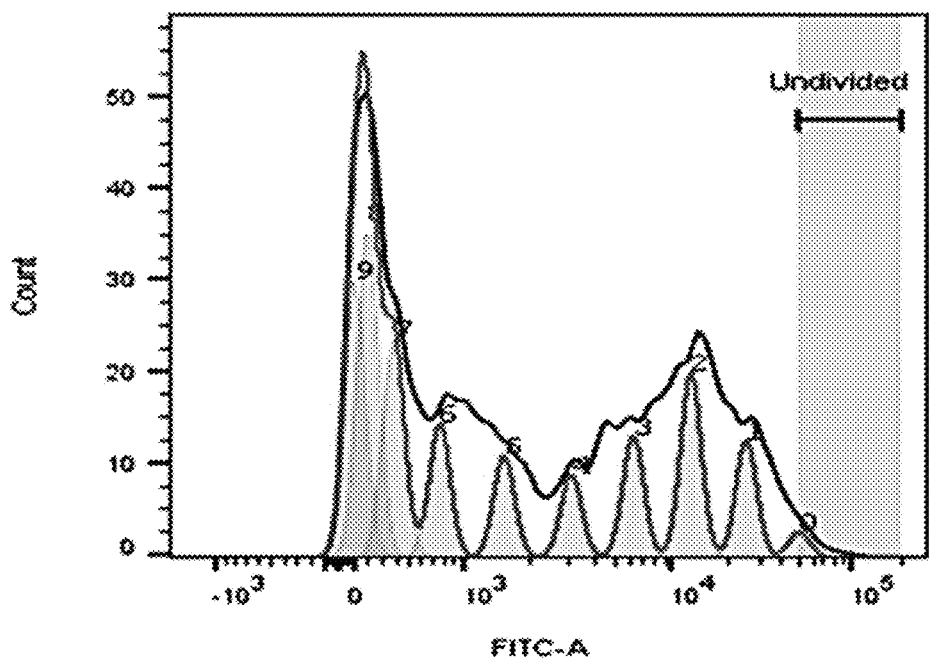
FIG. 6C

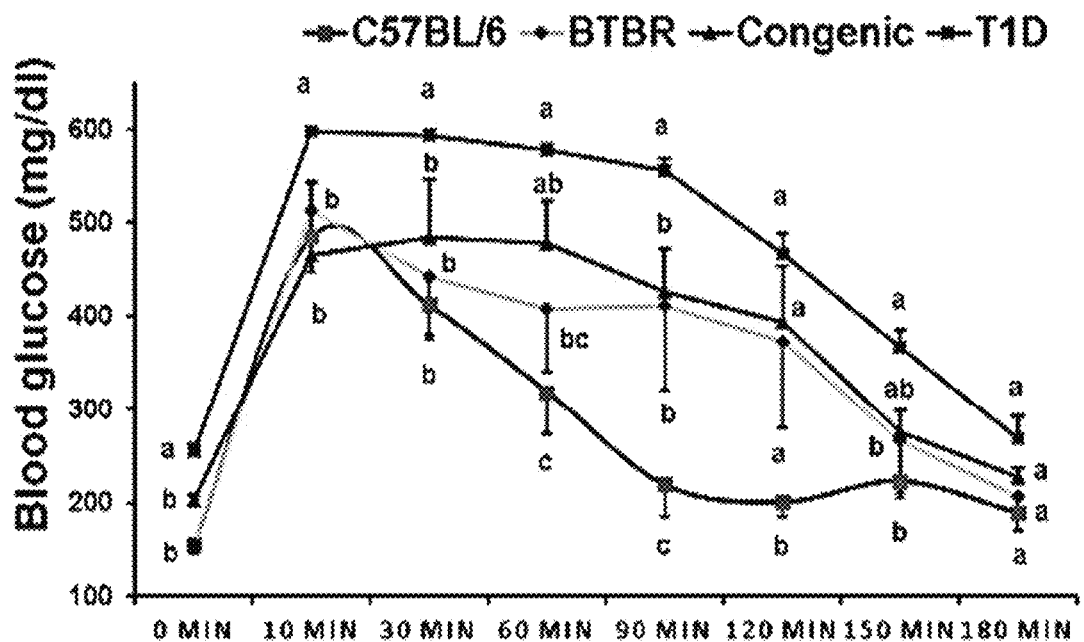
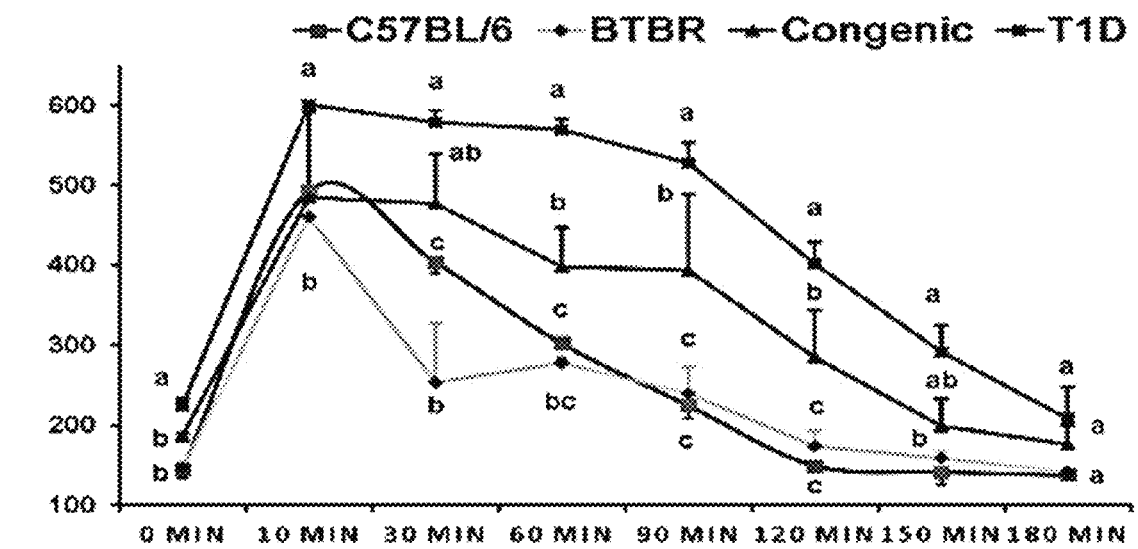
FIG. 6H

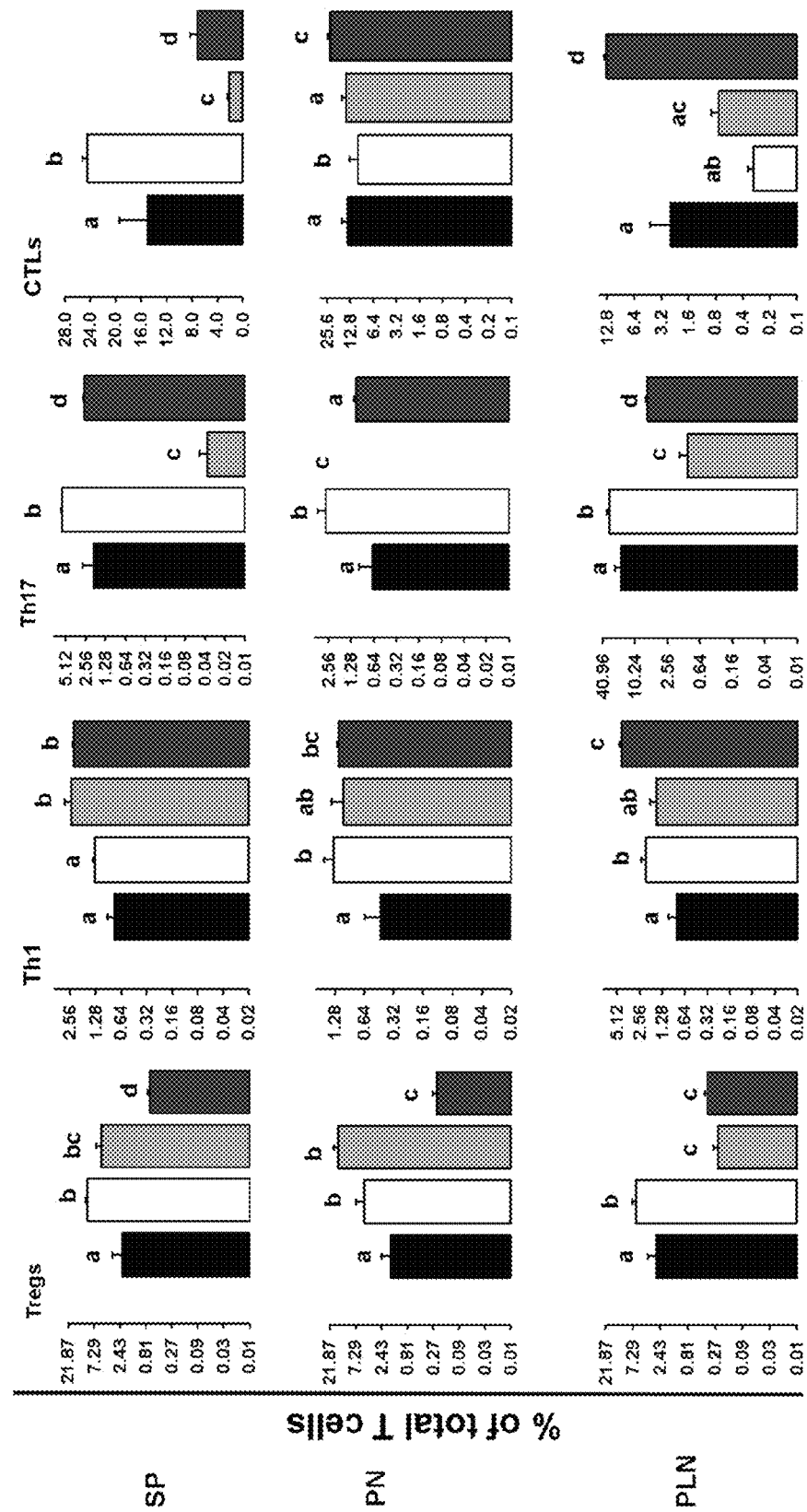

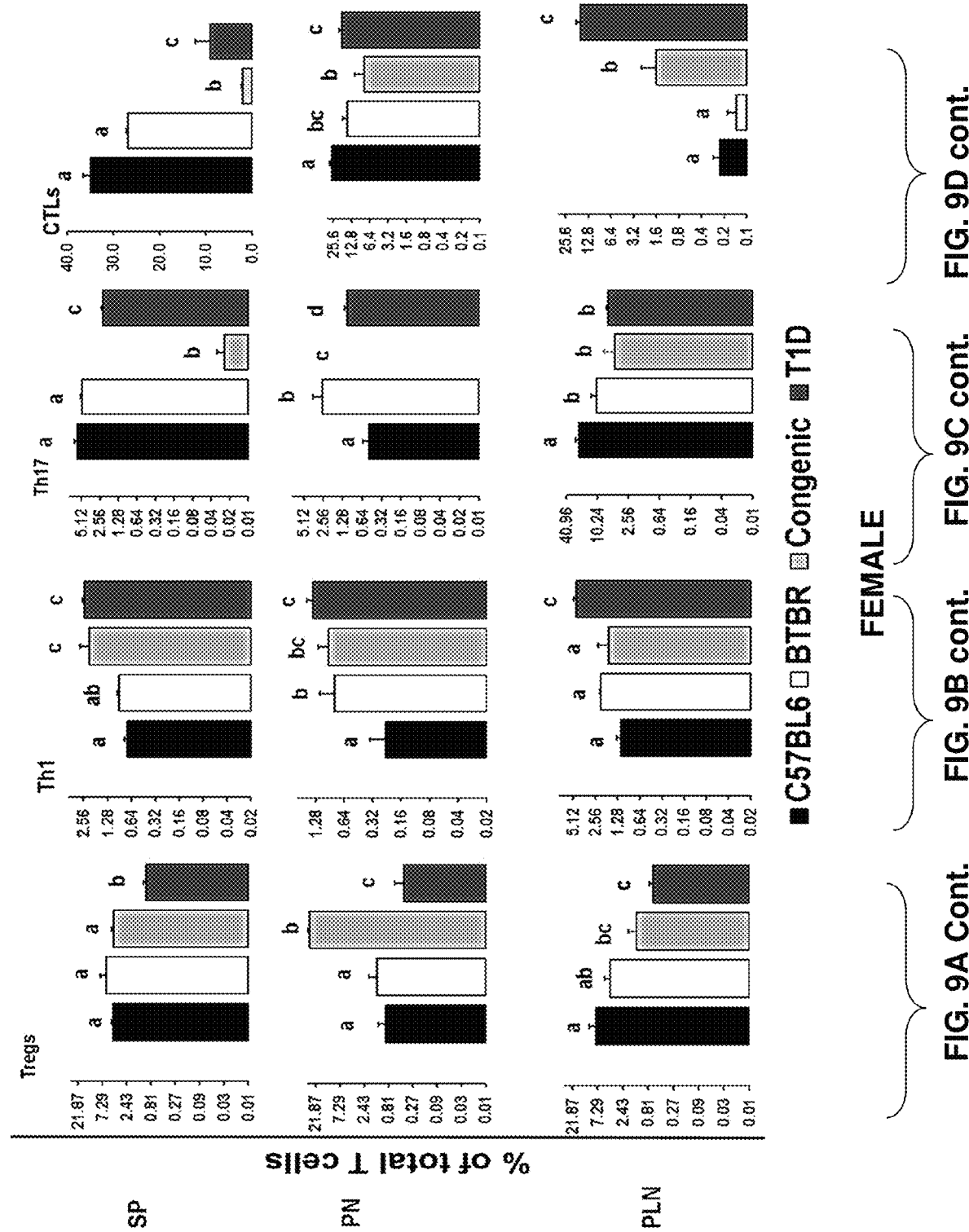

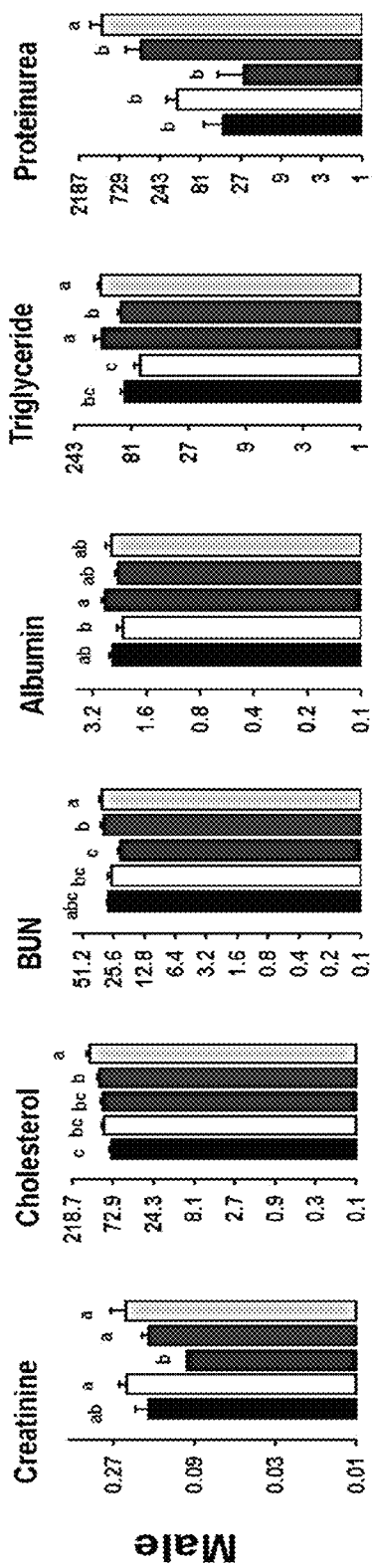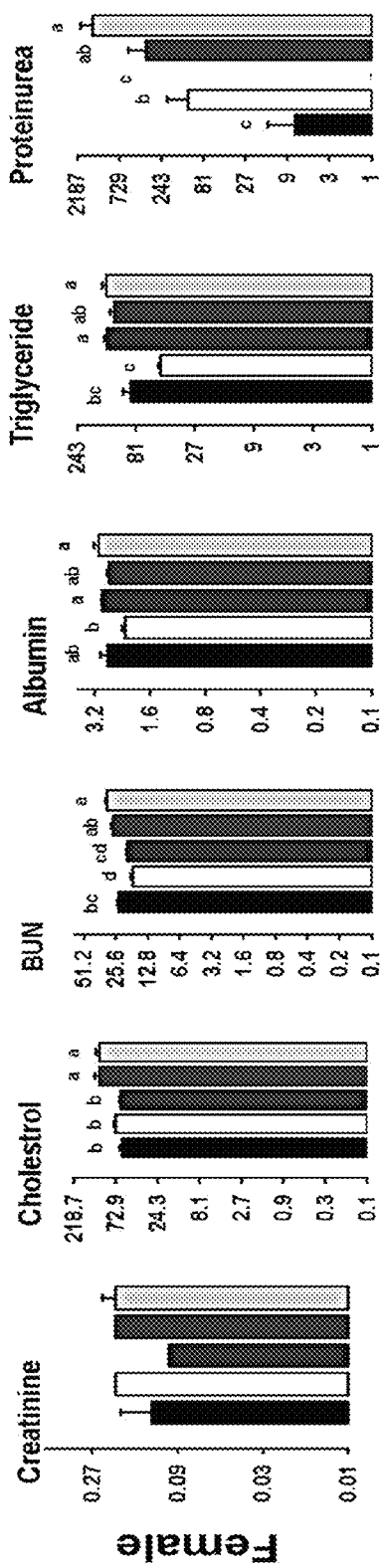
FIG. 10A FIG. 10B FIG. 10C FIG. 10D FIG.10E FIG. 10F

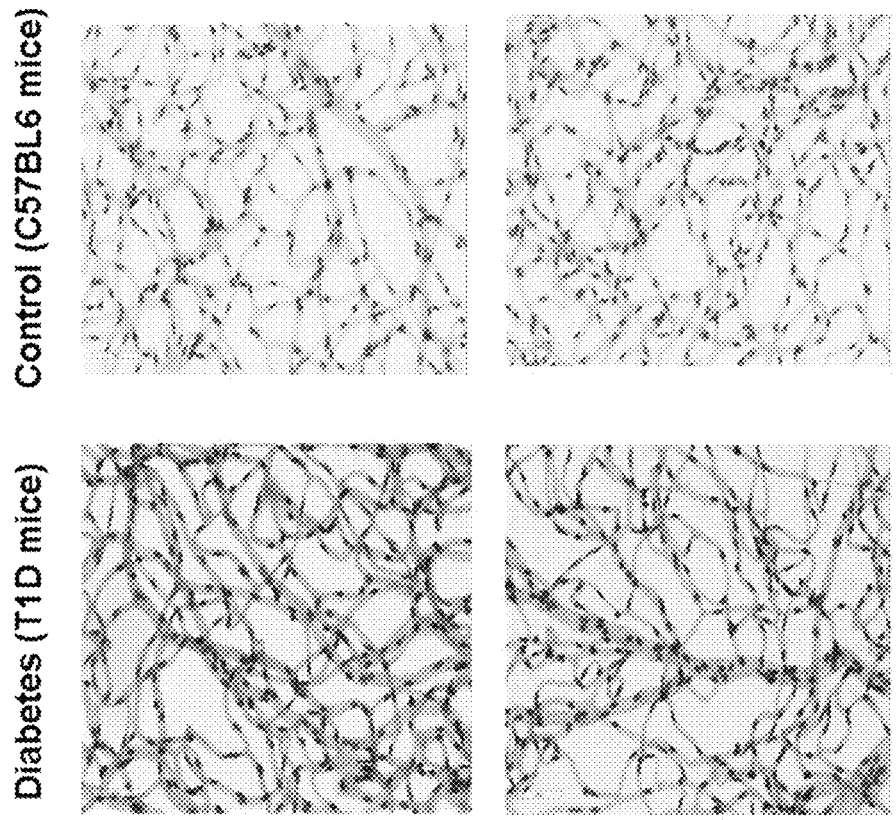
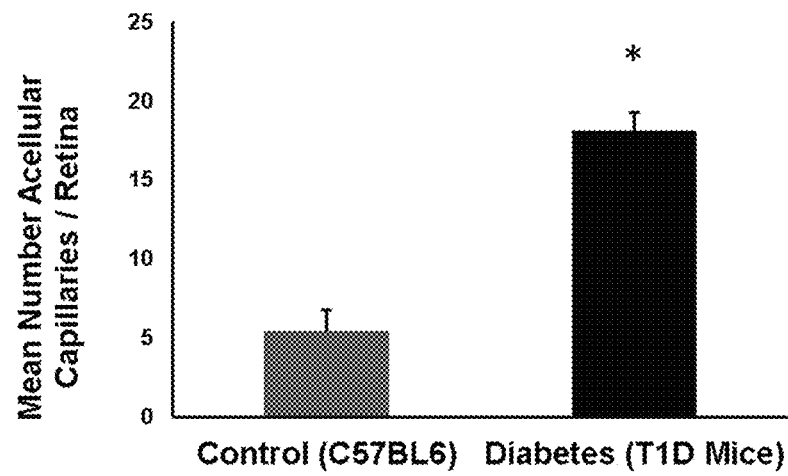
FIG. 14

TRANSGENIC C57BL6-BTBR MOUSE WITH A HUMANIZED MHC II GENE THAT EXPRESSES GAD65

RELATED APPLICATIONS

This application claims priority to United States Provisional Application No. 62/713,827 filed under 35 U.S.C. § 111(b) on Aug. 2, 2018, the disclosure of which is incorporated herein by reference in its entirety.

STATEMENT REGARDING FEDERALLY SPONSORED RESEARCH

This invention was made with no government support. The government has no rights in this invention.

SEQUENCE LISTING

The instant application contains a Sequence Listing which has been submitted via EFS-web and is hereby incorporated by reference in its entirety. The ASCII copy, created on Aug. 2, 2019 is named 420_60291_SEQ_LIST_D2015-60.txt, and is 20,485 bytes in size.

BACKGROUND OF THE INVENTION

An animal model of type 1 diabetes (T1D) would be highly desirable for studies of molecular mechanisms of disease and for development of antigen specific immunetherapies applicable to man. Current models do not fully reflect the human condition. Gene knock out models cannot be used to really mimic the total physiopathology of diabetes complications. Thus, there is a need in the art for an animal model of human T1D. It would be especially advantageous to develop an animal model of human T1D that exhibits the complications of diabetes.

SUMMARY

Provided is a mouse model that develops type 1 diabetes spontaneously. In certain embodiments, the mouse model expresses a diabetes-susceptibility human MHC class II molecule in antigen presenting cells, and expresses a human β-cell autoantigen in mouse β-cells. In particular embodiments, the diabetes-susceptibility human MHC class II molecule comprises DQ8. In particular embodiments, the human β-cell autoantigen comprises human Glutamic Acid Decarboxylase (hGAD65). In particular embodiments, the mouse model expresses hGAD65 from the rat insulin promoter (RIP). In particular embodiments, the mouse model has compromised β-cell neogenesis and/or proliferation. In particular embodiments, the mouse model comprises a C57BL/6-BTBR background.

In certain embodiments, the mouse model develops diabetic retinopathy. In certain embodiments, the mouse model develops diabetic nephropathy. In certain embodiments, the mouse model shows proliferation of acellular capillaries in the retina. In certain embodiments, the mouse model demonstrates focal segmental mesangial matrix increase and hyaline deposit in glomerular arterioles of the kidneys. In certain embodiments, the mouse model shows lymphocytic infiltration of islets of Langerhans in the pancreas.

Further provided is a mouse model expressing a combination of HLA-DQ8 and GAD65 with a C57BL/6-BTBR background. In certain embodiments, the mouse model expresses GAD65 from the rat insulin promoter (RIP). In certain embodiments, the mouse model develops diabetic retinopathy. In certain embodiments, the mouse model develops diabetic nephropathy. In certain embodiments, the mouse model shows proliferation of acellular capillaries in the retina. In certain embodiments, the mouse model demonstrates focal segmental mesangial matrix increase and hyaline deposit in arterioles of the kidneys. In certain embodiments, the mouse model shows lymphocytic infiltration of islets of Langerhans in the pancreas.

Further provided is a mouse model which expresses high levels of hGAD65 in β-cells and comprises endogenous mouse MHC-class II antigens replaced by a human HLA-DQ8 diabetes susceptibility locus, wherein the mouse model has a genetic background providing for compromised β-cell neogenesis and/or proliferation. In certain embodiments, the genetic background comprises a C57BL/6-BTBR background. In certain embodiments, the mouse model develops diabetic retinopathy. In certain embodiments, the mouse model develops diabetic nephropathy. In certain embodiments, the mouse model shows proliferation of acellular capillaries in the retina. In certain embodiments, the mouse model demonstrates focal segmental mesangial matrix increase and hyaline deposit in arterioles of the kidneys. In certain embodiments, the mouse model shows lymphocytic infiltration of islets of Langerhans in the pancreas.

Further provided is an animal model of type 1 diabetes comprising a transgenic animal in which primary human β-cell autoantigens are presented to effector cells in the context of human MHC-class II diabetes susceptibility genes, wherein the transgenic animal has a genetic background providing for compromised β-cell neogenesis and/or proliferation.

Further provided is a method for producing a mouse model that develops diabetes spontaneously, the method comprising backcrossing, intercrossing and incrossing HLA-DQA1*0301/DQB1*0302 (DQ8) transgenic, murine MHC-class II molecule-deficient (mII-) C57BL/6-BTBR mice, RIP7-hGAD65 transgenic C57BL/6-BTBR mice to produce transgenic mice; and selectively incrossing the mice based on a high fasting blood glucose to produce a mouse model that develops diabetes spontaneously.

In certain embodiments, the mice are selectively incrossed for a plurality of generations. In certain embodiments, the mice are selectively incrossed for at least 30 generations. In certain embodiments, the mice are selectively incrossed for at least 30 generations. In certain embodiments, the method further comprises weaning the mouse model after at least 45 days so as to delay onset of diabetes.

Further provided is a method of controlling onset of diabetes in a mouse model that develops diabetes spontaneously, the method comprising weaning the mouse model after at least 45 days in order to delay onset of diabetes in the mouse model.

Further provided is a kit comprising a first mouse model that develops type 1 diabetes spontaneously, and a second mouse model that develops type 1 diabetes spontaneously, wherein the first mouse model and the second mouse model are capable of breeding to produce a third mouse model that develops type 1 diabetes spontaneously.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A shows GTTs of diabetic (index case) and non-diabetic animals.

FIG. 1B shows frozen sections of pancreas of diabetic (index case) and non-diabetic animals stained with hematoxylin and eosin; GTTs of diabetic and non-diabetic animals by gender. Some diabetic animal glucoses did not return to baseline.

FIG. 6C: rGAD65 induced proliferation of CD4 and CD8 cells, pancreatic lymph nodes (PLN) were isolated from humanized T1D mice and were stimulated with GAD65 (4 µg/ml) for 4 days (n=4). The proliferation of cells were tracked using CFSE and analyzed by FLOWJO V10 Beta software using fix ratio, fix CV and fix background from the un-stimulated cells.

FIG. 6H: Glucose tolerance test (GTT) of C57BL6, BTBR, Congenic and T1D mice, significant differences were noted at various time points (n=8-22). Statistical significance was determined at p<0.05. Lowercase letters (a-d) identify significant differences among the groups.

FIG. 9A: Statistical differences (bar graphs) of Treg population are shown. Note that the Treg cells were significantly less in T1D mice groups and the difference became more significant closer to the pancreas (PPLN and PN) (n=8-32 per group). Statistical significance was determined at p<0.05. Lowercase letters (a-d) identify significant differences among the groups.

FIG. 9B: T helper type 1 (Th1) cell population (CD3+ CD4+IFNγ), (bar graphs) (n=8-32 per group). Note that the Th1 cells were significantly higher at PPLN of T1D mice whereas, no significant differences were recorded at PN and SP among the group, whereas at PN, CD3 count is almost 50-200 times higher than rest of the mice strains (data not shown). Statistical significance was determined at p<0.05. Lowercase letters (a-d) identify significant differences among the groups.

FIG. 9C: T helper 17 (Th17) population (CD3+CD4+IL17) (n=8-32 per group) are shown. Note: No significant difference were recorded among the Th17 cells of different mouse strains, however, the number of Th17 cells in T1D mice PN was (50-200) times higher, because CD3 count is almost 50-200 times higher than rest of the mice strains (data not shown). Statistical significance was determined at p<0.05. Lowercase letters (a-d) identify significant differences among the groups.

FIG. 9D: Antigen specific cytotoxic CD8 T cells (CTLs) (CD3+CD8+IFNγ). Statistical differences (bar graphs) of CTLs cells (n=8-32 per group) are shown. Note that CTLs cells were significantly higher closer to pancreas (PLN and PN) in T1D mice whereas; CTLs were significantly low in the SP of T1D mice as compared to C57BL/6 and BTBR mice strains. Note: CTLs were antigen specific to GAD65 and their presence nearer the pancreas testifies to the antigen specificity against pancreatic auto-antigen (s). Statistical significance was determined at p<0.05. Lowercase letters (a-d) identify significant differences among the groups.

FIG. 10A-10F: Serum profile at different time points showing biomarkers of progression of diabetes complications:

FIG. 10A: Serum creatinine was significantly higher in 27 week-old T1D mice.

FIG. 10B: Serum cholesterol was also significantly higher in 27 week-old T1D mice.

FIG. 10C: BUN was also higher in T1D mice.

FIG. 10D: Serum albumin revealed no significant differences among the different mouse strains.

FIG. 10E: Serum Triglyceride were significantly higher in congenic and 27-week-old T1D mice.

FIG. 10F: Proteinuria reflects the severity of kidney damage. Proteinuria was significantly high in T1D mice and significantly increased in 27 week-old T1D mice.

FIG. 14: Eye complications. Animals developed diabetic retinopathy. Six-month-old animals had a significant increase of acellular capillaries in the retina as compared to controls.

FIG. 15A: Compound action potentials in 32 optic nerves were measured in 16 C57BL/6 control mice and 16 T1D diabetic mice.

FIG. 15B: Measurement for optic nerves—Velocity for C57BL6 mice (Black bar) and T1D diabetic mice (white bar).

FIG. 15C: Measurement for optic nerves—Recovery of $2n^d$ action potential for C57BL/6 control mice and 16 T1D diabetic mice.

FIG. 15D: Compound action potentials in 32 sciatic nerves were measured in 16 C57BL/6 control mice and 16 T1D diabetic mice.

FIG. 15E: Measurement for sciatic nerves—Velocity (black) for C57BL6 mice (Black bar) and T1D diabetic mice (white bar).

FIG. 15F: Measurement for sciatic nerves—Recovery of $2n^d$ action potential for C57BL/6 control mice and 16 T1D diabetic mice.

FIG. 20C: Shows Spearman correlation of gut bacterial taxa with blood glucose levels.

FIG. 23A: Sequences (SEQ OD NOS: 1-4, respectively in order of appearance) showing PID: Percent identity of protein sequence. Measure of similarity and scale of confidence; and, COV: Coverage sequence

DETAILED DESCRIPTION

Figure 1A:
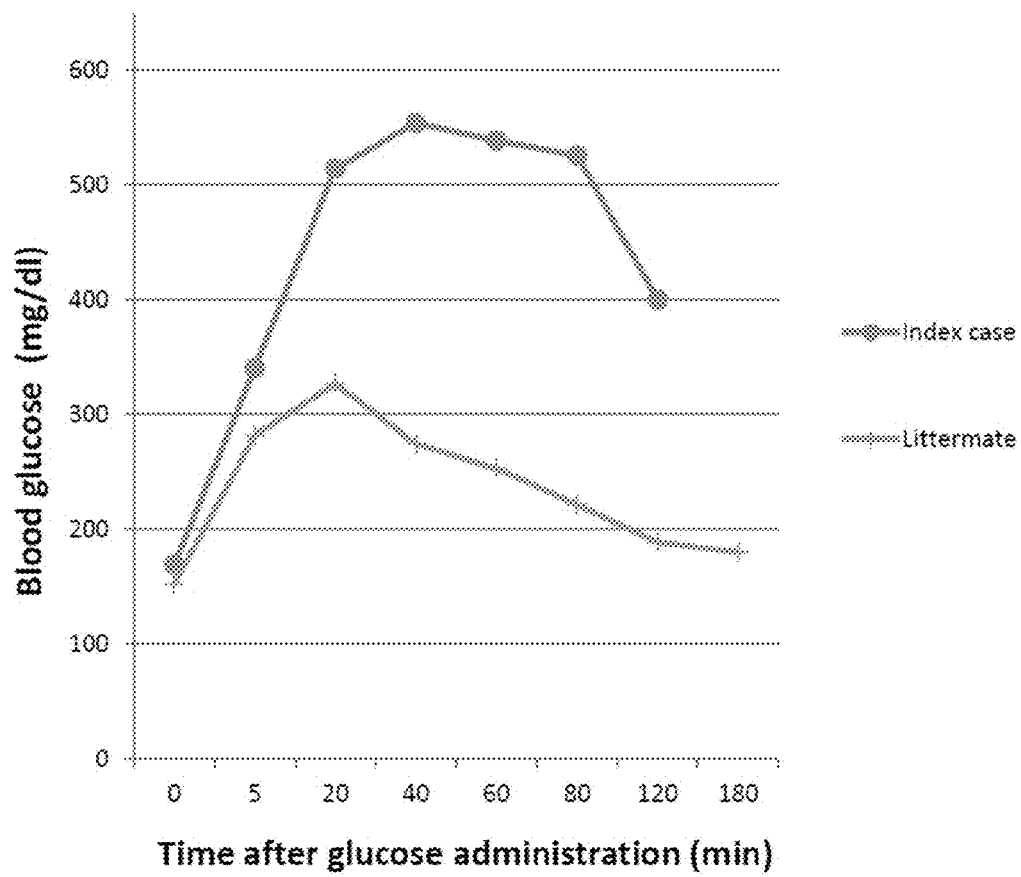
FIGS. 1A-1B: Histology (FIG. 1B) and glucose tolerance test (GTT) (FIG. 1A)

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Provided is a mouse model which develops type 1 diabetes spontaneously, and more closely resembles the human disease than known mouse models of diabetes because the mouse model exhibits the classic complications of diabetes. Moreover, the mouse model does not die from diabetes right away. Instead, the mouse model tends to survive for 6-12 months, which allows for the complications of diabetes to be studied using the mouse model. Notably, these complications (such as retinopathy, nephropathy, and neuropathy) are common to all types of diabetes, not just type 1. Thus, the mouse model described herein is useful for studying, and developing therapies for, T1D and diabetes complications. The mechanism by which the mouse model spontaneously develops T1D is not currently known.

In general, the mouse model described herein is characterized by three genetic features: (1) the mouse model expresses a major histocompatibility complex (MHC) class II molecule in antigen presenting cells; (2) the mouse model expresses a human β-cell autoantigen in mouse β-cells; and (3) the mouse model has a genetic background resulting in compromised β-cell neogenesis or proliferation.

MHC class II molecules are a class of MHC molecules normally found only on antigen-presenting cells. In humans, the MHC class II protein complex is encoded by the human leukocyte antigen gene complex (HLA). HLAs corresponding to MHC class II include HLA-DP, HLA-DM, HLA-DOA, HLA-DOB, HLA-DQ, and HLA-DR. In some embodiments, the MHC class II molecule expressed by the mouse model in antigen presenting cells is DQ8. DQ8 is a serotype within the HLA-DQ serotype group. DQ8 is the DQ most linked to human type 1 diabetes. Having the HLA-DQ8 gene tends to make humans susceptible to T1D.

Although antigen presenting genes are important determinants of genetic susceptibility in T1D, it is believed that it is presentation of primary target antigen(s) in the context of these genes that results in development of disease. Without wishing to be bound by theory, it is believed that in the mouse model described herein, which is an animal model of human T1D, human diabetes susceptibility genes and human target antigens coexist to mimic human autoimmune responses.

An autoantigen is an antigen that evokes an immune response by the host and stimulates autoantibody production. In some embodiments, the human β-cell autoantigen expressed by the mouse model in mouse β-cells is Glutamic Acid Decarboxylase isoform 65 (GAD65). GAD65 is an isoform of glutamic acid decarboxylase (GAD), which is an enzyme that catalyzes the decarboxylation of glutamate to gamma-aminobutyric acid (GABA) and $CO_2$. GAD65 is an important autoantigen in T1D, and is present in substantially more T1D patients than insulin autoantigens. GAD65 is coded by the GAD2 gene, and expressed in the insulin-producing β-cells of the human pancreas. However, mice β-cells normally mostly express GAD67, not GAD65.

GAD65 expresses naturally in a region different from where it is located in the mouse model described herein. In the mouse model described herein, GAD65 is expressed under the rat insulin promoter (RIP). Without wishing to be bound by theory, it is believed that the mouse model expresses GAD65 when expressing insulin, and therefore makes GAD65 whenever the mouse model makes insulin. Without wishing to be bound by theory, it is believed that the mouse model may be hyperinsulinic, and therefore make more GAD65.

In alternative embodiments, the human β-cell autoantigen expressed by the mouse model in mouse β-cells is islet antigen-2 (IA-2) instead of, or in addition to, GAD65. IA-2 is found in neural tissue and cells of the pancreatic islets, and its gene has been localized to chromosome 2q35. Autoantibodies to IA-2 are present in a significant amount of children and adolescents at diagnosis of type 1 diabetes.

In alternative embodiments, the human β-cell autoantigen expressed by the mouse model in mouse β-cells is a modified insulin. Human insulin and mouse insulin are very similar, so the insulin is modified with an antigen to evoke an immune response.

A mouse model line that expresses human GAD65, referred to as RIP7-hGAD65 transgenic C57BL/6 mice, is known. These mice express human GAD65 from the RIP. Expression of GAD65 in the pancreatic beta cells of these mice results in a modest decrease in first-phase insulin secretion, however diabetes never develops in the RIP7-hGAD65 transgenic C57BL/6 mice. The expression of GAD65 in the RIP7-hGAD65 transgenic C57BL/6 mice model is restricted to pancreatic beta cells and the level of expression is similar to endogenous expression of GAD65 in human beta cells (as opposed to negligible expression in non-transgenic mice).

The combination of human diabetes-susceptibility gene HLA-DQ8 (dominant susceptibility tissue type in humans) expressed as a transgene in antigen presenting cells and human beta cell autoantigen GAD65 expressed as a transgene in mouse beta cells increases the chances of mice to develop human-like T1D. Previously, hGAD65 transgenics were bred with mice in which endogenous mouse MHCII antigens have been replaced with the human HLA-DQ8 susceptibility locus for diabetes, referred to as murine MHC-class II molecule-deficient (mII-) C57BL/6 mice. However, spontaneous diabetes did not develop in these mice. DNA-vaccination of these double transgenics with a cDNA encoding hGAD65 resulted in induction of autoimmunity and lymphocytic homing to pancreatic islets. However, diabetes did not develop in these C57BL/6 double transgenics. Aside from experiencing transient fluctuation of fasting blood glucose, the mice were glucose tolerant. Signs of mitotic activity in some islets indicated that β-cell neogenesis/proliferation was present and could account for the glycemic control observed.

Mouse-strain variations with compromised β cell neogenesis/proliferation expressed as relative insulin deficiency were searched for. In some embodiments, the genetic background resulting in compromised β-cell neogenesis or proliferation is a BTBR background. BTBR mice exhibit an absence of the corpus callosum and a severely reduced hippocampal commissure. BTBR mice have lower whole-pancreas insulin content without developing diabetes. Without wishing to be bound by theory, it is believed that possible mechanisms which may account for this difference include deficient β cell neogenesis/proliferation, and/or increased apoptosis. The same transgenes previously incorporated to the C57BL/6 strain were introduced into the BTBR genetic background to convert a somewhat diabetes resistant animal model into a more diabetes-prone one. The humanized transgenics in the BTBR background mice developed antigen-specific insulitis, which progressed to mild insulitis followed by mild autoimmune diabetes upon induction with immunization of adenoviral vectors carrying human GAD65. The humanized transgenics in the C57BL/6-BTBR congenic mice developed antigen-specific insulitis which progressed to autoimmune diabetes. The dam (female) and the sire (male) were set to express all transgenes and background genes simultaneously to induce diabetes spontaneously. While expanding the colony, fasting glucoses were checked on every generation. After fixing the expression of all transgenes and background genes together in the pancreatic islet, the mice were incrossed based on highest fasting blood glucoses before crossing. An index case of a mouse with spontaneous hyperglycemia was detected during random surveillance in N>30. Thus, described herein is the occurrence of spontaneous autoimmune diabetes (SAD), the selective expansion of the SAD model, and the comprehensive assessment of the diabetes phenotype and its complications in the developed SAD transgenic model.

In some embodiments, the mouse model described herein is null for its own MHCII and expresses human MHCII (DQ8) in all antigen-presenting cells. The pancreatic islet β-cells of these mice were made to express human GAD65. The mouse model mimics human T1D at its best. The mouse model initially develops anti-GAD65 antibodies while lymphocytic infiltration builds up in the peri- and intra-islet location. Initially, glucose intolerance and later diabetes develop. Without intervention, the mouse model develop the classic complications observed in human diabetes, such as retinopathy, nephropathy, and neuropathy. All complications of diabetes have been observed in the mouse model.

The mouse model described herein spontaneously becomes hyperglycemic, sometimes after about 20 days. By contrast, in the non-obese diabetic (NOD) mouse model, the mice become diabetic after about 12 weeks. In other models, diabetes must be induced by immunization of a viral constructs of GAD65 or other proteins. Thus, the mouse model described herein becomes diabetic faster than known mouse models of T1D. Furthermore, as seen in the examples herein, the mouse model develops the classic complications of diabetes. The mouse model is the closest to human diabetes of known mouse models and is useful not merely to develop therapies to halt or hinder diabetes and its development but also to develop therapies to address diabetes complications. Furthermore, in contrast with NOD, the mouse model spontaneously develops diabetes in sterile as well as regular environments.

As described in the examples herein, the mouse model has been produced through a process of backcrossing, intercrossing, and incrossing HLA-DQA1*0301/DQB1*0302 (DQ8) transgenic, murine MHC-class II molecule-deficient (mII-) C57BL/6-BTBR congenic mice, RIP7-hGAD65 transgenic C57BL/6-BTBR congenic mice to produce mice with a spontaneous type 1 diabetes, and selectively incrossing the mice based on a high fasting glucose. However, the mouse model described herein may be produced through other methods. For example, clustered regularly interspaced short palindromic repeats (CRISPR)-Cas9 genome editing could be used to insert genes coding for DQ8 and GAD65 into C57BL/6-BTBR congenic mice, provided that the GAD65 is inserted under the insulin promoter together with inserting islet specific recognition molecules in cytotoxic T cells of C57BL/6-BTBR congenic mice.

The mouse model and methods for producing the mouse model may be embodied in the form of a kit or kits. A non-limiting example of such a kit is a kit comprising a breeding pair of the mouse model described herein, where the breeding pair of transgenic mice may or may not be housed in separate containers which may or may not be present in a combined configuration. For example, a kit may include a first mouse model that develops type 1 diabetes spontaneously, and a second mouse model that develops type 1 diabetes spontaneously, where the first mouse model and the second mouse model are capable of breeding to produce a third mouse model that develops type 1 diabetes spontaneously. Many other kits are possible, such as kits that further comprise a mouse food. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example I

Mouse Model of T1D

Transgenic, murine MHC-class II molecule-deficient (mII-) C57BL/6-BTBR congenic mice and RIP7-hGAD65 transgenic C57BL/6-BTBR congenic mice. Mice were subsequently crossed based on highest fasting blood glucose for >30 generations.

The spontaneous diabetes model manifested hyperglycemia after 30 generations of breeding selection based on high fasting blood glucose. The animals not only developed autoimmune diabetes, as indicated by the presence of islet lymphocytic infiltration and development of target autoantigen antibodies, but also acquired all the microvascular complications typical of human autoimmune diabetes.

Methods

Mice

HLA-DQA1*0301/DQB1*0302 (DQ8) transgenic, murine MHC-class II molecule-deficient (mII-) C57BL/6-BTBR congenic mice and RIP7-hGAD65 transgenic congenic mice were incrossed. DQ8 and hGAD65 homozygosity was determined as previously described. Mice were subsequently crossed based on highest fasting blood glucose for >30 generations. All animal protocols were approved by the University of Toledo animal research committees.

Histology and Immunohistochemistry

Pancreatic cells were snap-frozen in Tissue Tek (Miles Laboratories, Elkhart, IN). 5 μm-thick sections were stained with hematoxylin/eosin and biotinylated mAb directed against CD8 (Serotec, Raleigh, NC) followed by streptavidin-FITC conjugate and TO-PRO 3 (Molecular Probes, Eugene, OR) as counter-stain. Apoptotic cells were identified in pancreatic sections using transferase-mediated dUTP nick-end labeling (TUNEL) (Roche Applied Science, Indianapolis, IN). Then tissue slides were washed in PBS and double stained with anti-GAD65 antibody. Nuclei were also counterstained with TO-PRO 3. All images were acquired by confocal microscopy.

Antibody Measurement

Anti-GAD65 antibodies from mice serum samples were quantified with an ELISA kit (Kronus, Boise, ID) according with manufacturer instructions. Validation of the ELISA results was done with a parallel immunoprecipitation assay previously standardized. Control-mouse serum samples showed less than 5 U/ml of anti-GAD65 antibody concentration. At least two independent experiments in duplicated wells were performed, and average values for each sample were obtained.

Glucose Measurements

Blood sugar was monitored once a week using a Bayer Contour (Bayer, Mishawaka, IN) glucometer after nicking the tail vein. Glucose tolerance test was performed as previously described.

Flow Cytometry

In all flow cytometry experiments, cells were stained with fluorochrome-conjugated antibodies against mice CD3, CD4, CD8, CD25, CD68, IL17, IFNg, and Foxp3 (BD Biosciences, San Jose, CA, USA) or isotype controls. For cell phenotyping, spleen and pancreas-infiltrating lymphocytes were obtained. Freshly isolated single cells were incubated with antibodies for 20 min on ice for cell surface staining, washed and fixed in 1% paraformaldehyde. A subset of cells was permeabilized with cytofix/cytosperm fixation and permeabilization solution (BD Biosciences) and stained with fluorochrome conjugated antibodies against mice intracellular proteins. Cells were also stained with Hoechst33342 (10 µg/ml) to gate live cells containing 2n-4n cellular DNA. Cells were acquired in a BD LSR II/ARIA II flow cytometer (BD Biosciences). The data were analyzed using FlowJo software (Treestar Inc).

Statistical Analysis

Flow cytometry data were statistically analyzed using SAS MIXED procedure (version 9.3, SAS Institute Inc, Cary NC, USA).

Results

Figure 1B:
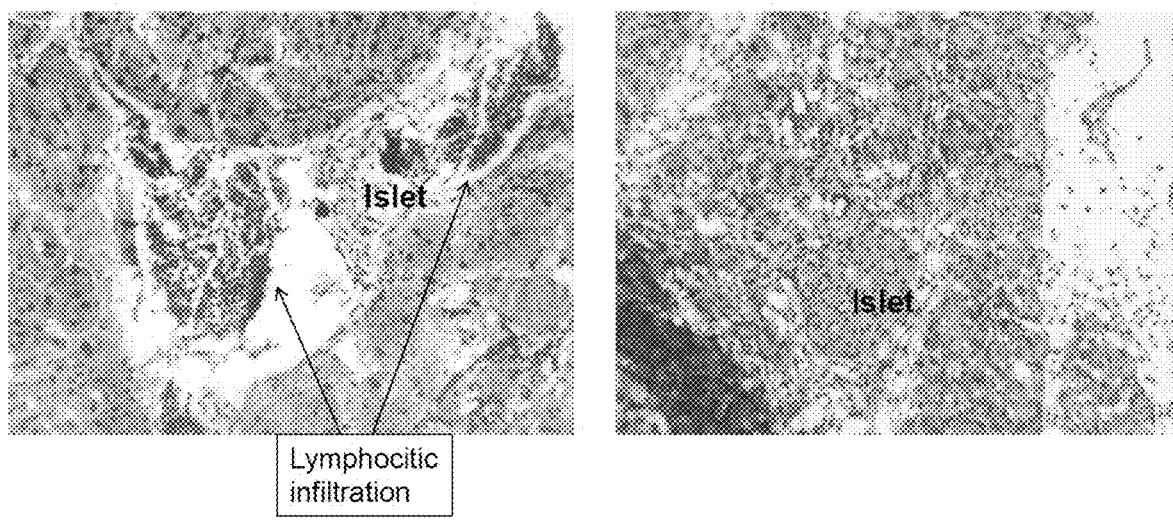

Spontaneous diabetes at 3 months in DQ8-hGAD65 mice (index case) (FIG. 1A histology, FIG. 1B GTT)

Spontaneous diabetes was not observed in prior models. Therefore, the ability of different immunization methods to generate insulitis and diabetes in groups of double-transgenic (DQ8-hGAD65+/+) in the C57BL/6-BTBR congenic mice was tested. A breeding colony was subsequently developed to provide experimental animals and continue the double-transgenic line. Mice were crossed based on highest blood glucoses. After approximately 30 generations, while checking these non-immunized animals for glucose, a 2-month-old male mouse was found to have fasting blood glucose of 366 mg/dl. Repeated value the following day was 351 mg/dl. Same cage male littermate had glucoses of 170 and 162 mg/dl on the same occasions. Both animals underwent glucose tolerance test (GTT). GTT clearly showed that the hyperglycemic animal was also glucose intolerant (FIG. 1A). After incrossing among the highest blood glucose a colony were generated having a high blood glucose. Animals from C57BL/6, BTBR, congenic and T1D group were subsequently euthanized and tissues processed. Pancreas was snap frozen for later sectioning and staining. The histology of the pancreas showed the typical lymphocytic infiltration of islets of Langerhans in the hyperglycemic animal (FIG. 1B).

Figure 2:
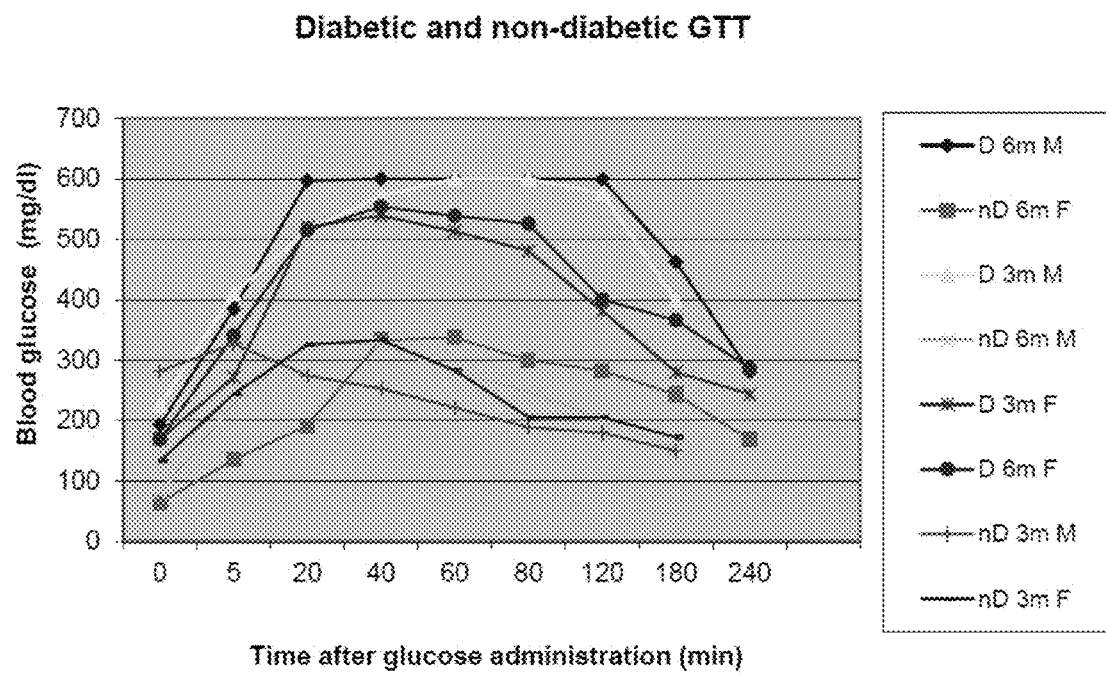
FIG. 2: GTT m&f with insets for extremes; GTTs of diabetic and non-diabetic animals by gender. Inset depicts GTTs that were followed longer than 120 min. Some diabetic animal glucoses did not return to baseline.
Figure 3:
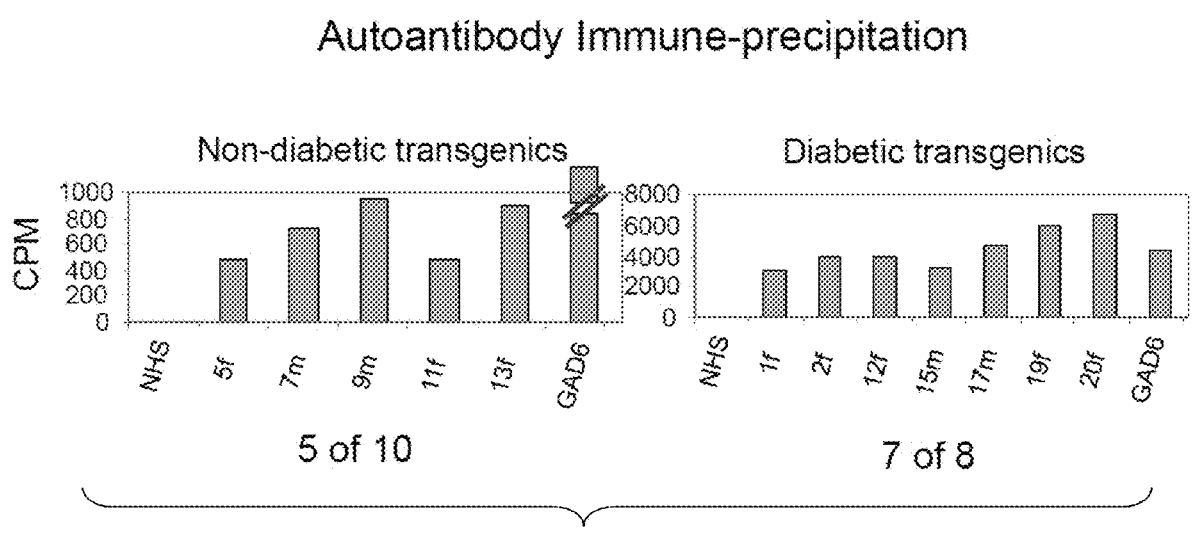
FIG. 3: GAD titer all animals m&f; GAD65 antibodies in mice. A world standard control for measurement of GAD65 antibodies (GAD6 mMAb) was used as a positive control in all immunoprecipitation experiments. The results were transformed to reactivity units (RU) by defining the maximum amount of GAD65 radioactivity precipitated by GAD65 mMAb as 100%. The experiments were carried out in duplicate and repeated at least three times. Not all non-diabetic animals developed detectable antibodies.

Systematic analysis of the colony (FIG. 2 GTT m&f; FIG. 3 GAD titer all animals m&f; FIGS. 7A-7D FACS)

In order to study the development and progression of the diabetes in the transgenic mice, 80 animals (40 males and 40 females) were followed over time by checking their fasting blood glucoses weekly. Animals were euthanized when fasting blood glucoses were >250 mg/dl in two consecutive days. About half of the animals reached that threshold by 3 months. The rest were followed for up to 6 months. Again, animals underwent glucose tolerance test (GTT) prior to being euthanized after the second glucose measurement above 250 mg/dl. The pancreas was then split in two. One half was snap frozen for later sectioning and staining. The other half was homogenized and filtered, to isolate lymphocytic infiltrates. Spleen and lymph-nodes (inguinal and peri-pancreatic) lymphocytes were also isolated by tissue homogenization and filtration of debris.

Pre-euthanasia GTT clearly showed that the hyperglycemic animal was also glucose intolerant (FIG. 2).

Antibodies to GAD65 were detected in all diabetic animals, indicating a lack of active tolerance to the GAD65 protein (regardless of the presence of the GAD65 transgene). Few of the non-diabetic animals used as controls also developed antibodies (FIG. 3).

Genotyping of DQ8 MHC II Haplotype by FACS

Figure 4A:
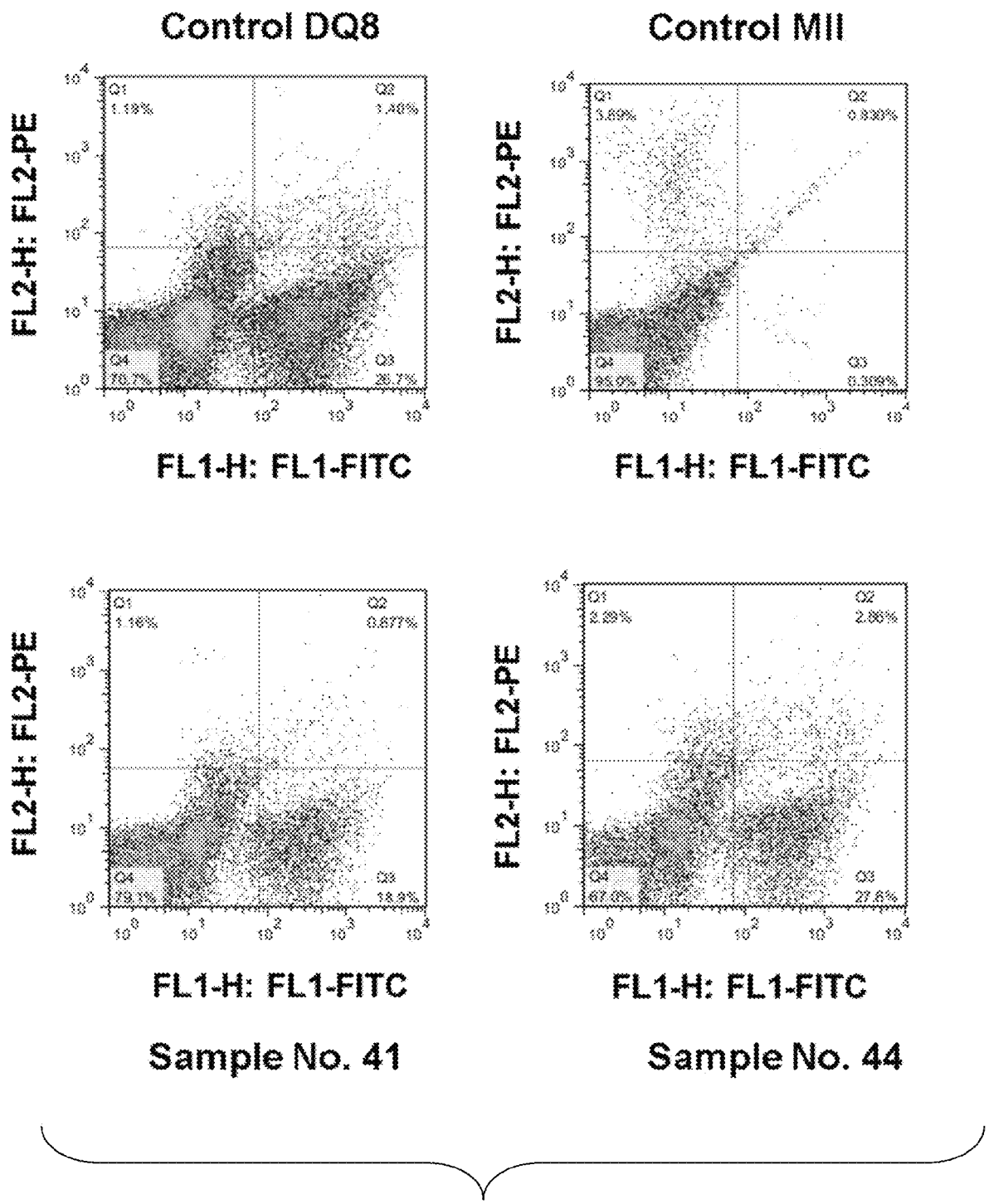
FIG. 4A: Genotyping of DQ8 MHC II Haplotype by FACS.

Genotyping of DQ8 MHC II haplotype by FACS was done for sorting a heterogeneous mixture of PBMCs which contains the DQ8 MHC II haplotype with the given protocol. (FIG. 4A).

DQ8 homozygosity was determined by screening simultaneously for DQ8 expression and absence of mII antigens using monoclonal anti-HLA-DQ antibody conjugated with fluorescein isothiocyanate (FITC) and monoclonal anti-murine MHC-class II (mII) antibody conjugated with phycoerythrin (PE) respectively. Cell-associated fluorescence was measured by flow cytometry (FACS).

Figure 4B:
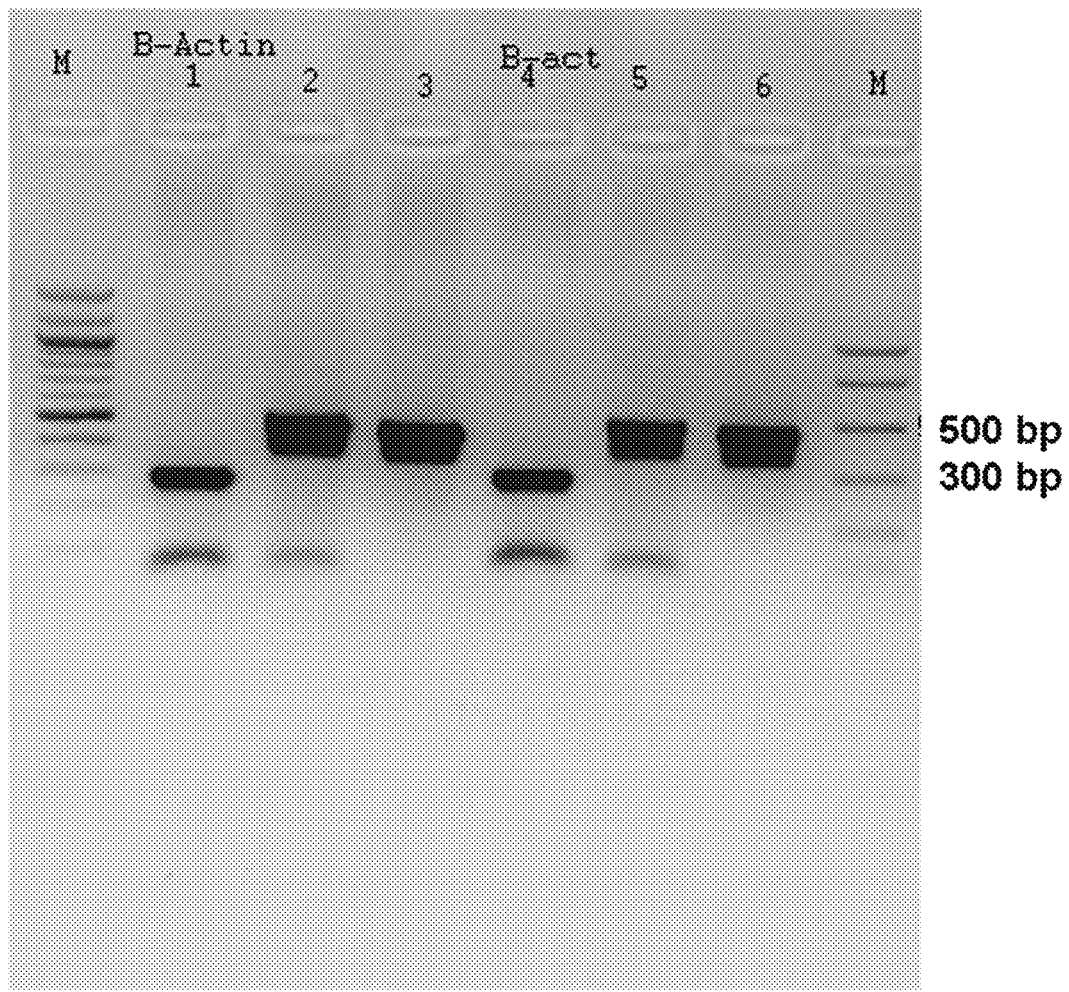
FIG. 4B: Genomic DNA from transgenic mice tail tip for genotyping of homologous RIP7 and GAD65 Gene by PCR.

Genomic DNA from transgenic mice tail tip for genotyping of homologous RIP7 and GAD65 Gene by PCR RIP7-hGAD65 expression was analyzed using isolation of genomic DNA from tail biopsy and PCR analysis of genomic DNA. Presence of transgene in the transgenic mice was analyzed by PCR amplification of RIP7-hGAD65 gene. It has been observed that lane 2, 3, 5 and 6 lane-containing sample possess the rat insulin promoter (RIP7)-human glutamate decarboxylase (hGAD65) hybrid gene of 400 bp (FIG. 4B). Amplification consists part of RIP7 and Human GAD 65. Thus Amplification results suggested that the mice model contains both transgene RIP (Rat Insulin promotor) 7 and Human GAD 65.

Example II

Spontaneous Diabetes Development in Triple Transgenic Humanized T1D Mice

One of the hallmarks of T1D is that the presence of adaptive responses against glutamic acid decarboxylase (GAD) 65 leads to humoral and cellular immunity Autoantibodies against GAD65 accurately predict T1D development in combination with other surrogate humoral biomarkers and they are considered the most sensitive and specific biomarker for T1D. GAD65 autoantibodies are found in 70% of newly diagnosed T1D patients and in only 0.5-4% of control subjects.

Figure 5A:
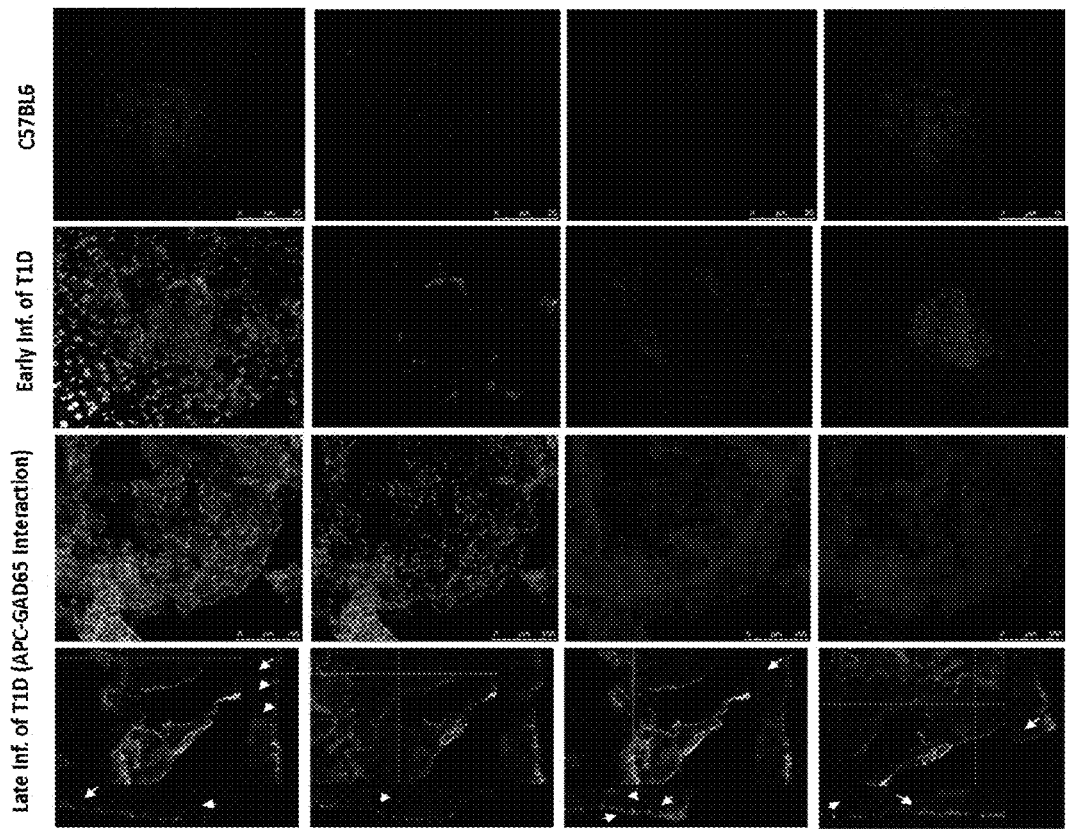
FIG. 5A: Confocal microscopy of humanized T1D or C57BL/6 mouse pancreatic frozen sections (8 µm): GAD65 (GAD65=Blue) seems to be present around peri-insular areas during earlier event of T1D in close contact with APCs (HLA-DQ8=Green). Beta cells were stained with antibody against Insulin (Insulin=Red). Confocal microscopy (high magnification, 100×) of T1D mouse pancreas with white arrows depicting beta cells GAD65-Blue and HLA-DQ8-Green (APCs) interaction and HLA-DQ8 (APCs)-Green interact with GAD65 (Blue) at an outer surface of the Beta cells.

Congenic C57BL/6 and BTBR were used for compromised β-cells neogenesis/proliferation. The ability of different immunization methods to generate insulitis and diabetes in groups of double-transgenic (DQ8-hGAD65+/+) in the C57BL/6 and BTBR background were tested. A congenic breeding colony (C57BL/6-BTBR) was subsequently developed with double-transgenes (DQ8-hGAD65+/+) to provide experimental animals and continue the double-transgenic line. DQ8 and hGAD65 homozygosity was determined. Mice were subsequently crossed based on highest fasting blood glucose for >30 generations. After approximately 30 generations, while checking these non-immunized animals for glucose, a 3-month-old male mouse was found to have fasting blood glucose of 366 mg/dl. Repeated value the following day was 351 mg/dl. Same cage male littermate had glucoses of 170 and 162 mg/dl on the same occasions. Both animals underwent glucose tolerance test (GTT). GTT clearly proved that the hyperglycemic animal was also glucose intolerant (FIG. 5A).

Figure 5B:
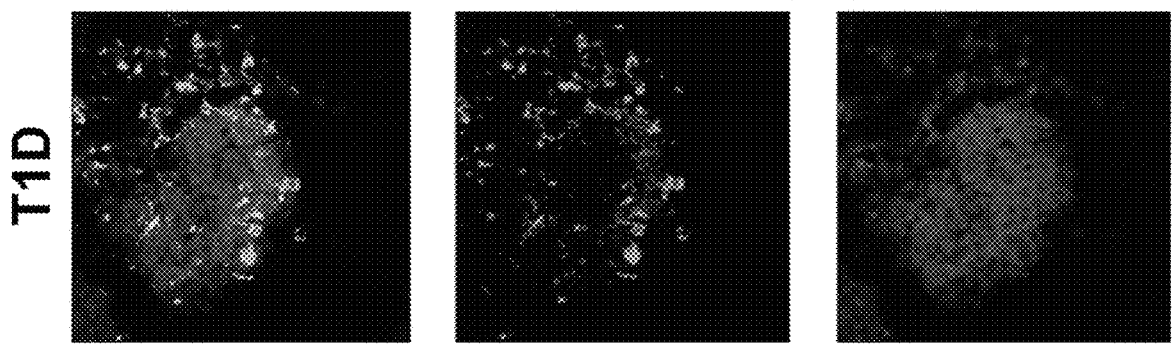
FIG. 5B: Confocal microscopy of humanized T1D mouse islets beta cells (Insulin=Red) surrounded by APCs (macrophages=Green).

Hyperglycemic animal colony were propagated and established on the basis of selection and breeding of high blood glucose phenotype. Some of the animals were subsequently euthanized and tissues were processed. Pancreas was snap frozen for later sectioning and staining. The histology of the pancreas showed the typical lymphocytic infiltration of islets of Langerhans in the hyperglycemic animal (FIG. 5B).

Pathophysiology of T1D in Humanized T1D Mice:

The mouse model of T1D resembles most characteristics of the human disease wherein mouse MHC-II was replaced by human DQ8 and β-cells were made to express human GAD65 auto-antigen under rat insulin promoter. Human and rat islets predominantly express GAD65 whereas, GAD67 is the major glutamic acid decarboxylase protein in mouse islets. GAD65/GAD67-positive vesicles in β-cells are distinct from insulin-containing vesicles and do not colocalize with insulin. GAD65 is primarily detected in Golgi membranes and in peripheral vesicles distinct from insulin vesicles in β-cells. GAD65 expresses at the same time insulin and both get expressed and stored into their respective exosomes, these exosomes play a role in intracellular communication. Exosomes are also a vehicle for disposing of extra cellular material which are in excess. For maintaining cellular homeostasis extracellular vesicles (EVs) are released around peri-insular area. These GAD65 carrying EVs interact with antigen presenting cells (HLA-DQ8) which in turn may lead to activation of innate immune responses, which subsequently triggers adaptive T and B cell responses against β-cell autoantigens, and as a result development of T1D.

Figure 5C:
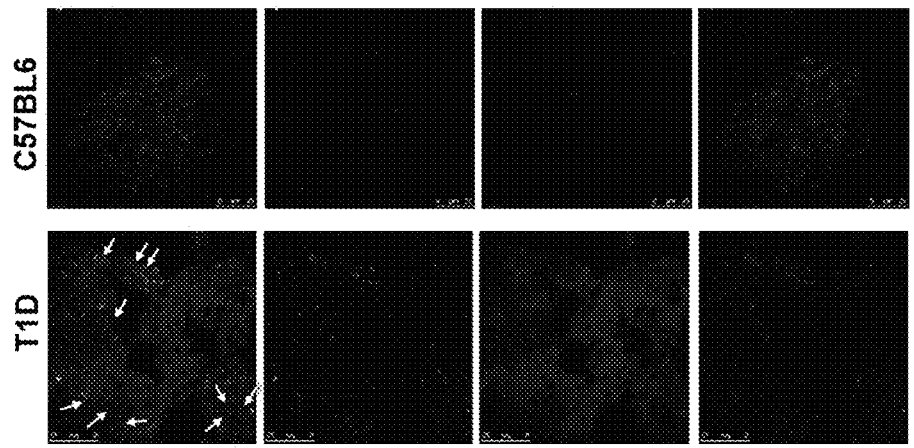
FIG. 5C: T1D mouse infiltrated/C57BL/6 mouse pancreas frozen sections were stained with Insulin=Red, Glucagon=Blue and PD-L1=Green, confocal immunofluorescence microscopy of pancreatic sections (8 µm) revealed that as opposed to C57BL/6, T1D humanized mouse model islet beta cells co-express PD-L1 (white arrow) in the chronic inflammatory microenvironment of T1D. Fully infiltrated islet beta cells hardly express Insulin and those beta cells expressing little insulin that were co-expressing PD-L1.

Immunofluorescence of pancreatic sections (8 μm) revealed that during early infiltration of islets in humanized T1D mouse, GAD65 expresses along with insulin that is finally released and accumulates into peri-insular area. While not wishing to be bound by theory, it appears that there is an interaction of peri-insular GAD65 with APCs (HLA-DQ8) in T1D mice. In FIG. 5C white arrows depicts beta cells-GAD65-Blue stained and HLA-DQ8-Green stained APCs interacting. The beta cell GAD65 interaction with antigen presenting cells (HLA-DQ8) we now believe leads to activation of innate immune responses (macrophages). In turn, humanized T1D mouse islets surrounded by APCs (macrophages) subsequently triggers adaptive T and B cell responses against GAD65 autoantigen.

Activated T cells express Program Death receptor 1 (PD-1) whereas, PD-1 ligand (L1) is expressed on antigen presenting cells, such as B cells, dendritic cells, macrophages, as well as various stromal cells, such as vascular endothelial cells and some pancreatic islet cells. Apparently, insulin containing β-cells express PDL-1 under special conditions (FIG. 5C, FIG. 5D).

Pancreatic islet of C57BL/6 and T1D humanized mouse were isolated using collagenase method and selected for architecturally integrity healthy islets. FIG. 5C, FIG. 5D depict individually isolated islets stained for Insulin=Red, Glucagon=Blue and PD-L1=Green. T1D mouse β-cells are shown to co-express PD-L1 ligand (detailed with white arrows) as compared to lack of expression in beta cells of C57BL/6 mice pancreatic islets.

While not wishing to be bound by theory, PD-L1 expression may be able to halt local effector T cell function in humanized T1D mice pancreatic islet but ultimately does not protect from full lymphocytic infiltration. In turn, peri-to-intra islet infiltration of cytotoxic CD8 T lymphocytes (CTLs) occurs with consequent destruction of pancreatic β-cells.

Figures 5D, 5E, 5F:
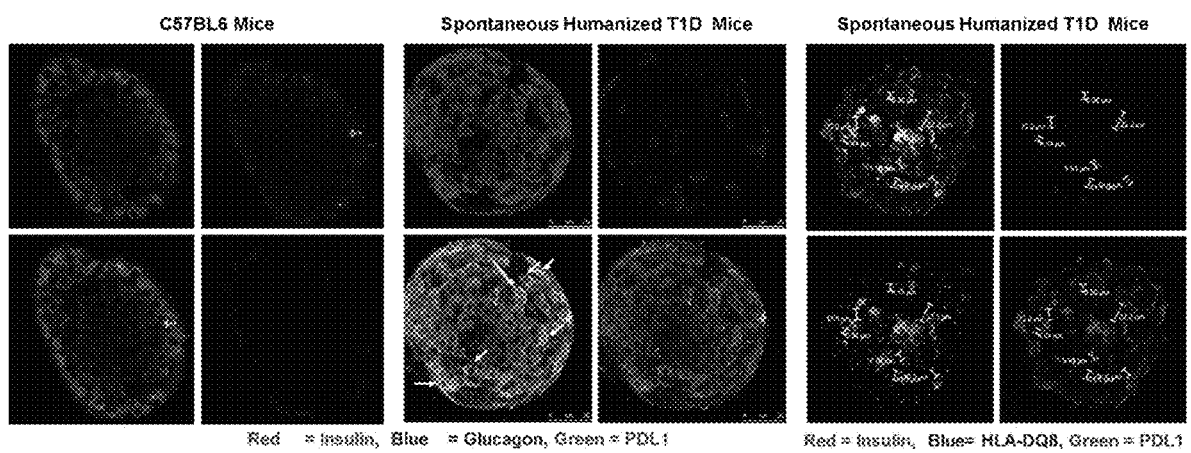
FIG. 5D: C57BL/6 and T1D humanized mouse Islets were isolated using collagenase method and selected the architecturally intact healthy islets for immunohistochemistry. T1D humanized mouse model islets contained proportionally more alpha cells found scattered throughout the islet architecture (see FIG. 1E) while C57BL/6 mouse islets had less alpha cells overall.
FIG. 5E: As opposed to C57BL6, in the chronic inflammatory microenvironment, T1D humanized mouse model islet beta cells co-express PD-L1 ligand (white arrow).
FIG. 5F: T1D humanized mouse model islet beta cells co-expressed PD-L1 (green) and insulin (red) while HLA-DQ8 (blue) was expressed by antigen presenting cells (macrophages, larger cells) remaining in the peri-islet area. Merged (yellow) revealed that Insulin producing beta cell also express PD-L1 and larger cells around beta cells were macrophages expressing HLA-DQ8 (blue).

The PD-L1 expression in β-cells of humanized mice as opposed to C57BL/6 mice indicates that expression of PD-L1 alone may not be sufficient to prevent T1D (FIG. 5C, FIG. 5D).

Immunofluorescence of pancreatic sections (8 μm) also revealed that as opposed to C57BL/6, T1D humanized mouse model islet beta cells co-express PD-L1 ligand (white arrow) in the presence of the chronic inflammatory microenvironment of T1D (FIG. 5C).

Individually isolated islet of T1D humanized mouse beta cells (insulin=red) co-express PD-L1 (green) while HLA-DQ8 (blue) expressing antigen presenting cells (macrophages, larger cells) remain in the peri-islet area (FIG. 5D) but not upon intra-islet infiltration.

Architectural Arrangements of Alpha, Beta and Delta Cells in the Islets of Humanized T1D Mice:

C57BL/6 and T1D humanized mouse Islets were isolated using collagenase method and selected for architecturally integrity healthy islets for immunohistochemistry. The humanized T1D mouse model carry the unique arrangement of alpha and beta cells present in human islets. In C57BL/6 mice, alpha cell distribution is restricted to the periphery of the islet while beta cells are located within the islet core. The T1D humanized mouse model islets contained not only proportionally more alpha cells found scattered throughout the islet architecture but also have more alpha cells than C57BL/6 mouse islets overall (FIG. 5D).

There is a unique difference between C57BL/6 and the T1D humanized mice—the healthy individually isolated islets of T1D mice mean fluorescent intensity (MFI) of insulin staining is significantly higher as compared to control C57BL/6 (FIG. 5D).

Figure 6A:
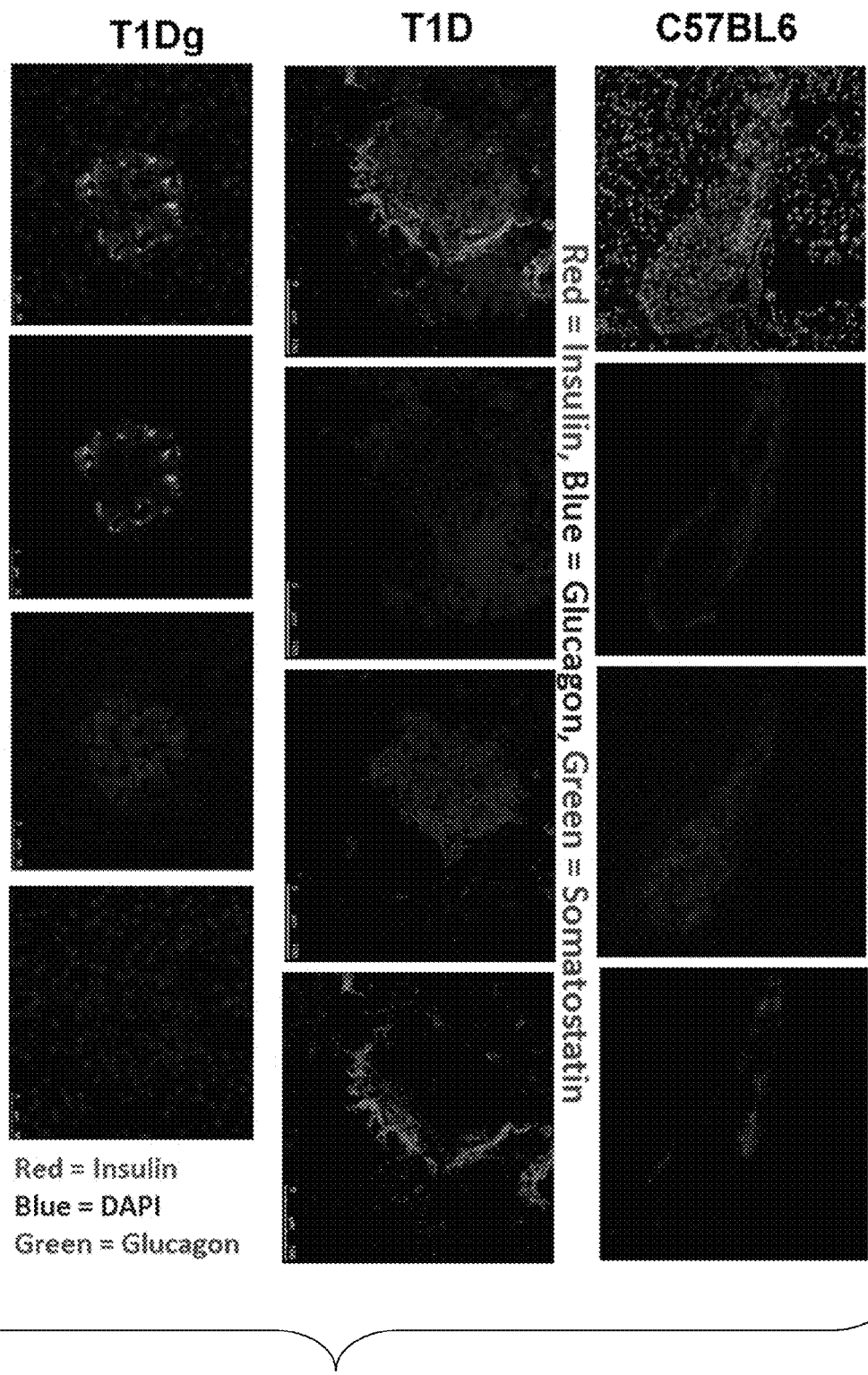
FIG. 6A: Confocal microscopy of humanized T1D mouse or C57BL/6 mice pancreas frozen sections (8 µm): Immunofluorescence of pancreatic sections revealed that humanized T1D mouse carry the unique architectural arrangement of alpha and beta cells present in human islets. Alpha and beta cell distribution are homogeneous and in paracrine pattern. In control C57BL/6, alpha cells are restricted to the periphery of the islet while beta cells are located within the islet core.

Immunofluorescence of pancreatic sections (8 μm) also revealed that humanized T1D mouse carry the unique architectural arrangement of alpha and beta cells present in human islets. Alpha and beta cell distribution are homogeneous and in paracrine pattern (detailed in FIG. 6A, T1Dg). In control C57BL/6, alpha cells are restricted to the periphery of the islet while beta cells are located within the islet core.

The number of isolated islet/pancreas in T1D mice were also ten times lower than the C57BL/6 control mice. More intense staining of insulin in T1D islet is believed to be because of and islet compensatory mechanism for insulin demand.

Figure 6B:
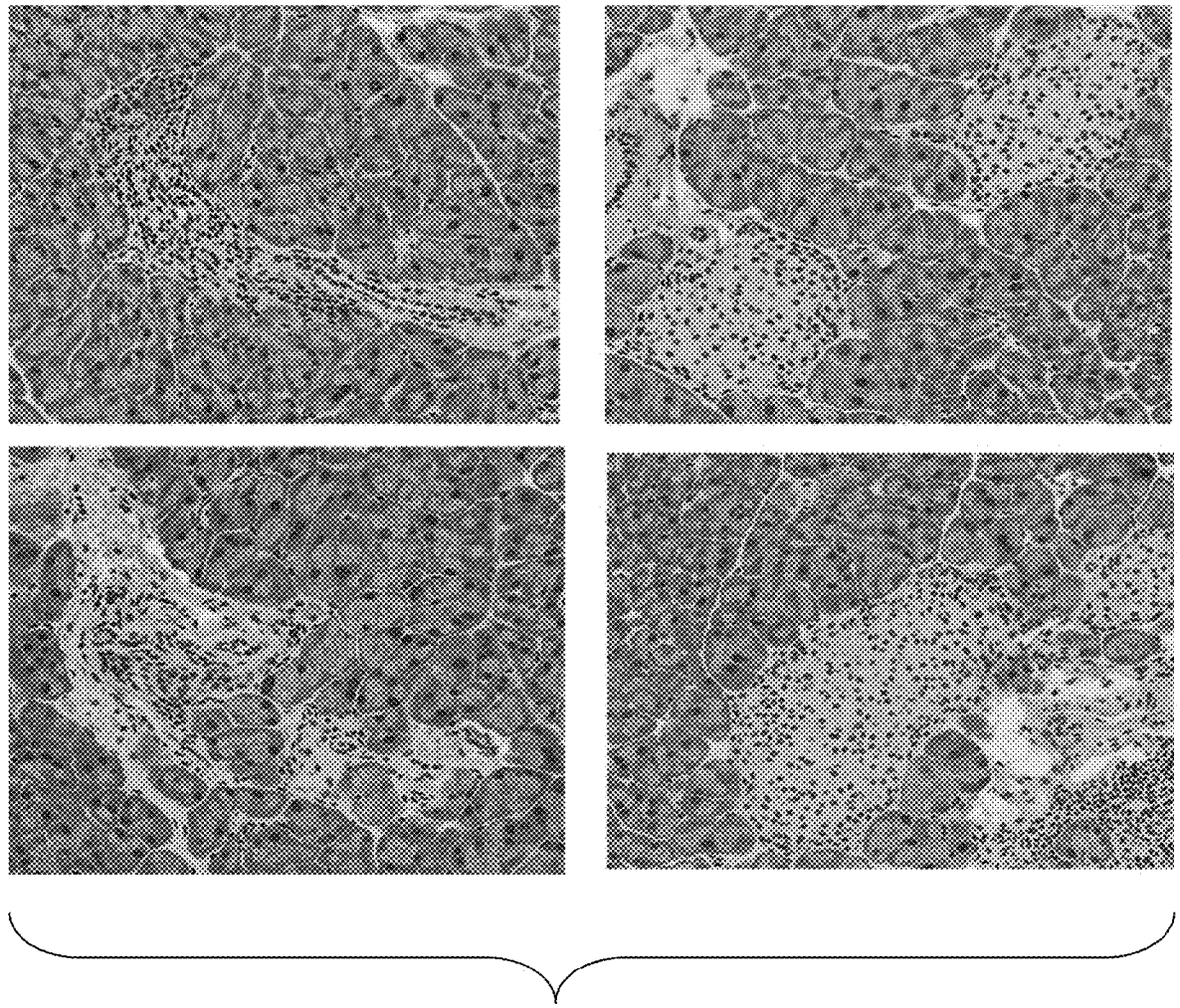
FIG. 6B: A representative image of H&E staining of pancreas from humanized mice islets.
Figure 6D:
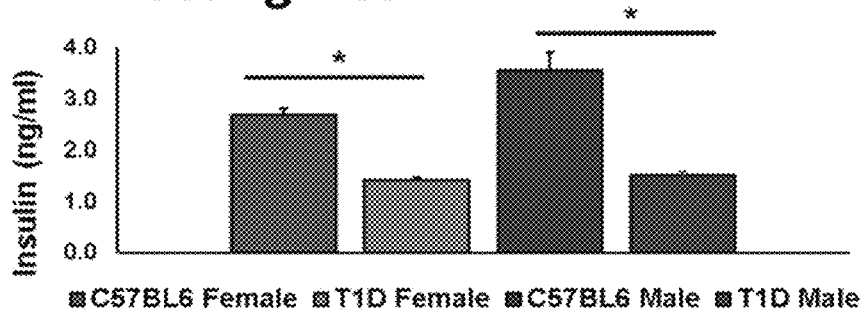
FIG. 6D: Fasting plasma insulin differences noted for C57BL6, BTBR, Congenic and T1D mice (n=8-16).
Figure 6E:
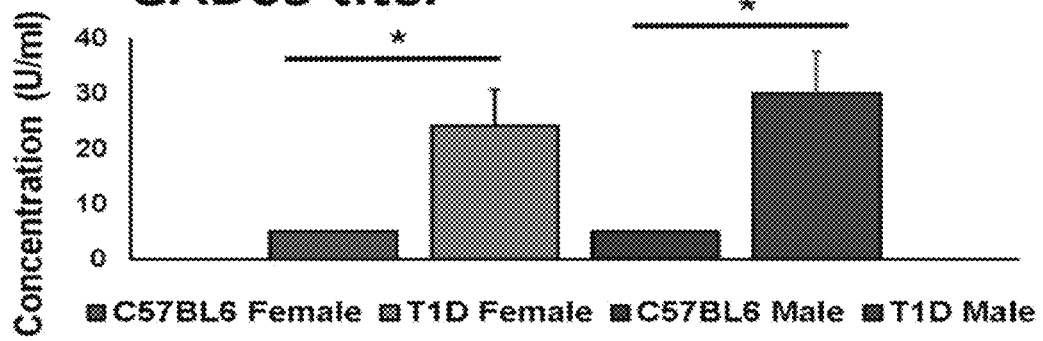
FIG. 6E: GAD65 autoantibody titers recorded for C57BL6, BTBR, Congenic and T1D mice (n=8-16).

Paraffin block sections of T1D mouse pancreas were stained with H&E. Some islet in T1D mice has intact islet architecture with infiltration, whereas some islets were small with disrupted islet architecture (FIG. 6B).

Auto-Antigen Specific Proliferation of Diabetogenic T Cells:

The diabetogenic T cells are auto-antigen specific in nature. The pancreatic lymph nodes (PLN) of a diabetic mouse were isolated and the single cell suspension was stimulated with recombinant human GAD65 protein (4 ug/ml). In-vitro proliferation assay using carboxyfluorescein succinimidyl ester (CFSE) to track the T cell proliferation was performed. Pulse stimulation with human rGAD65 (4 ug/ml) for 4 days increased the CD4 and CD8 proliferation by 9-10 folds (FIG. 6C). This demonstrates that the diabetogenic T cells (CD4 and CD8) in T1D mice show an auto-antigen specific proliferative behavior as observed in humans with T1D.

Physiopathological Parameters of T1D:

The activated immune cells against GAD65 attacks the pancreatic β-cells, which progresses chronically. Initially anti-GAD65 develop antibodies. Anti-GAD65 titers were inversely correlated with serum insulin and proportionally correlated with serum glucose and glucose tolerance test (GTT) (FIG. 6D, FIG. 6E, FIG. 6F, FIG. 6G, FIG. 6H).

Figure 6F:
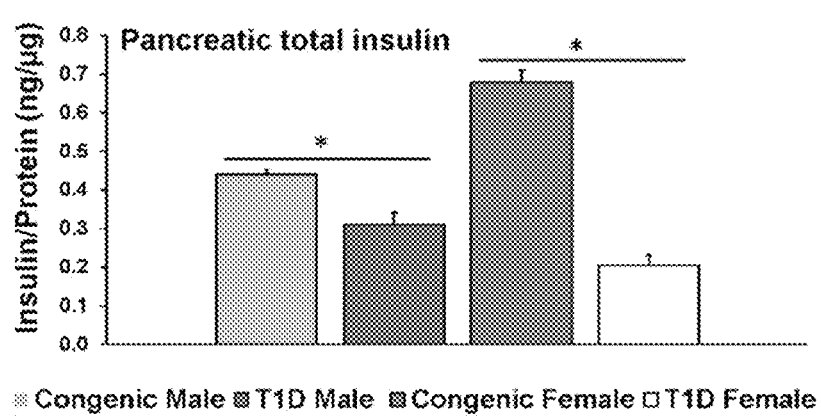
FIG. 6F: Pancreatic total insulin were measured in congenic and T1D mice and was significantly higher in the congenic mice as compared to T1D mice (n=8-16).
Figure 6G:
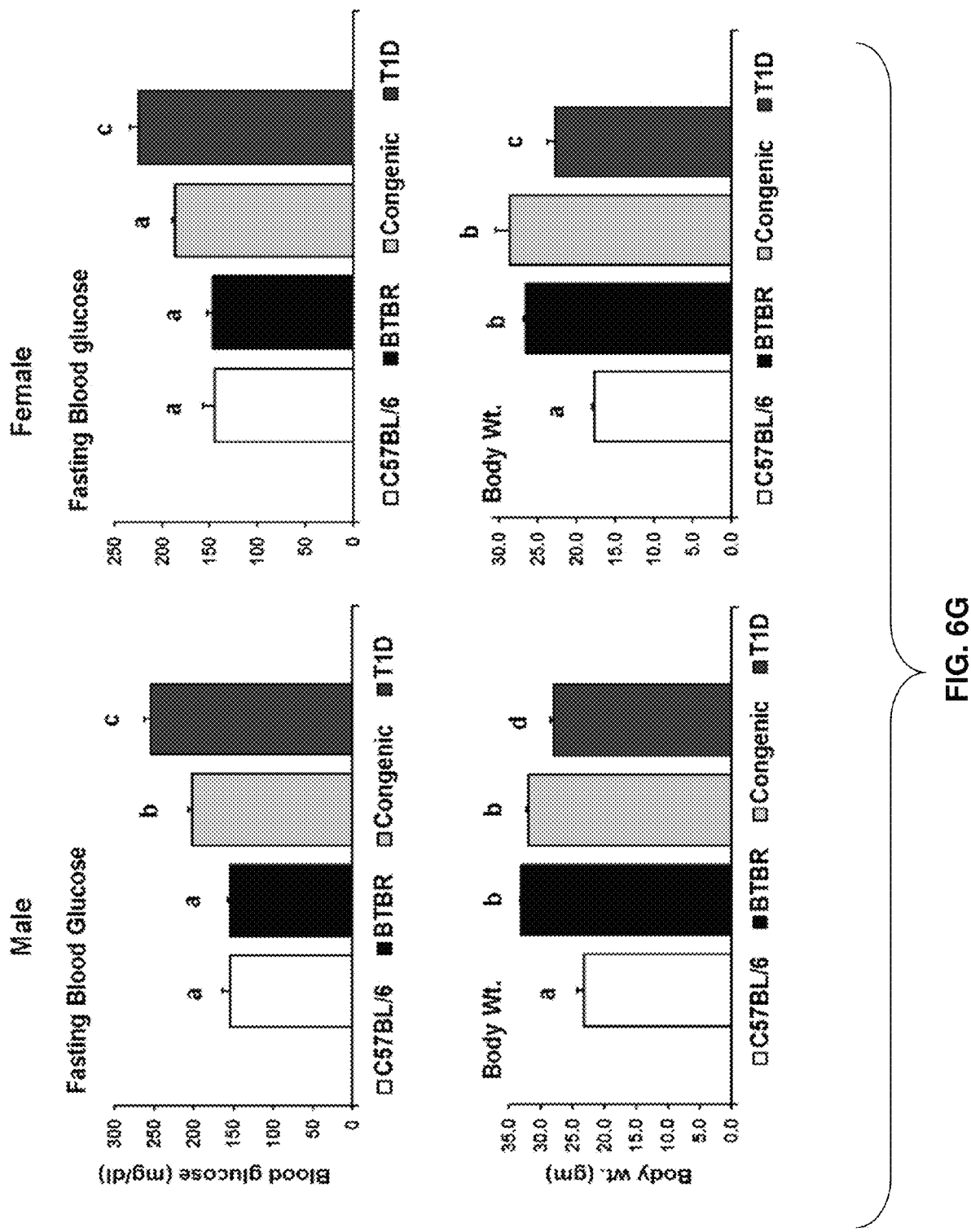
FIG. 6G: Fasting glycemia and weight monitoring: A significant glycemic differences and body weight were noted between C57BL6, BTBR, Congenic and T1D mice (n=8-22).

The total pancreatic insulin content was compared, and a significant reduction in the total insulin content in the T1D pancreas was found as compared to congenic mice strains (FIG. 6F). The humanized T1D mice signs and progression of diabetes were similar in both genders (like in humans) and the aggressiveness of T1D directly correlated with GAD65 titers. Body weight of T1D mice were significantly lower as compared to C57BL/6, BTBR and congenic mice like untreated human T1D.

Immune Cell Profiling using Flow Cytometry (Dot Plot and Histogram) of Four Organs:

Spleen (SP), inguinal lymph nodes (IGLN), peri-pancreatic lymph nodes (PLN) and pancreas (PN) of mice.

Figure 7A:
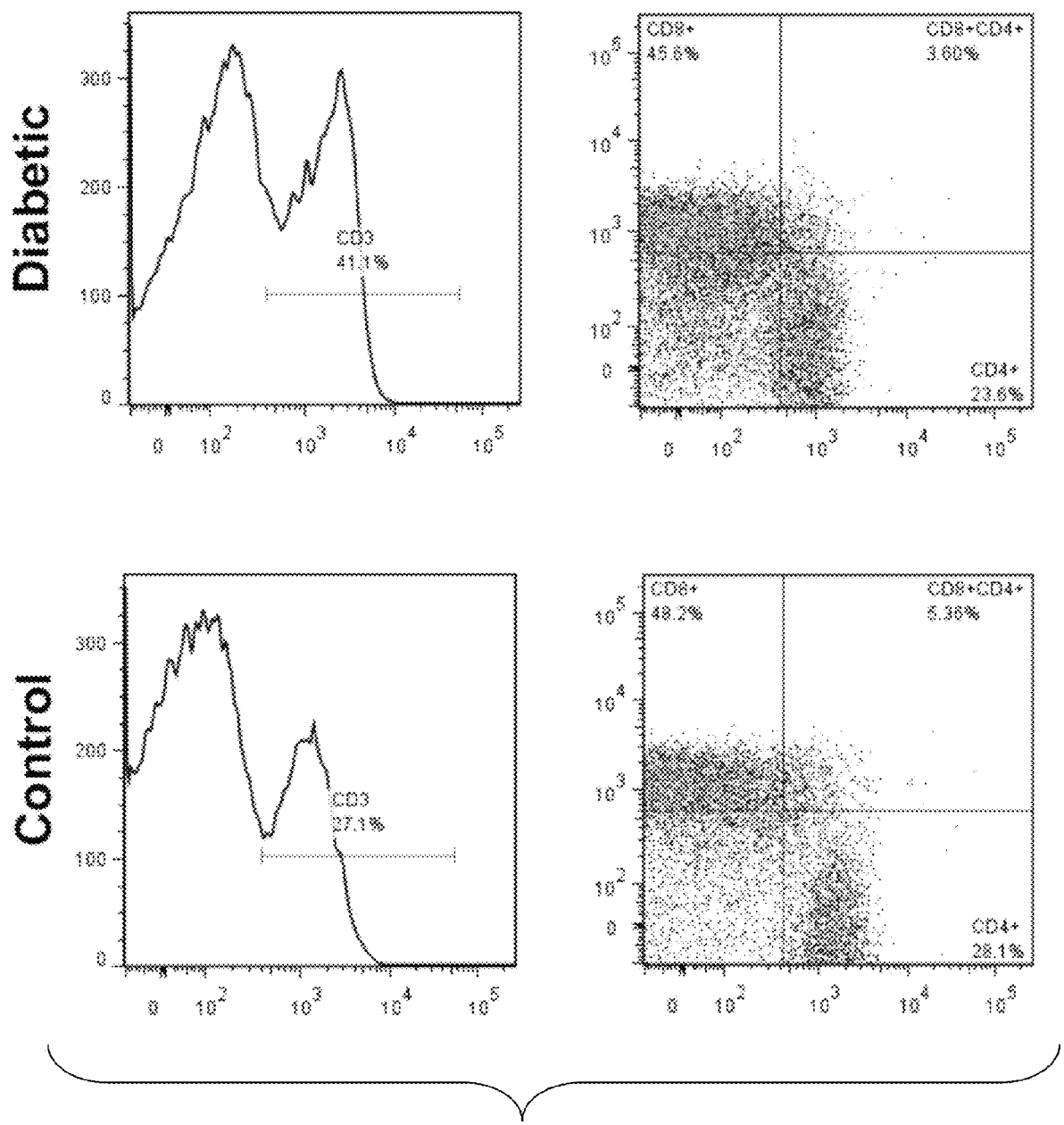
FIGS. 7A-7D: Lymphocytes from 4 anatomical sites of two animals, one with diabetes and a littermate healthy control, are shown: Spleen (FIG. 7A), Inguinal lymph node (FIG. 7B), Peri-pancreatic lymph node lymphocytes (FIG. 7C) of the diabetic animal already shows the CD3 dominance more prevalent when closer to the pancreas (FIG. 7D). The pancreas of the diabetic animal is clearly infiltrated by CD8>CD4; CD3 cells. The control is not.
Figure 7B:
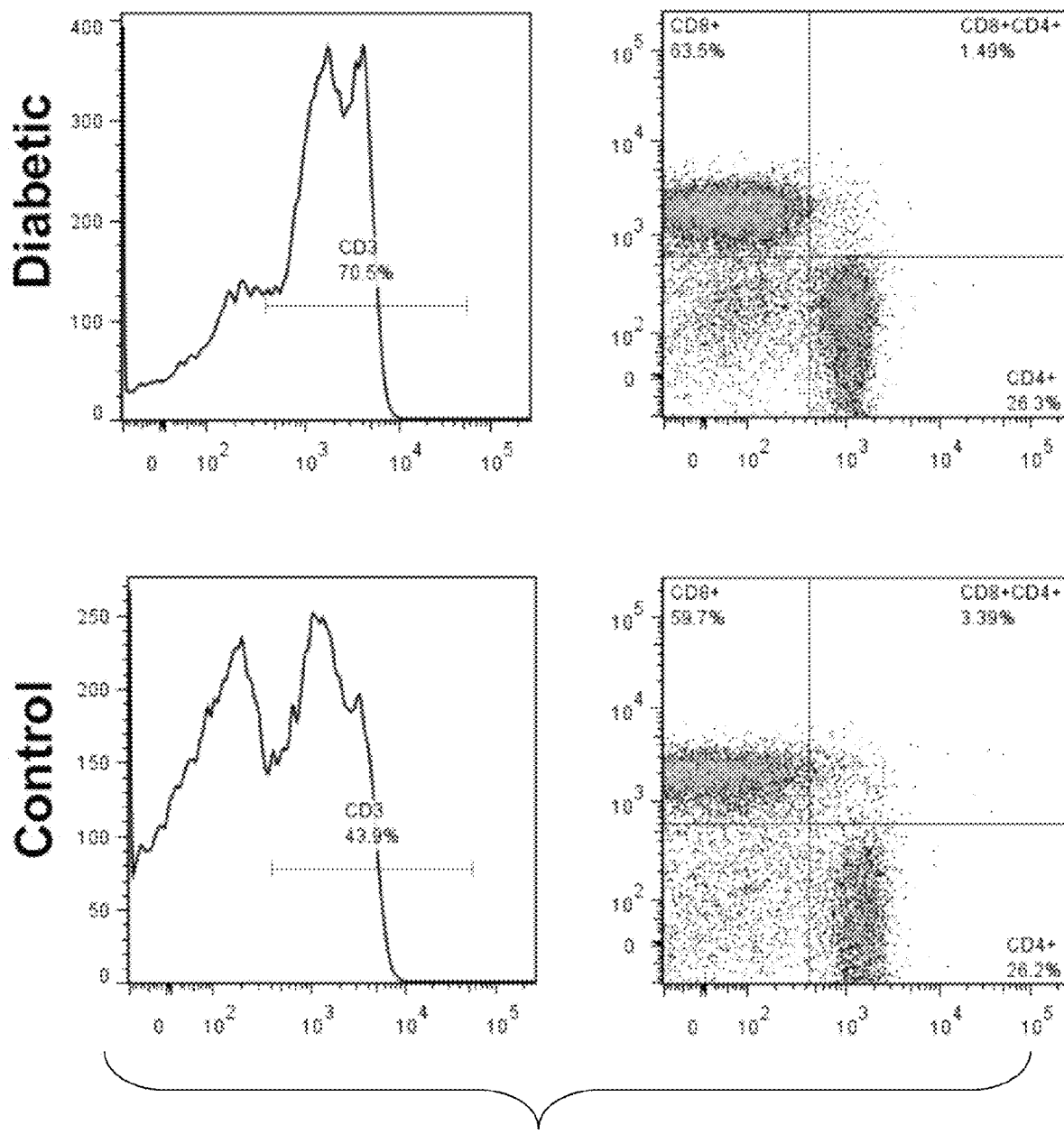

Organs were processed just after sacrifice, and single cell suspensions were stained with fluorochrome-conjugated antibodies. CD3s were gated from the total single lymphocytes, subsequently gated for CD4 and CD8 T cells (FIG. 7A). T cell profiling for CD3, CD4 and CD8 cells at SP, PN and PLN in C57BL/6, BTBR, Congenic and T1D mice (n=8-32 per group) are shown (FIG. 7B). Total number of T cells present in pancreas of humanized T1D mice were 50-200 times higher than the other three mouse strains (C57BL/6, BTBR, Congenic mouse models). The T cells present in PN were mostly (>90%) CD8 T cells. Proportion of CD4 T cells in T1D mice spleen, PLN and PN were significantly low out of total T cells (FIG. 7B), interestingly the proportion of CD4 in PN is only 2-3% (FIG. 7B) whereas proportion of CD8 in Spleen and PLN were significantly higher in humanized T1D mice. In T1D mice the percentage of CD8 T cells at PN were not higher than C57BL/6 mice, but the pancreatic population of CD3 were almost 200 times higher than C57BL/6, therefore, CD8 T cells present in PN of T1D mice were also almost 200 times higher than the CD8 T cell present in C57BL/6 mice.

Figure 7C:
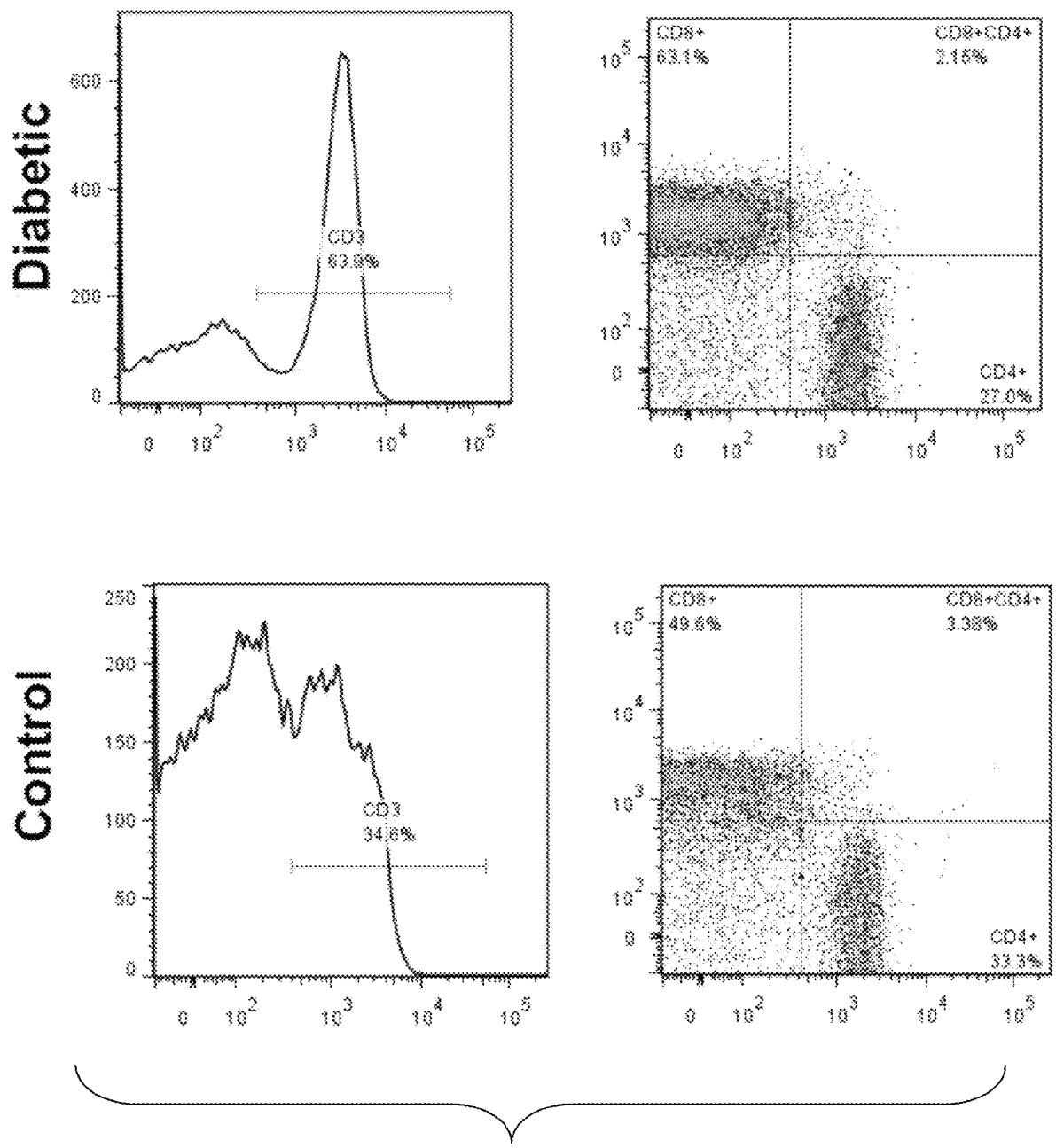
Figure 7D:
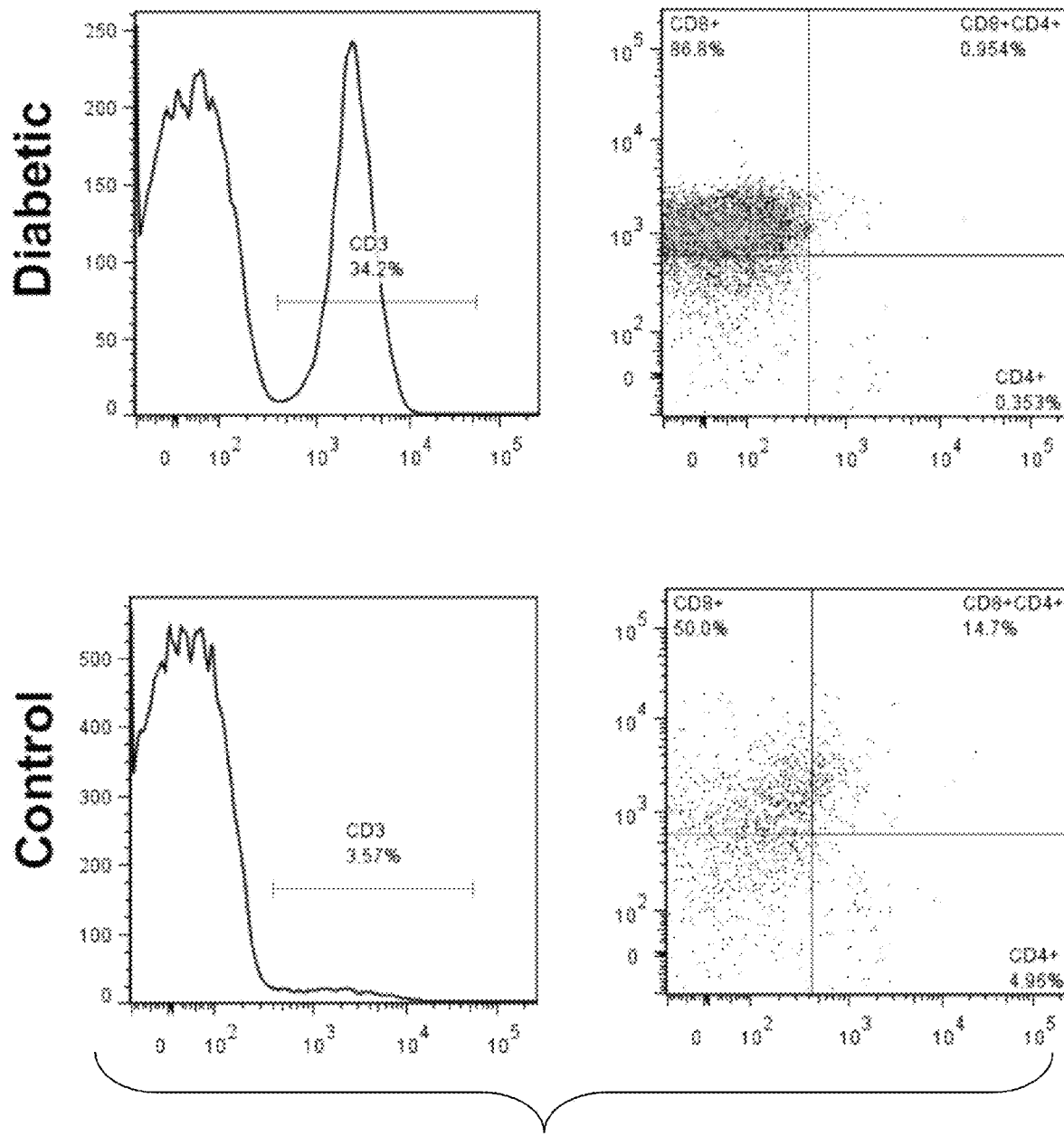

All lymphocytes were then stained with markers specific for different functional status. Intra-pancreatic (PN), splenic (SP), inguinal lymph node (IGLN), and peri-pancreatic lymph node (PLN) lymphocytes were characterized by Fluorescence-Activated Cell Sorting (FACS). Data for anti-CD3 (FIGS. 7A-7D, upper and lower left quadrants), and anti-CD4 and anti-CD8 (FIGS. 7A-7D, upper and lower right quadrants) positive lymphocytes from the four anatomical sites (from peripheral to central, Spleen, Inguinal lymph node, Pancreatic lymph node, and Pancreas) from representative diabetic and control mice are shown in FIGS. 7A-7D. Already at the spleen level, the CD3 population was over represented in the diabetic mouse (left histograms from diabetic and control spleen, FIG. 7A). The same was true for the CD4 and CD8 populations at the spleen level. At the inguinal lymph node level, the CD3 positive cells were clearly the dominant population for the diabetic animal (histograms A from diabetic animal 78% of all cells present in the Inguinal lymph Node were CD3+(FIG. 7B, right upper quadrant). Peri-pancreatic lymph node from diabetic animal kept the same dominant CD3 distribution and started to show a bias CD8 dominance in comparison with control (FIG. 7C, left lower quadrant). Most remarkably, pancreatic T lymphocytes were almost exclusively present in diabetic mice (only 3.57% in control, left histograms at pancreas level also in FIG. 7D). Furthermore, these intra-pancreatic T lymphocytes were mostly of the CD8 type.

Figure 8:
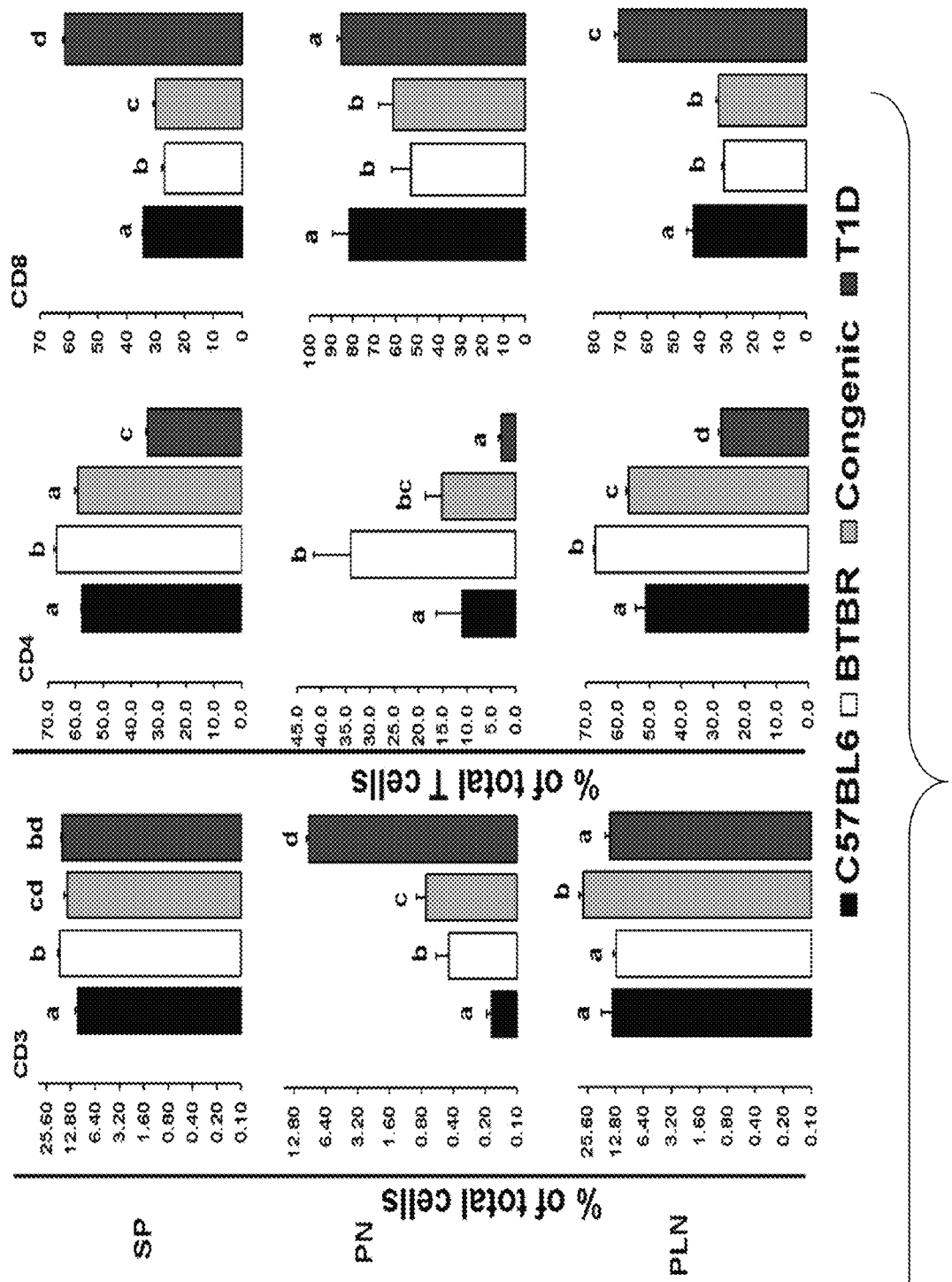
FIG. 8: Profiling of CD3 positive T cells (percentage of total cells), CD4 and CD8 T cells (percentage of total T cells) at SP, PN and PLN in C57BL6, BTBR, Congenic and T1D mice (n=8-32 per group) are shown. Statistical significance was determined at p<0.05. Lowercase letters (a-d) identify significant differences among the groups.

FIG. 8 shows the profiling of CD3 positive T cells (percentage of total cells), CD4 and CD8 T cells (percentage of total T cells) at SP, PN and PLN in C57BL6, BTBR, Congenic and T1D mice (n=8-32 per group) are shown. Statistical significance was determined at $p<0.05$. Lower-case letters (a-d) identify significant differences among the groups.

Regulatory T (Treg) Cell Population:

Regulatory T cells have an important role in negatively regulating hyperactive effector T cells (CD4/CD8/CTLs) which are induced during strong immune responses in peripheral and organ specific tissues. CD4 and CD8 T cells present in peri-pancreatic lymph nodes of the humanized mouse are hGAD65 antigen specific (FIG. 6C). Regulatory T cells were significantly lower in all the organs (Spleen, PLN and PN) of T1D mice as compared to other control mice strains (FIG. 9A).

T Helper Type 1 (Th1) and T Helper Type 17 (Th17) Population:

Interferon (IFNg) producing CD4 (Th1) T cells were analyzed into three organs of all the mice strains. Cellular profiling revealed that Th1 cells were significantly higher in the PLN of T1D mice whereas the Th1 percentage was non-significantly higher at spleen and PN (FIG. 9B).

However, in term of numbers, the Th1 cells present in T1D pancreas were significantly higher (50-200 times higher) as compared to other three mice strains (data not shown) Similarly, for interleukin (IL) 17 producing CD4 T cells, no difference were observed in term of percentage of Th17 cells (FIG. 9C) whereas, in term of numbers the Th17 cells present in T1D pancreas, they were significantly higher (50-200 times higher) as compared to other three mice strains (data not shown).

Cytotoxic CD8 T Cell (CTLs) Population:

Interferon producing CD8 (CTLs) cells were analyzed for three organs of all mice strains. CTLs data revealed that CTLs activation is organ specific in humanized T1D mice, in or nearer to pancreas. A significantly increased CTLs percentage were recorded at PLN and PN site whereas at spleen the CTLs percentages were significantly lower as opposed to what was observed in the other three mice strains. In terms of numbers, the CTLs count in T1D pancreas were (50-200 times) higher than in the control mice strains (FIG. 9D). Increase in the CTLs numbers nearer to pancreas in T1D mice show that CTLs were auto-antigen specific and they amplified on pancreatic auto-antigen stimulus.

Serum Profile of T1D Mice:

Serum profile of mice strains were performed using vetlab biochemical methods. Serum creatinine is a reliable indicator of kidney function and a high serum creatinine is associated with poor clearance of creatinine by the kidneys. An increase in the serum creatinine level in T1D mice at age 27 weeks was observed (FIG. 10A).

High total cholesterol (dyslipidemia) has been shown to correlate with progression of diabetic nephropathy. Intra-renal accumulation of lipids might contribute to glomerular injury. Serum profile of mice strains demonstrated a significant increase in serum total cholesterol in T1D mice (FIG. 10B).

Blood urea nitrogen (BUN) also gives an indication of the kidney function. A high serum BUN level may result from kidney damage and dysfunction. Impaired excretion of BUN by the kidney results in accumulation in the blood. Serum profile of mice strains revealed an increased serum BUN level in T1D mice (FIG. 10C).

Serum albumin maintain the osmoregulation of body fluids. Serum albumin was also measured in the mice strains and revealed no difference among the group (FIG. 10D).

High serum triglyceride associates with diabetes and has been shown to be involved in the development of Diabetic Nephropathy (DN). Under prolonged hyperglycemic milieu, hormone sensitive lipase activation, results in release of free fatty acid (FFA) from the adipose tissue. The instant flux of FFA promotes hepatic triglyceride conversion. The triglyceride serum level in mice strains was measured, and significant differences among the groups were found. There was a significant increase in serum triglyceride levels observed in T1D mice (FIG. 10E).

Diabetic Nephropathy:

Proteinuria in T1D Mice:

Proteinuria is a hallmark of diabetic nephropathy. Proteinuria insinuates glomerular damage, and is considered as a measure for severity of diabetic glomerulopathy. High proteinuria (nephrotic range) in diabetic nephropathy was strongly associated with pathological changes of diffuse and, nodular form of diabetic glomerulosclerosis. Clinical reports suggest that 87% of patients showing nephrotic syndrome in T1D and 70% patients showing nephrotic syndrome in T2D have diabetic nephropathy. It has been also reported that end-stage renal failure occurs in up to 75% of diabetic patients within 15 years of overt proteinuria. The proteinuria in the urine samples of mouse strains were measured, and a 10-30 fold increase in proteinuria of T1D mice was observed (FIG. 10F).

Diabetes Complications—Kidney

Figure 11A:
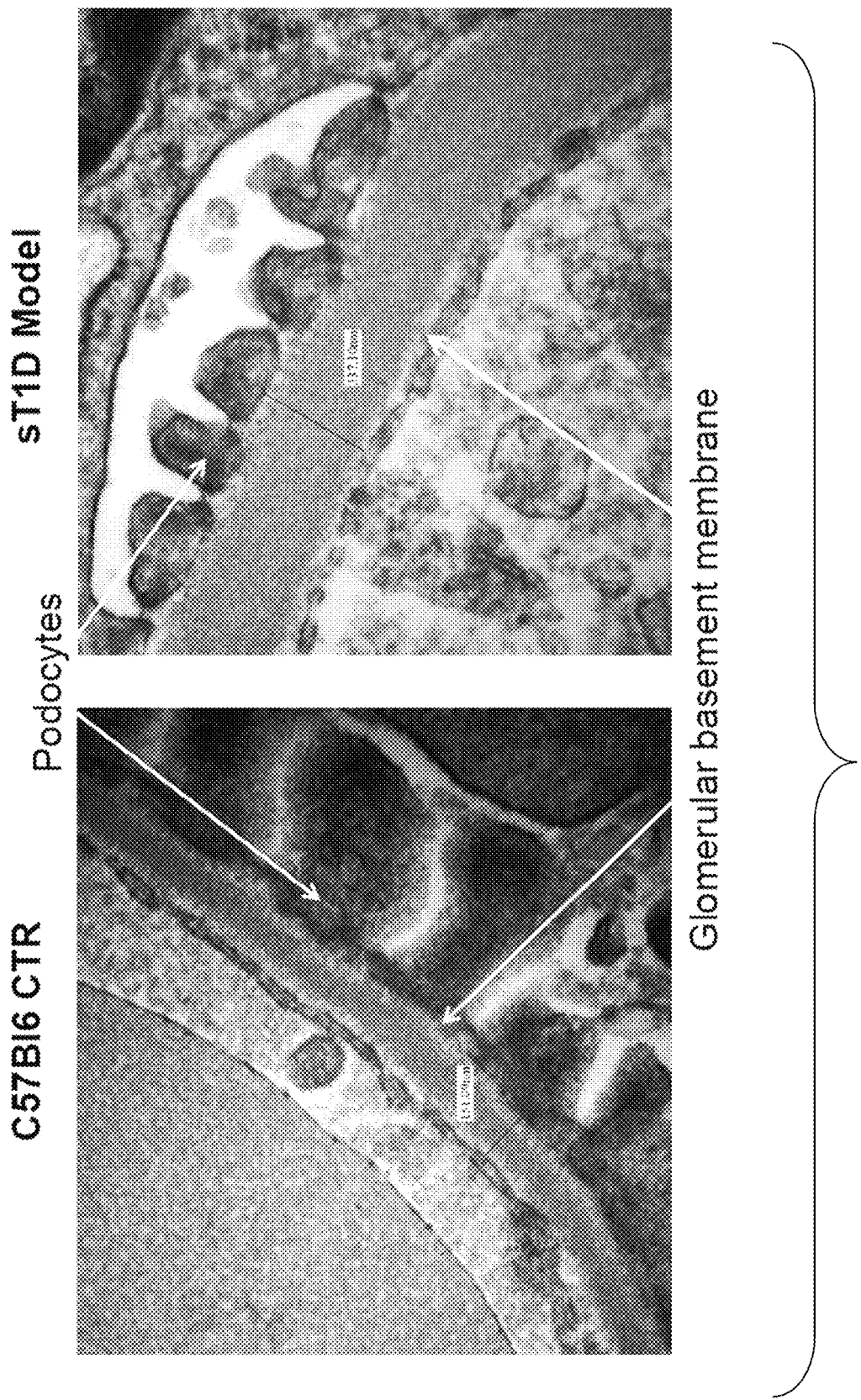
FIG. 11A shows a microphotograph showing thickening of the glomerular basal membrane. Podocyte effacement observed in T1D mice as compared to control mice. Podocyte dysfunction is an important cause of proteinuria. Glomerular basal membrane (GBM) expansion also recorded (almost doubled) defines earliest histologic feature of diabetic nephropathy.

Three-month-old mice showed thickening of the glomerular basement membrane. FIG. 11A shows an electron microscopy image where podocyte effacement recorded in T1D mice as compared to control mice. Podocyte dysfunction is an important cause of proteinuria. Glomerular basal membrane (GBM) expansion also recorded (almost doubled) defines earliest histologic feature of diabetic nephropathy. Light photomicrographs illustrate various stages of glomerular lesions and tubule-interstitial disease in T1D mice diabetic nephropathy.

Electron Microscopy of Diabetic Kidney:

Increased basement membrane width and mesangial expansion are known to precede the development of proteinuria in diabetic nephropathy. Mesangial and interstitial expansion appears to be correlated with the degree of proteinuria in the humanized T1D mouse model (FIG. 11A).

Effacement of podocytes is a prominent ultrastructural abnormality in diabetic nephropathy. Electron microscopy of kidney revealed a podocyte effacement in T1D mice as compared to C57BL/6 mice. Podocyte effacement may be an important cause of proteinuria.

Figure 11B:
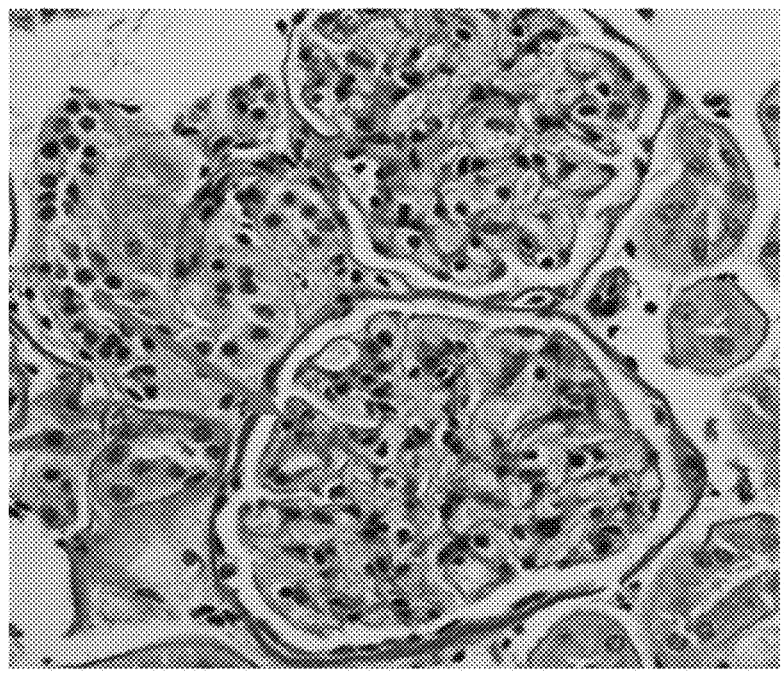
FIG. 11B: Light photomicrographs illustrate various stages of glomerular lesions and tubule-interstitial disease in T1D mouse diabetic nephropathy. PAS stain showing Kimmelstiel-Wilson disease of the glomerulus (orange arrow)
Figure 11C:
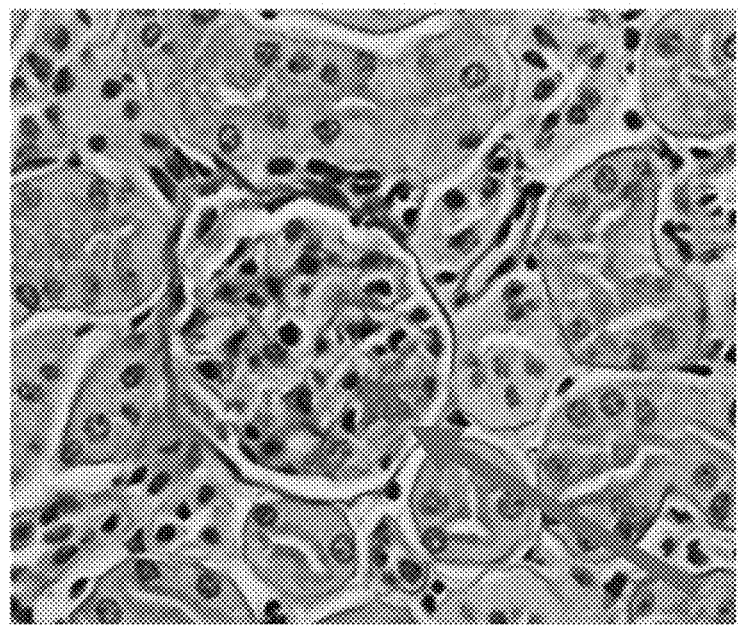
FIG. 11C: PAS stain showing Kimmelstiel-Wilson nodule in the glomerulus (orange arrow).

Light Microscopy of Diabetic Kidney:

Immunohistochemistry and light microscopy of mouse diabetic kidney revealed histological feature of diabetic nephropathy in humanized T1D mice. Periodic acid Schiff (PAS) staining showing a Kimmelstiel-Wilson lesion of glomeruli (orange arrow) (FIG. 11B and FIG. 11C).

Figure 11D:
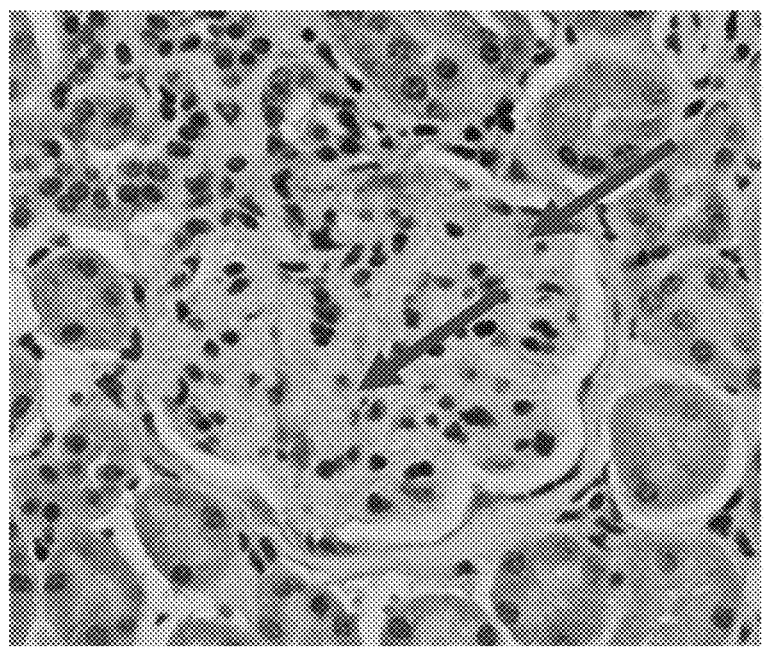
FIG. 11D: H&E stain demonstrating Kimmelstiel-Wilson mesangial expansion in the glomerulus (Blue arrows).

H&E staining also demonstrated Kimmelstiel-Wilson matrix expansion of glomerulus (blue arrow) (FIG. 11D).

Figure 11E:
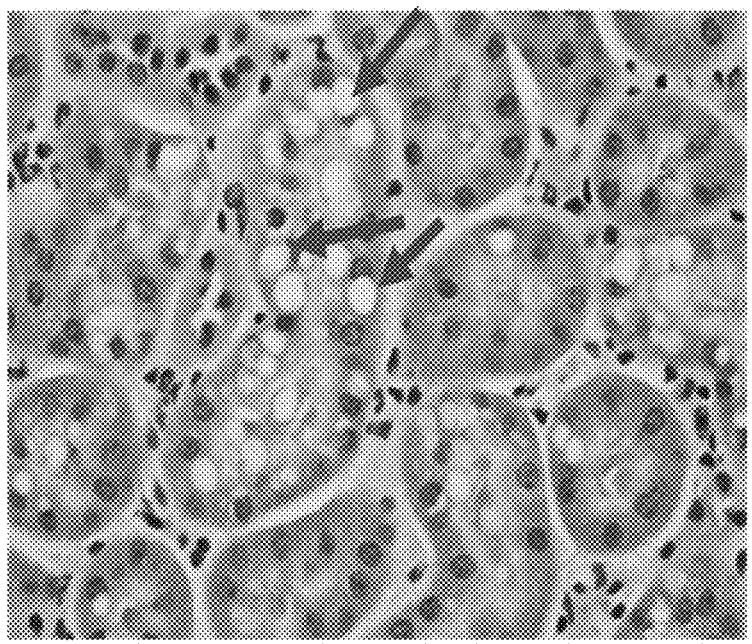
FIG. 11E: H&E stain showing vacuolization (blue arrows) in the tubules.

H&E light microscopy also revealed some abnormalities of kidney tubules characterized by the presence of clear vacuoles (vacuolation) in renal tubular epithelium (blue arrow) (FIG. 11E). Osmotically active compounds such as glucose result in "osmotic nephrosis," which in human kidney biopsy appears as cytoplasmic vacuolation of kidney tubules.

Figure 12A:
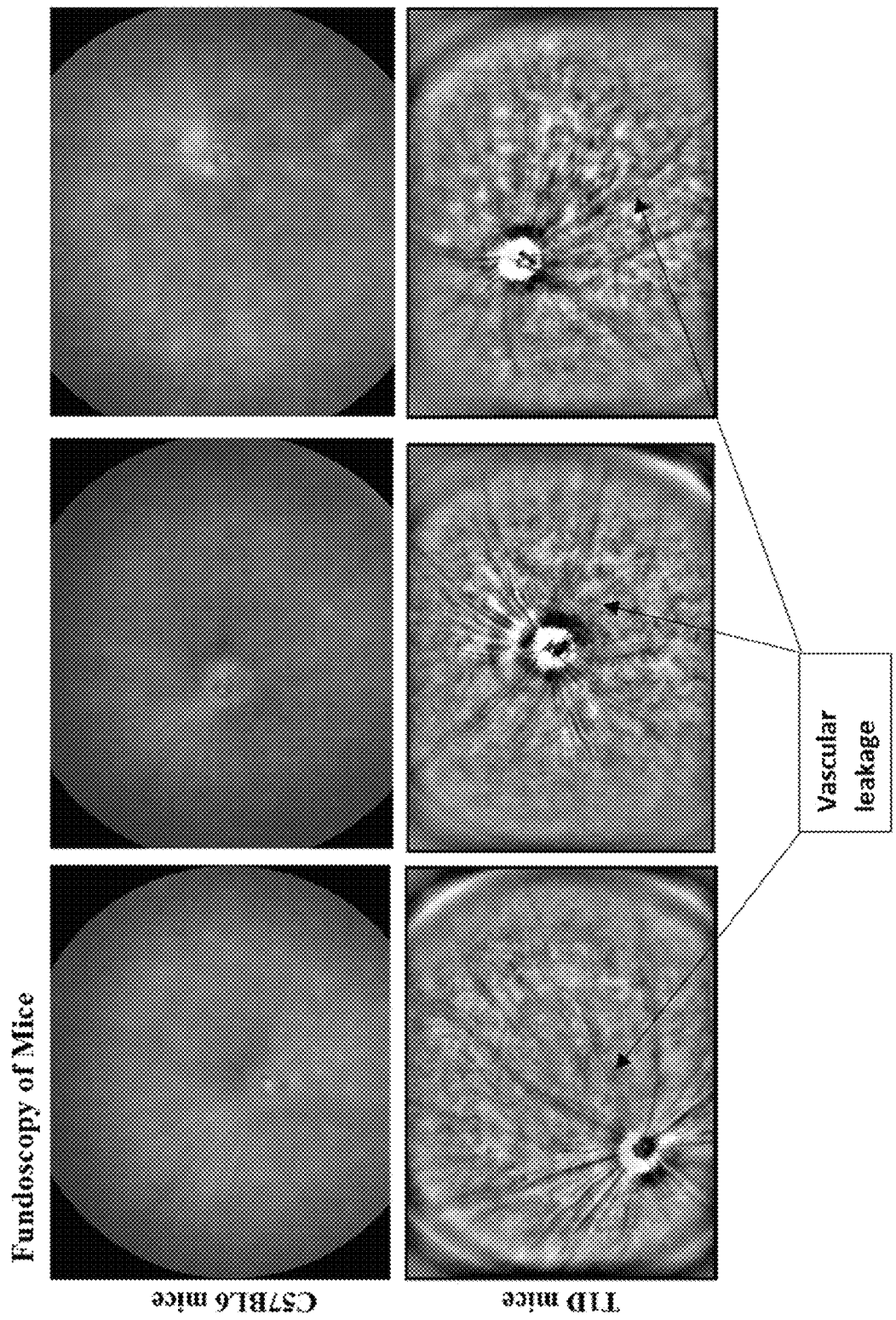
FIG. 12A: Fundoscopy for C57BL6 mice (top); and, T1D mice (bottom) showing leakage where chronic hyperglycemic condition leads to microvascular dysfunction and cause capillary leakage of the eye.

Mouse Retinal Vasculature:

FIG. 12A shows fundoscopy of mice, where vascular leakage is seen in the T1D transgenic mice but not the C57BL/6 control mice. Diabetes associated early vascular damage of retina characterize by the formation of acellular capillaries and induction of vascular cell apoptosis is known to happen in human diabetic opththalmopathy. Comparison of retinal vascular densities by trypsin-digested preparation of retinas from T1D mice and C57BL/6 (control) mice was performed. A representative figure of retinal trypsin digestion from T1D mice and C57BL/6 mice. A significant increase in cellularity and capillary loops in retinas of T1D mice as compared to C57BL/6 was observed.

Figure 12B:
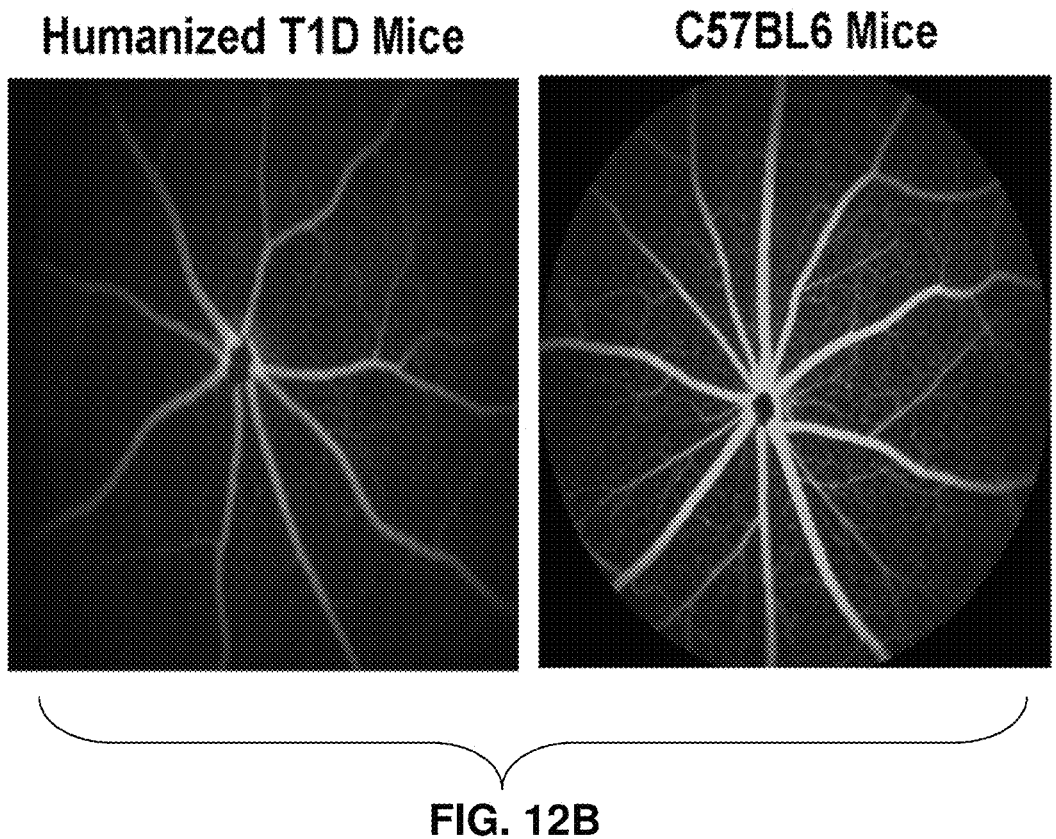
FIG. 12B: Fundus IR and auto fluorescence images were analyzed for vessel and optic nerve leakage by a blinded observer (n=8).
Figure 12C:
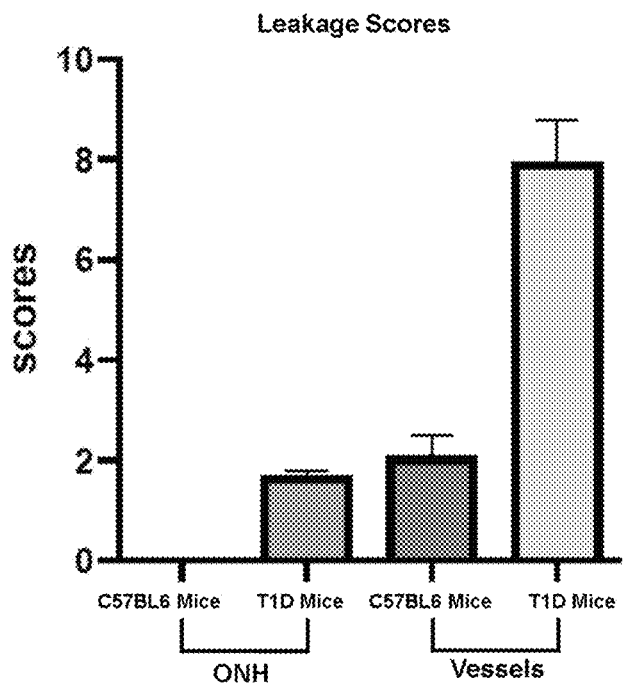
FIG. 12C: Vessels leakage scores were the sum of the four quadrants of each image per animal.

Fundoscopy of Diabetic Mice:

Chronic hyperglycemia cause vascular dysfunction and capillary leakage of eye as evident by fundoscopy of diabetic mice (FIG. 12A and FIG. 12B). Auto fluorescence images of the mouse eyes showed significant difference on optic nerve head and vessel leakage when compared to control C57BL/6 mice (FIG. 12C). Hard exudate and hemorrhage were also noted in the fundoscopy of T1D diabetic mice.

Figure 13A:
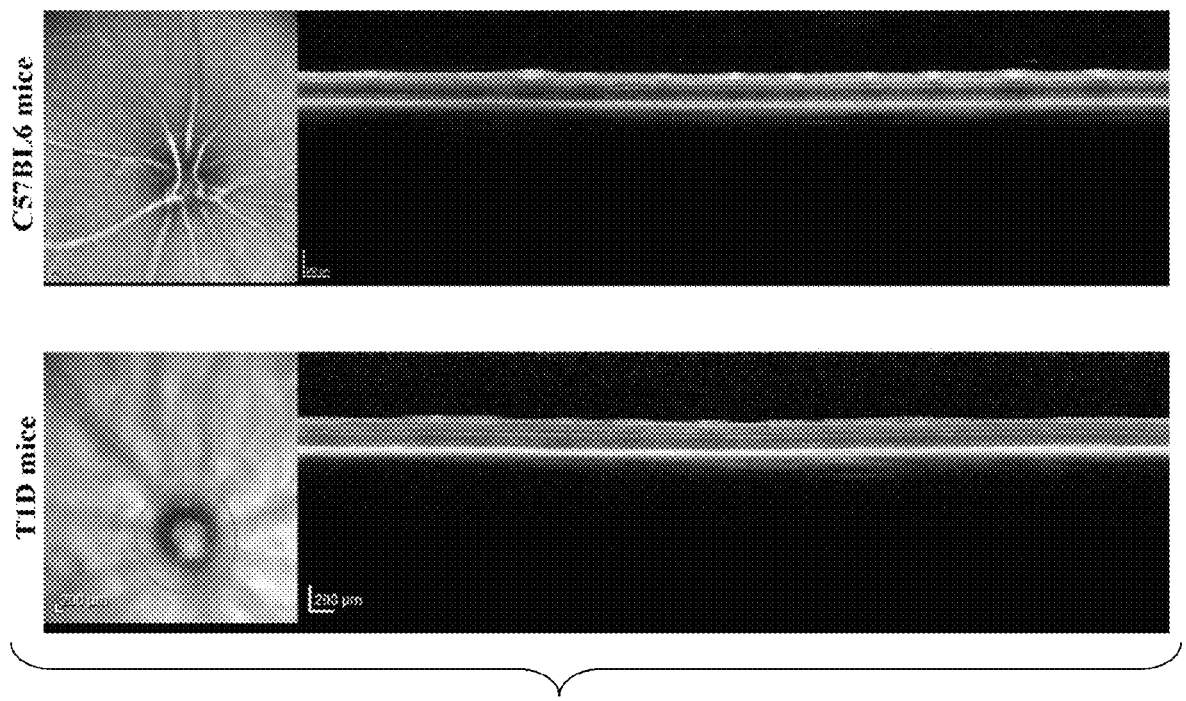
FIG. 13A: Quantification of retinal layer thicknesses in mice as seen on optical coherence tomography (OCT) for C57BL6 mice (top) and T1D mice (bottom). OCT images were taken and the inner retina (ganglion, amacrine and bipolar cells) and outer retina (photoreceptors: rods and cones) thickness was measured superior and inferior to the optic nerve head in C57BL6 (control) and T1D mice (n=8) (Image J software, analyzed using an unpaired t-test p<0.05).
Figure 13B:
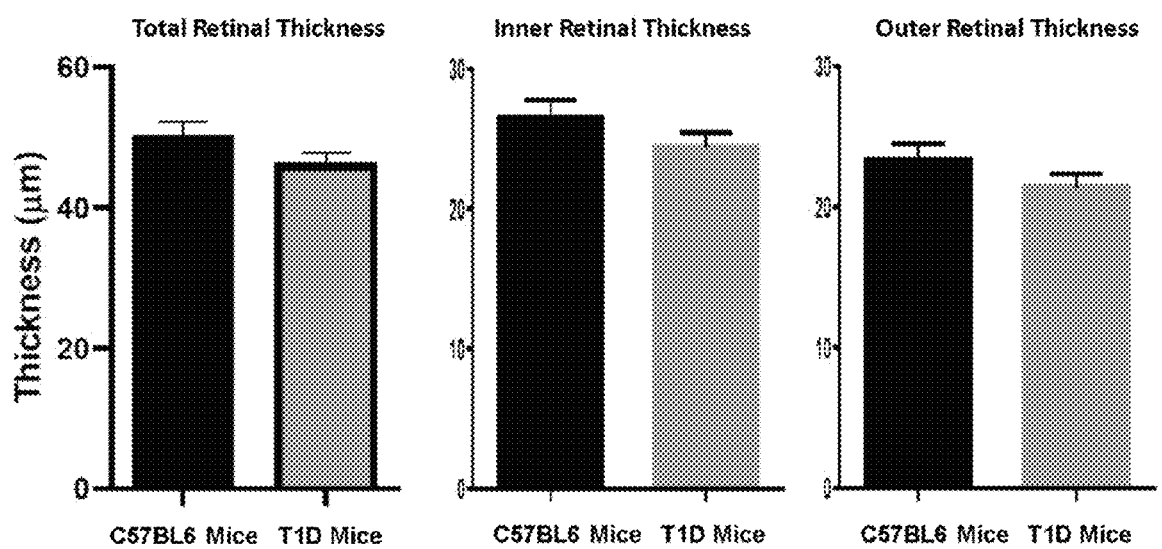
FIG. 13B: Retinal thicknesses for C56BL/6 mice and T1D mice: Total (left); Inner (middle), and Outer (right).

Optical Coherence Tomography (OCT) of Diabetic Mice:

Optical Coherence Tomography (OCT) is often used to evaluate disorders of the optic nerve as well as to see each of the retina's distinctive layers. OCT allows to map and measure their thickness. These measurements help with diagnosis of diseases of the retina and diabetic eye disease. OCT data revealed that T1D mice have comparatively lower total retinal thickness, inner and outer retinal thickness (FIG. 13A, FIG. 13B) for C57BL6 mice (top) and T1D mice (bottom). OCT images were taken and the inner retina (ganglion, amacrine and bipolar cells) and outer retina (photoreceptors; rods and cones) thickness was measured superior and inferior to the optic nerve head in C57BL6 (control) and T1D mice (n=8) (Image J software) and analyzed using an unpaired t-test (p>0.05).

Diabetes Complications—Eye

FIG. 14 shows photomicrographs of trypsin-digested retinas stained with periodic acid-Schiff hematoxylin: Quantitative analysis of acellular capillaries counted per mm2 trypsin digested retinas. T 1D mice have a significantly higher number of acellular capillaries compared to C57BL6 (control). Accordingly, with the development of diabetic nephropathy, animals also developed diabetic retinopathy. Six-month-old animals had a significant increase of acellular capillaries in the retina as compared to controls.

Diabetic Neuropathy:

Ex Vivo Electrophysiology Study:

To evaluate whether there were any function changes in optic nerve (CNS) and sciatic nerves (PNS) in the transgenic mice in comparison to wild type mice, compound action potentials were measured in 32 optic nerves and 32 sciatic nerves from 16 C57BL/6 mice and 16 T1D transgenic mice. The electrophysiology results are shown in FIGS. 15A-15F. Electrophysiology experiment were conducted to explore the functional changes in optic nerve (CNS) and sciatic nerves (PNS) of humanized T1D Mice (n=16) as compared to C57BL6 (n=16).

Optic nerves (between the eye and the optic chiasm) and sciatic nerves were quickly excised from decapitated C57BL/6 and T1D mice. The optic or sciatic nerve was bathed with oxygenated (95% $O_2$ and 5% $CO_2$) Ringer's solution. The nerves were transferred to a recording chamber for simultaneous electrophysiological studies after 10 to 15 minutes recovery from the dissection.

Compound action potentials in 32 optic nerves and 32 sciatic nerves from 16 C57BL/6 mice and 16 T1D mice were measured. Amplitude of CAP, conduction velocity of CAP and recovery of second CAP was analyzed. In 5-6 months optic nerves of diabetic mice (n=8), the recovery curve of second action potential was shifted to the right in comparison to C57BL/6 mice (n=8), showing an increase in the refractory period of second CAP in diabetic optic over the C57BL/6 mice (p<0.05). This increase in refractory period for CAP in the diabetic optic nerve was consistent with the reduced conduction velocity in the diabetic over the C57BL/6 mice, as refractory period is typically inversely related to the conduction velocity.

Figures 15A, 15B, 15C, 15D, 15E, 15F:
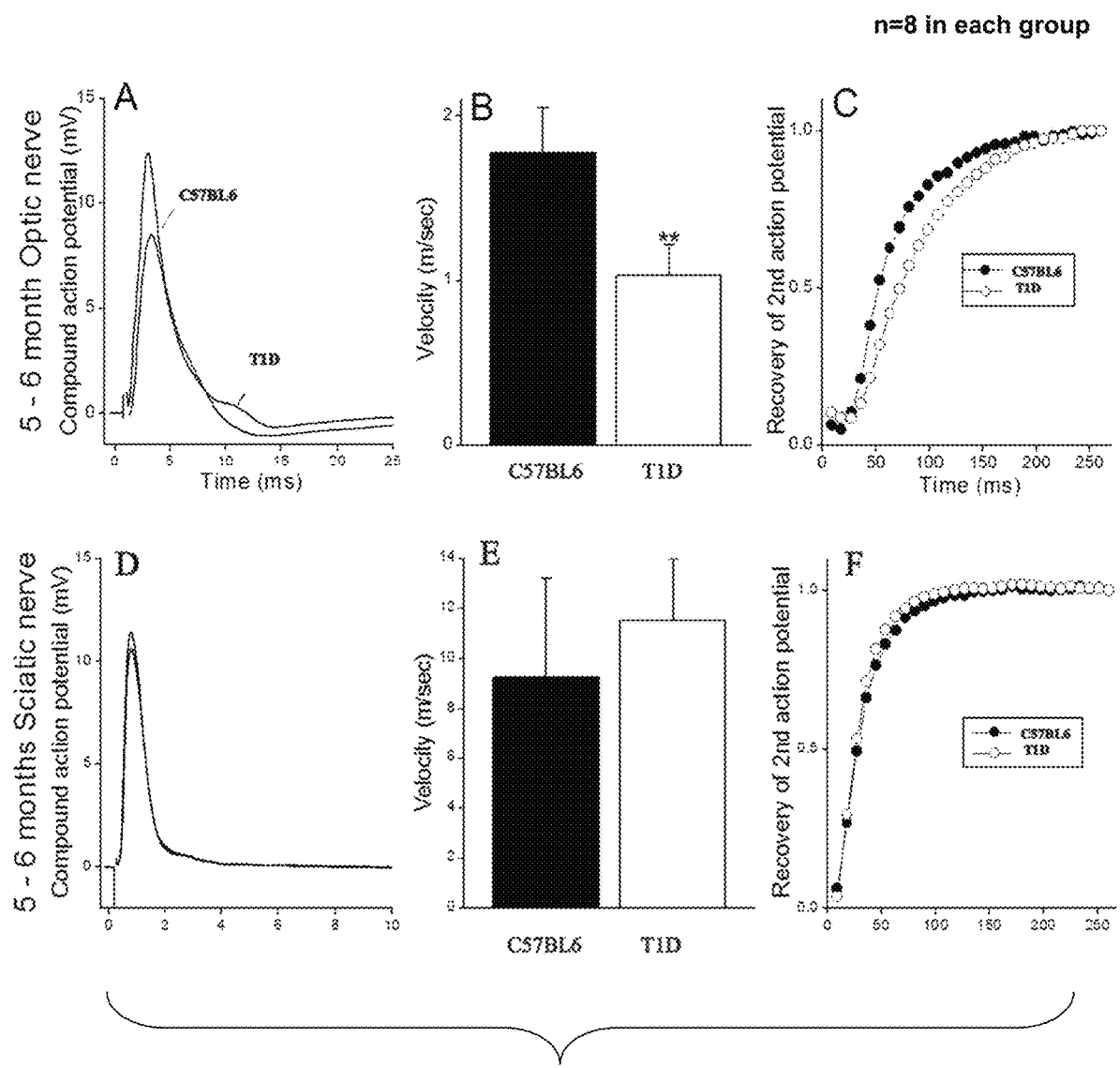
FIGS. 15A-15F: Electrophysiology—Compound action potentials in 32 optic nerves and 32 sciatic nerves were measured in 16 C57BL/6 control mice and 16 T1D diabetic mice.

Optic nerves (between the eye and the optic chiasm) and sciatic nerves were quickly excised from decapitated mice. The optic or sciatic nerve was bathed with oxygenated (95% O2 and 5% CO2) Ringer's solution. The nerves were transferred to a recording chamber for simultaneous electrophysiological studies after 10 to 15 minutes recovery from the dissection:

Compound action potentials (CAP) were recorded for analyzing conduction along optic nerves and sciatic nerves (FIG. 15A and FIG. 15D).

The conduction of nerves (velocity) was calculated by measuring the time between stimulation artifacts and the peaks of compound action potentials and the length of optic nerves and sciatic nerves (FIG. 15B and FIG. 15E).

The refractory period measures the period following the first stimulation in which a second stimulation, delivered at increasing time after the first stimulation, gradually allows a full recovery of the amplitude of the action potential. Note: Diabetic neuropathy reduces the neuronal conductivity of small nerves like optic nerve (CNS) (FIG. 15C and FIG. 15F).

Compound action potentials (CAP) were recorded for analyzing conduction along optic nerves (FIG. 15A) and sciatic nerves (FIG. 15D).

The conduction of nerves (velocity) was calculated by measuring the time between stimulation artifacts and the peaks of compound action potentials and the length of optic nerves (FIG. 15B) and sciatic nerves (sciatic nerves (FIG. 15E).

The refractory period measures the period following the first stimulation in which a second stimulation, delivered at increasing time after the first stimulation, gradually allows a full recovery of the amplitude of the action potential for optic nerves (FIG. 15C) and sciatic nerves (sciatic nerves (FIG. 15F). Note that diabetic neuropathy reduces the neuronal conductivity of small nerves like optic nerve (CNS).

Discussion

Presentation of primary target antigen(s) in the context of diabetes susceptibility HLA genes is an important component of the pathogenesis of the autoimmune diabetes. An animal model of T1D, in which primary human β-cell autoantigen(s) are presented to effector cells in the context of human MHC-class II diabetes susceptibility genes, is described in this example and is useful for studies of molecular mechanisms of disease and for testing antigen specific immune-therapies applicable to humans.

This example describes the generation of mice that express high levels of hGAD65 in β-cells and at the same time have their endogenous mouse MHC-class II antigens replaced by the human HLA-DQ8 diabetes susceptibility locus.

Animals in the C57BL/6 background did not spontaneously develop diabetes. C57BL/6 may be best described as a strain of low diabetes susceptibility. Despite the decreased insulin secretion seen in elder C57BL/6 mice, this line is relatively resistant to, for example, obesity-induced diabetes. The BTBR strain appears to have a relative deficiency of β cell neogenesis. When obese, these mice develop diabetes. By contrast, C57BL/6 mice are able to compensate for the obesity-induced insulin resistance by increasing pancreatic insulin secretion and thus maintain only slightly elevated plasma glucose levels.

The spontaneous diabetes model described in this example manifested hyperglycemia after 30 generations of breeding selection based on high fasting blood glucose. Animals not only developed autoimmune diabetes as indicated by the presence of islet lymphocytic infiltration and development of target autoantigen antibodies, but also acquired all the microvascular complications typical of human diabetes.

While the mechanisms involved in progression from insulitis to insulin dependent diabetes are not currently known, the model is useful for testing factors implicated in human diabetes, including, but not limited to, upregulation of MHC class I antigens, and/or interferons, or associations with viral infections. Furthermore, the model is the closest one to human diabetes and is not just suitable for therapies to halt or hinder diabetes and its development but also to address diabetes complications.

Example III

Multi-omics Modeling of the Gut Microbiome and Host Response in the Progression of Type I Diabetes Type 1 Diabetes (T1D) is defined as the autoimmune destruction of pancreatic islet cells, and generally occurs within the first few years of development. In human, the time between islet destruction to the earliest appearance of a first islet autoantibody is between 9-36 months, which indicate that β-cells destruction may take month or years before manifestation of the first autoantibody. The human intestinal system has a complex community of microbes (microbiome) shaped during the first few years of life. Early development of gut microbiota in early life is crucial, and has a limited resilience and is vulnerable to perturbation, whereas the microbiota of adults is resilient and most strains in an individual's intestine are residents for decades. It is estimated that in T1D, pancreatic β-cells destruction occurs at least five years prior to onset of clinical disease. T1D diagnosis is made only when more than 80% of the β-cells have been lost. In the last five decades the incidence of T1D increased by fivefold. The incidence of T1D is slightly higher in boys as compared to girls and its male to female ratio is 3:2. Children who progress to clinical T1D before puberty have detectable levels of islet specific autoantibodies before age three.

The humanized transgenic mice model of T1D, spontaneously develop diabetes. This mouse model mimics clinical human T1D, was used to carry out phase 1 controlled studies to investigate diabetes development and gut microbiota after normal weaning (NW) and late weaning (LW) stages. The data revealed that the gut microbiota changes as weaning is delayed, and that disease progression correlates with these changes.

It is now believed that to halt T1D or delay its progression, enrichment of regulatory T (Treg) cells secondary to increased diversity of gut microbiome may be induced with prolonged nursing. This was tested by setting up experiments where the breeder's cages with larger litter sizes (8 pups) were separated in two groups. The breeder mice were allowed a second time pregnancy, and after birth, the second litters were sacrificed and the first litters (late weaning group, LW) were allowed to stay with their mothers until day 45. Normal weaning (NW) group were separated at day 21. At day 60 and 150, mice from both groups (n=10-12) were sacrificed. Organs (Peyer's patches (PP), peri-pancreatic lymph nodes (PLN), pancreas (PN) and spleen) were harvested and lymphocytes isolated.

Flow cytometry of Peyer's patches, a site of first immune cell interaction/activation with gut antigens, revealed that Tregs were significantly increased in the late weaning group. Flow cytometry data revealed that late weaning leads to enrichment of Tregs and consequently regulate cytotoxic CD8 T lymphocytes (CTLs) at PLN, a site for islet antigen-specific T cell activation and recruitment in T1D. Most interestingly, late weaning enriched the Treg population at the spleen level too.

The enrichment of Tregs may have been due to a more diverse microbiome, which is known to increase immune tolerance, which might have regulated the diabetogenic Th1, Th17 and CTLs at PLN, PN and spleen. Our data is the first to provide a scientific explanation for the observed prolonged nursing effect in T1D outcomes in humans.

Also investigated was the possibility that induction of immune tolerance would protect pancreatic islet architecture. Pancreatic sections were stained with hematoxylin/eosin (H&E) for histological identification and localization of islets and lymphocytic infiltrates. Prolonged nursing, preserved the pancreatic islet architecture with fewer lymphocytic infiltrates and significantly higher number of islet per H&E section in LW group.

Results

Figure 16A:
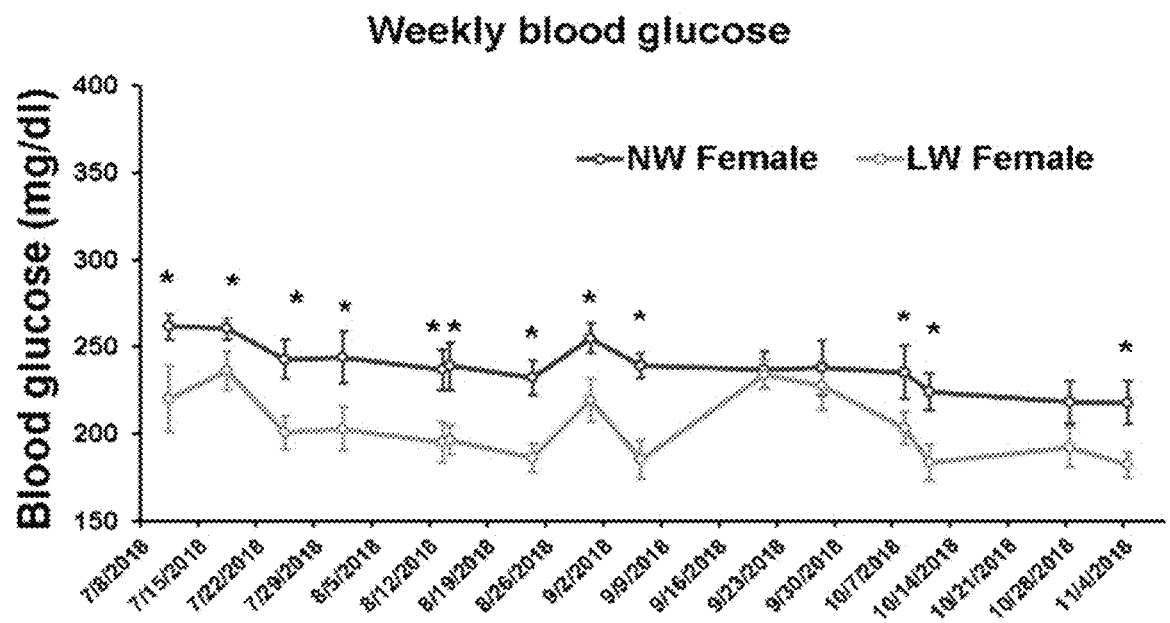
FIGS. 16A-16E: Weekly fasting glycaemia and weight monitoring. A significant glycemic differences were noted between normal weaning (NW) and late weaning (NW) group at several points (n=10-12) (FIG. 16A, FIG. 16B); whereas, no significant differences were noted in weekly body weight (FIG. 16C, FIG. 16D) (n=8). Bar graph of mice humoral immune response (anti-GAD65 Antibody production) (n=10-12) (FIG. 16E). Statistical significance was determined at P<0.05. Lowercase letters (a-d) identify significant differences among the groups. Means with different superscript (*) have a significance difference (p<0.05) among the groups.
Figure 16B:
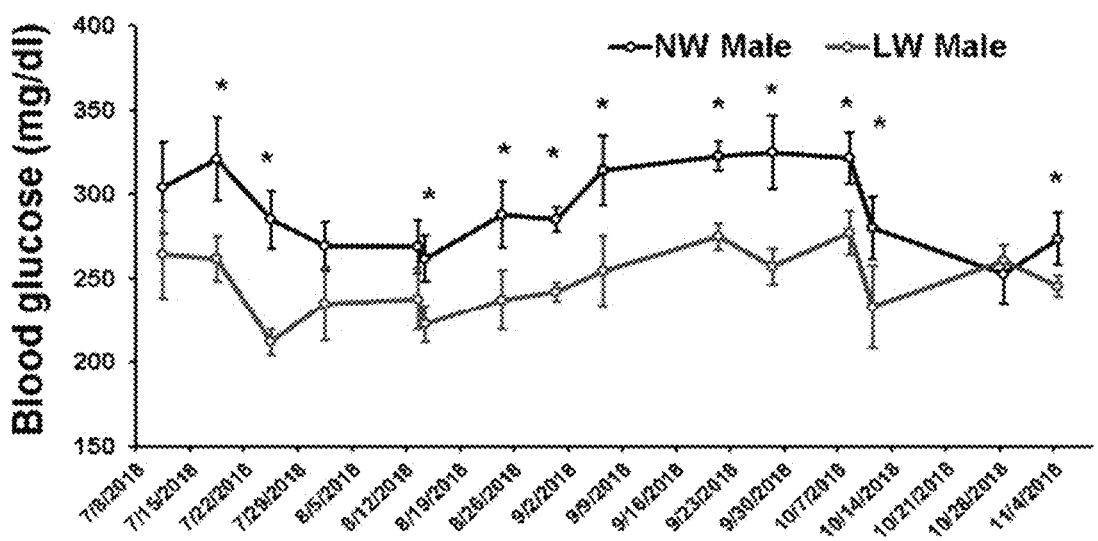
Figure 16C:
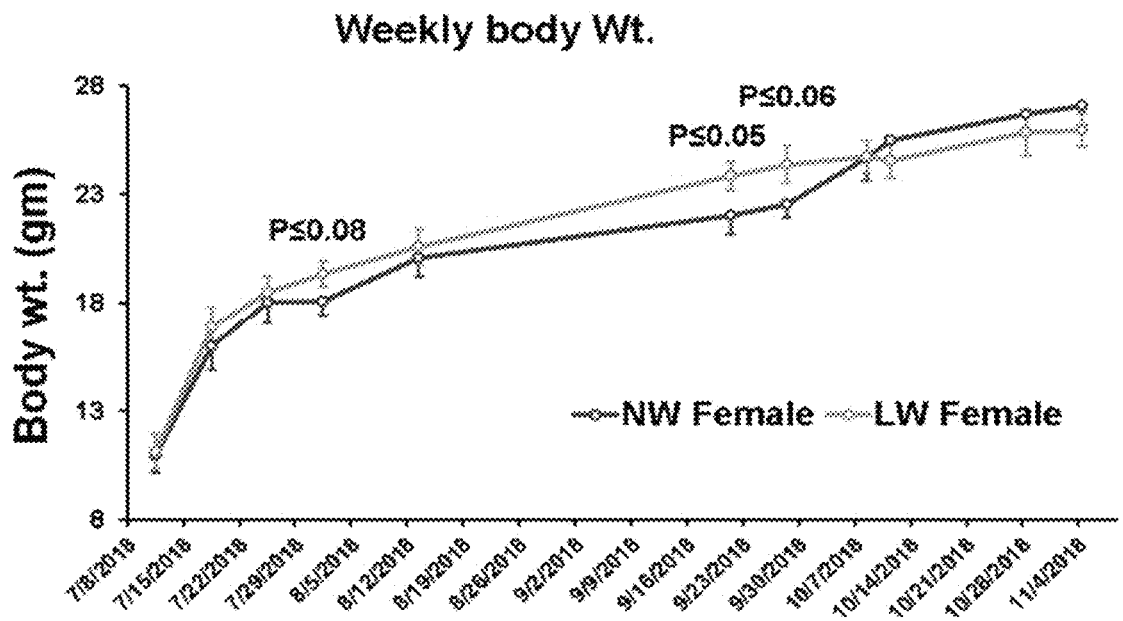
Figure 16D:
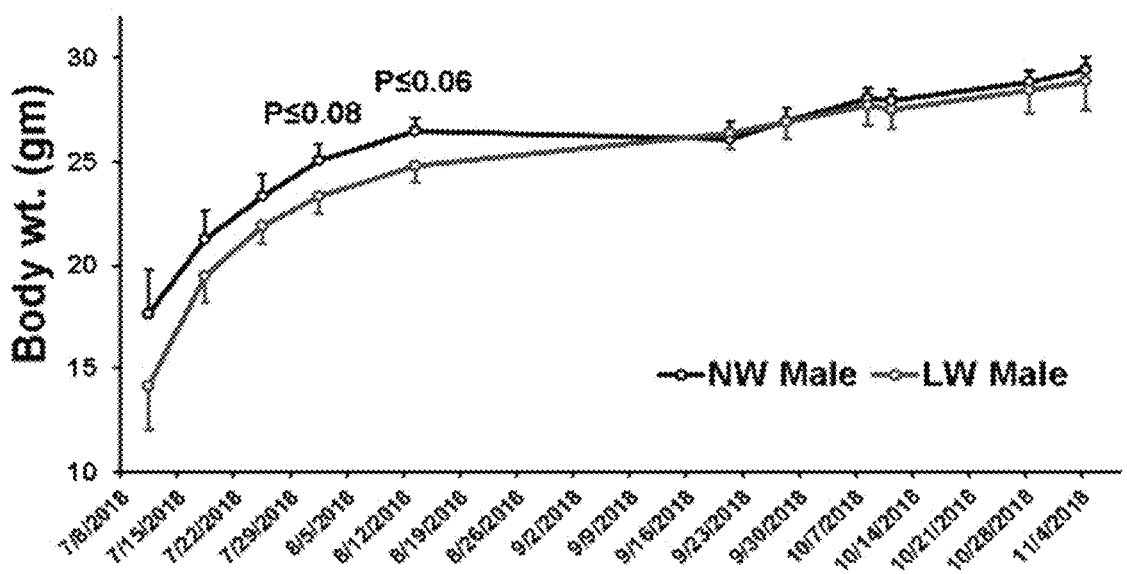
Figure 16E:
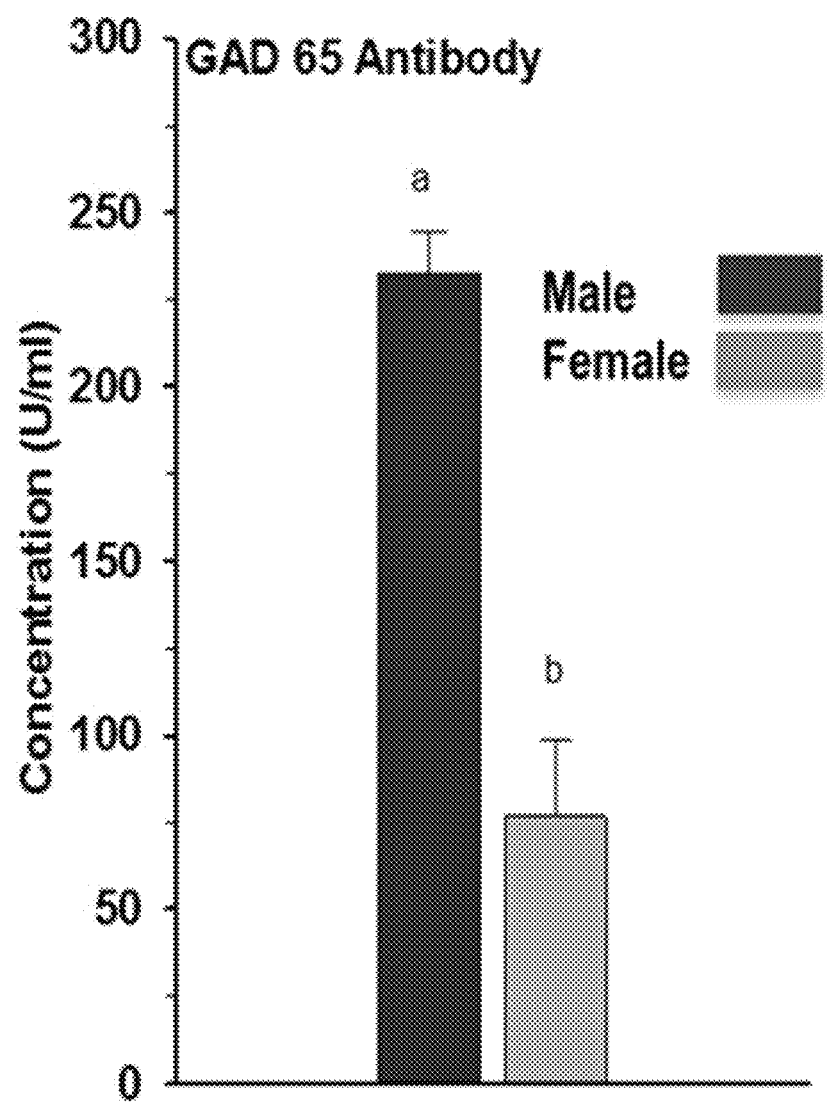

Weekly fasting glycaemia and weight monitoring. A significant glycemic differences were noted between normal weaning (NW) and late weaning (NW) group at several points (n=10-12) (FIG. 16A, FIG. 16B). Whereas, no significant differences were noted in weekly body weight (FIG. 16C, FIG. 16D) (n=8). Bar graph of mice humoral immune response (anti-GAD65 Antibody production) (n=10-12) (FIG. 16E) were also measured.

Figure 17A:
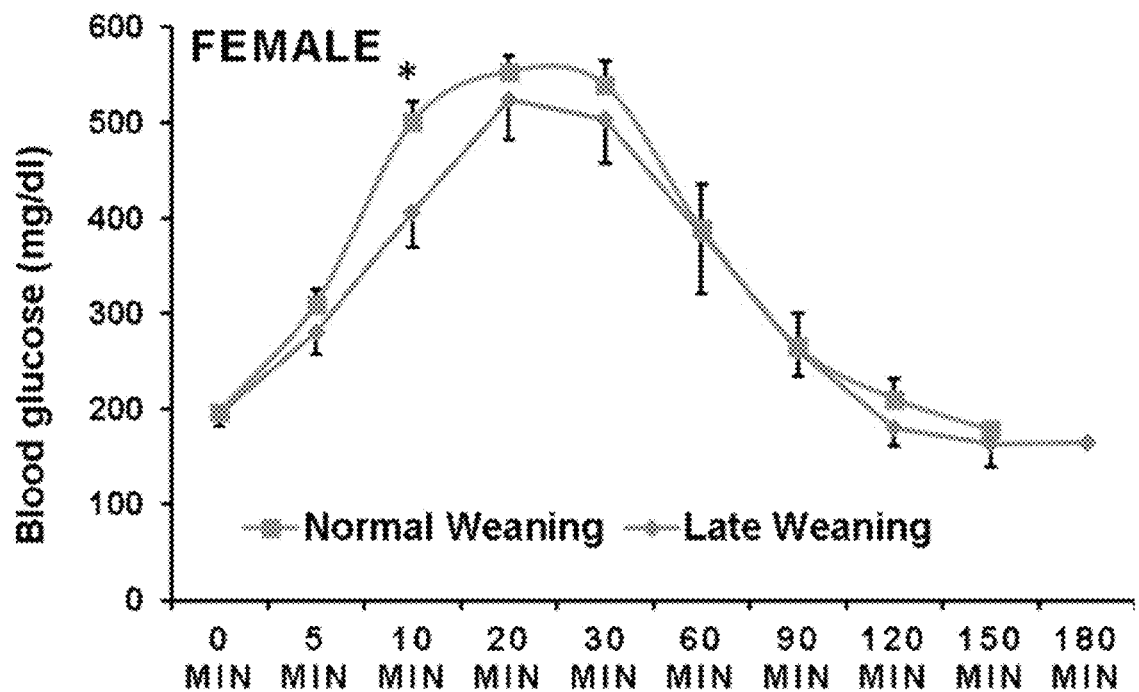
FIG. 17A: Glucose tolerance test (GTT) in female at 60 days old mice (n=10-12) in normal weaning (NW) and late weaning (NW) group. Statistical significance was determined at P<0.05. Lowercase letters (a-d) identify significant differences among the groups. Means with different superscript (*) have a significance difference (p<0.05) among the groups.
Figure 17B:
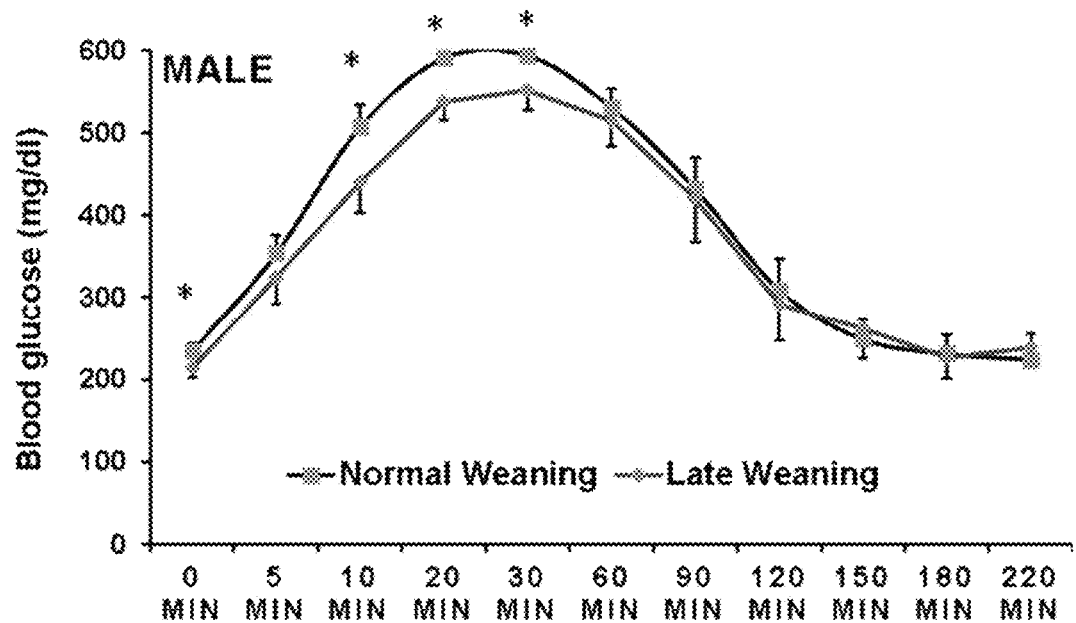
FIG. 17B: Glucose tolerance test (GTT) in male at 60 days old mice (n=10-12) in normal weaning (NW) and late weaning (NW) group. Statistical significance was determined at P<0.05. Lowercase letters (a-d) identify significant differences among the groups. Means with different superscript (*) have a significance difference (p<0.05) among the groups.

The progression of diabetes in LW and NW group of pups was investigated. Glucose tolerance test (GTT) on $60^{th}$ day revealed a significant difference at certain points in both male and female groups (FIG. 17A, FIG. 17B).

Figure 17C:
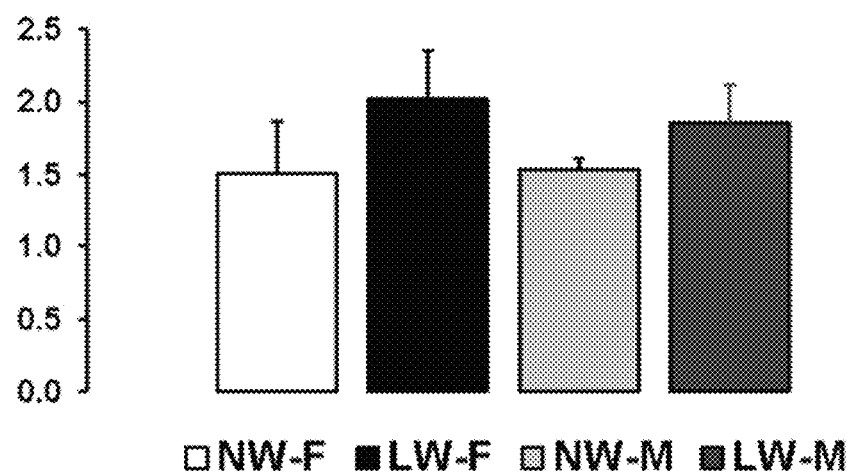
FIG. 17C: Fasting plasma insulin at 60 days old mice (n=10-12) in normal weaning (NW) and late weaning (NW) group. Statistical significance was determined at P<0.05. Lowercase letters (a-d) identify significant differences among the groups. Means with different superscript (*) have a significance difference (p<0.05) among the groups.

The GTT data were corresponding with fasting insulin secretion (FIG. 17C), fasting insulin secretion were higher in LW group of both gender. The effect of late weaning were consistent until $150^{th}$ day.

Figure 18A:
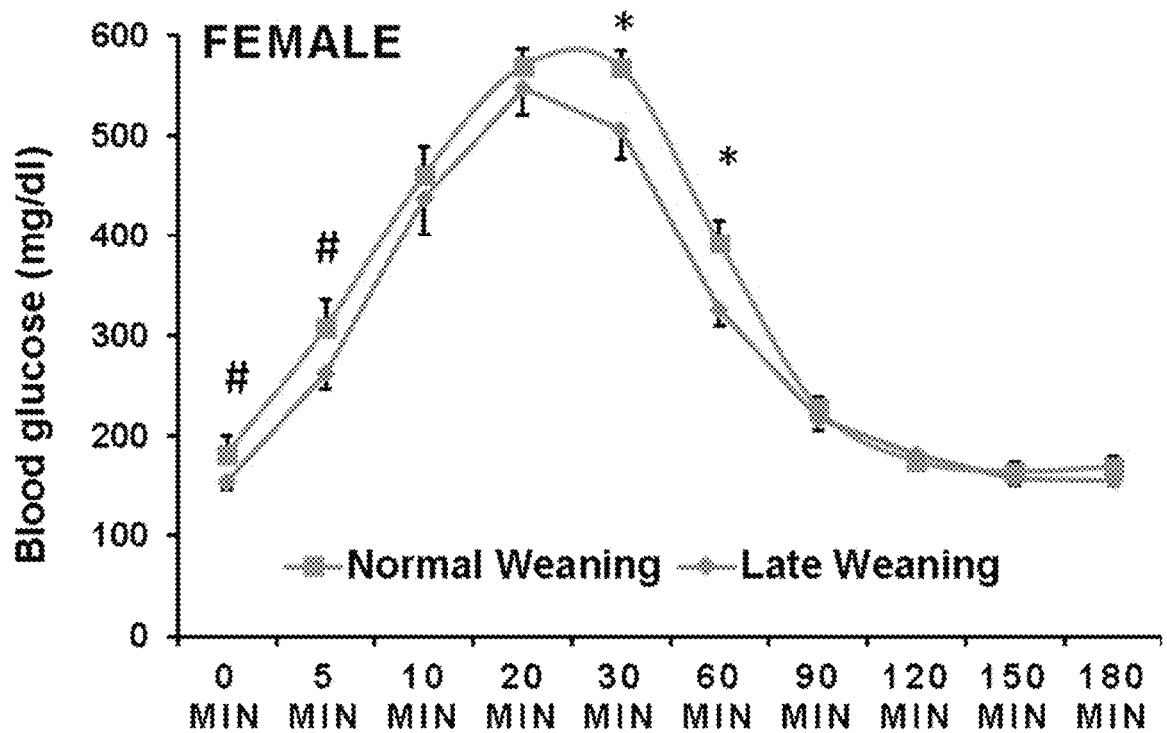
FIG. 18A: Glucose tolerance test (GTT) in female at 150 days old mice (n=10-12) in normal weaning (NW) and late weaning (NW) group. Statistical significance was determined at P<0.05. Lowercase letters (a-d) identify significant differences among the groups. Means with different superscript (*) have a significance difference (P<0.05) among the groups.
Figure 18B:
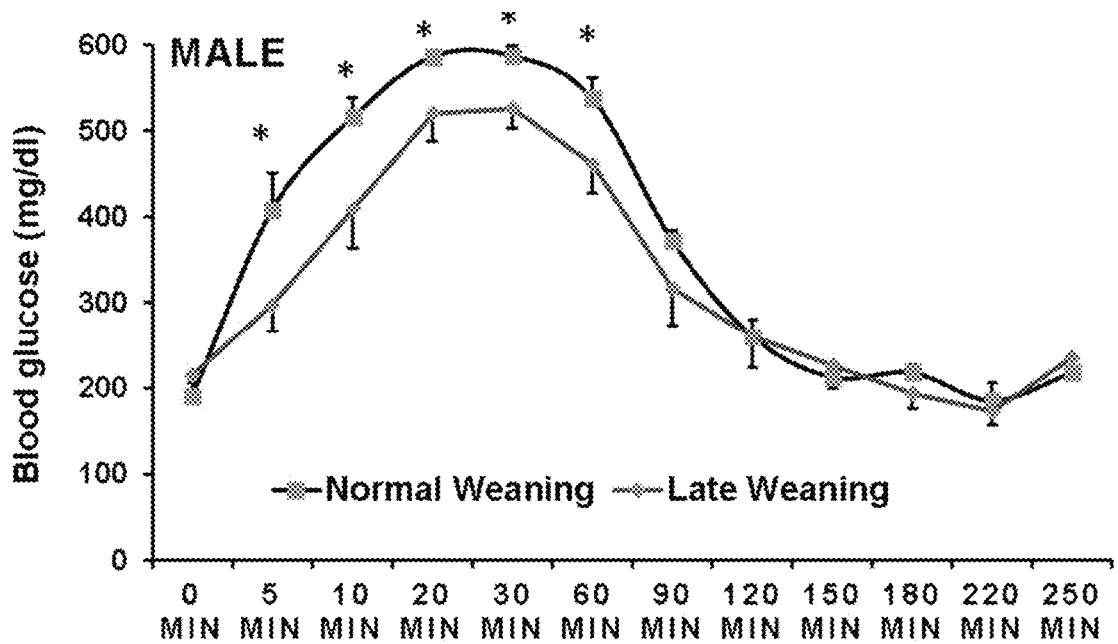
FIG. 18B: Glucose tolerance test (GTT) in male at 150 days old mice (n=10-12) in normal weaning (NW) and late weaning (NW) group. Statistical significance was determined at P<0.05. Lowercase letters (a-d) identify significant differences among the groups. Means with different superscript (*) have a significance difference (P<0.05) among the groups.
Figure 18C:
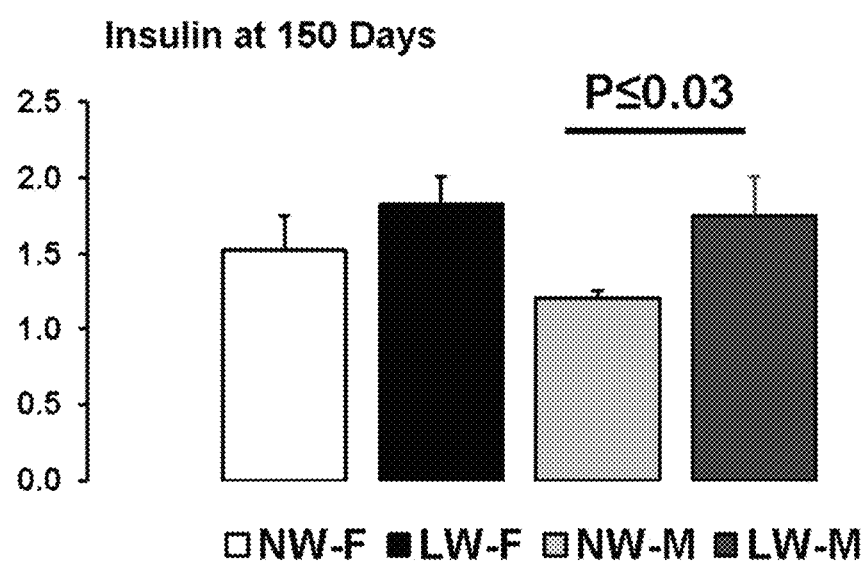
FIG. 18C: Fasting plasma insulin at 150 days old mice (n=10-12) in normal weaning (NW) and late weaning (NW) group. Statistical significance was determined at P<0.05. Lowercase letters (a-d) identify significant differences among the groups. Means with different superscript (*) have a significance difference (P<0.05) among the groups.

Glucose tolerance (GTT) on $150^{th}$ day revealed certain significant difference up to 60 mints post glucose challenge, the effect were more prominent in male as compared to female (FIG. 18A, FIG. 18B), fasting insulin secretion were also higher in LW group and was significantly higher in male (FIG. 18C).

Example IV

Prolonged Nursing (Late Weaning) Delays the Onset of Type 1 Diabetes in the Genetic Susceptible Humanized Mouse Model of T1D Materials and Methods The T1D mouse model described in Example I above was used in this example. Fecal pellets were collected in late and normally weaned pups. Bacterial profiling of fecal samples was conducted using 65 rRNA gene sequencing. An operational taxonime unit was normalized prior to beta diversity analyses. Principal coordinates analysis plots and ANOSIM tests for significance were made with a weighted unifract distance matrix. Linear discriminant analysis effect size (LEfSe) was used to identify the longitudinal progression of the microbiome during the onset and progression of T1D. Alpha diversity indices, and PD Whole Tree were generated from OUT table. Spearman rank correlations were performed.

Results

Figure 19:
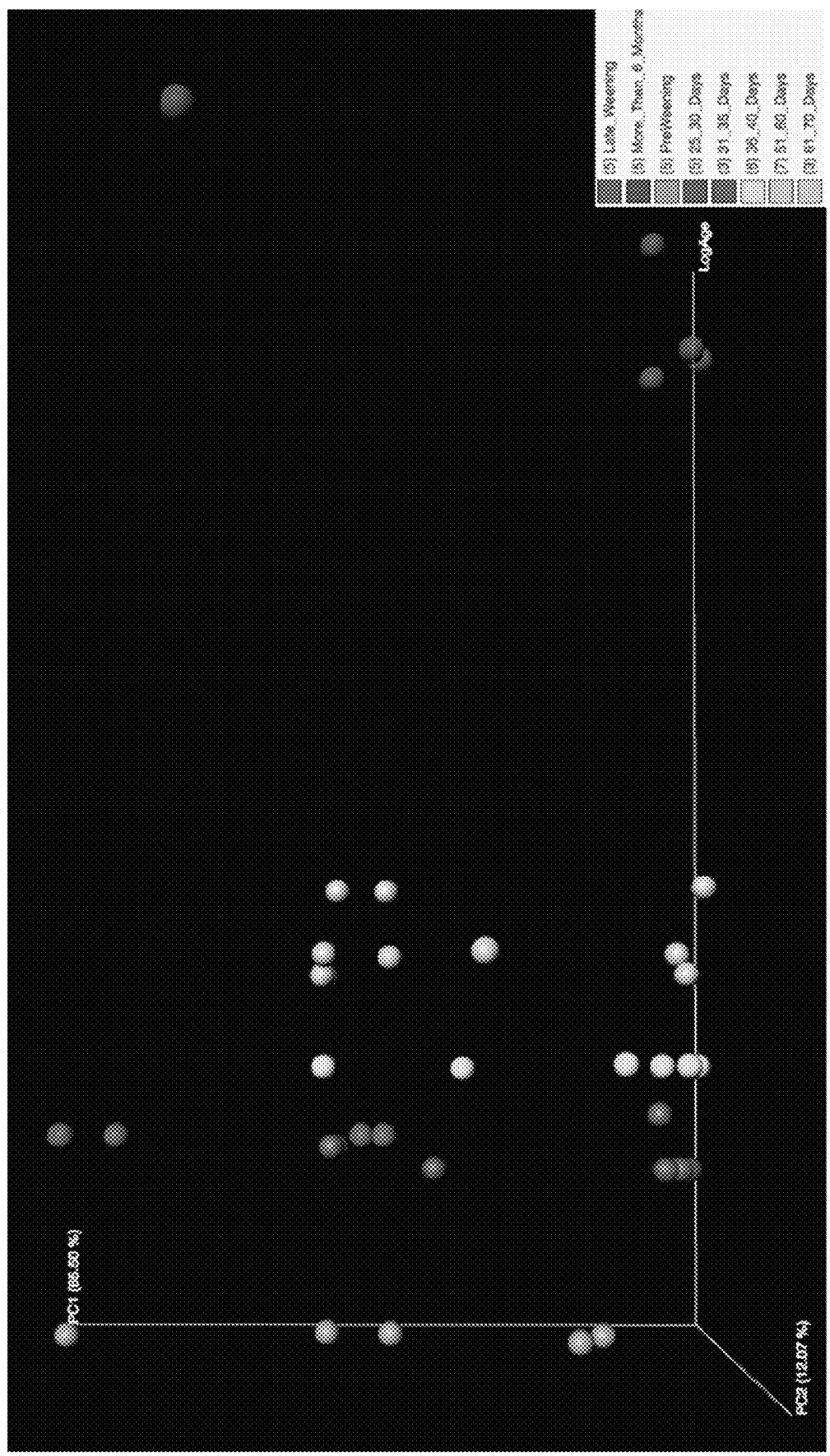
FIG. 19: Shows directional principal coordinates analysis plot to visualize trends in beta diversity of fecal bacterial communities from different age T1D mice. Plot was generated from the weighted UNIFRAC distance matrix within the QIIME pipeline.

Animals who weaned at the normal time had an aggressive diabetes development as compared to late-weaning mice (FIG. 16A and B). Principal coordinates analysis (FIG. 19) demonstrated a consistent and distinct bacterial community structure stratified by age, indicating a distinct microbial gut ecology common to the progression of T1D. Reduced abundance of butyrate producers, and an increase in members of the Bacteroidetes, Anaeoroplasma, and Ruminococcaceae, specifically the Oscillospira, which has been correlated with impaired gut epithelial barrier function, were observed (FIG. 20D).

Figure 20A:
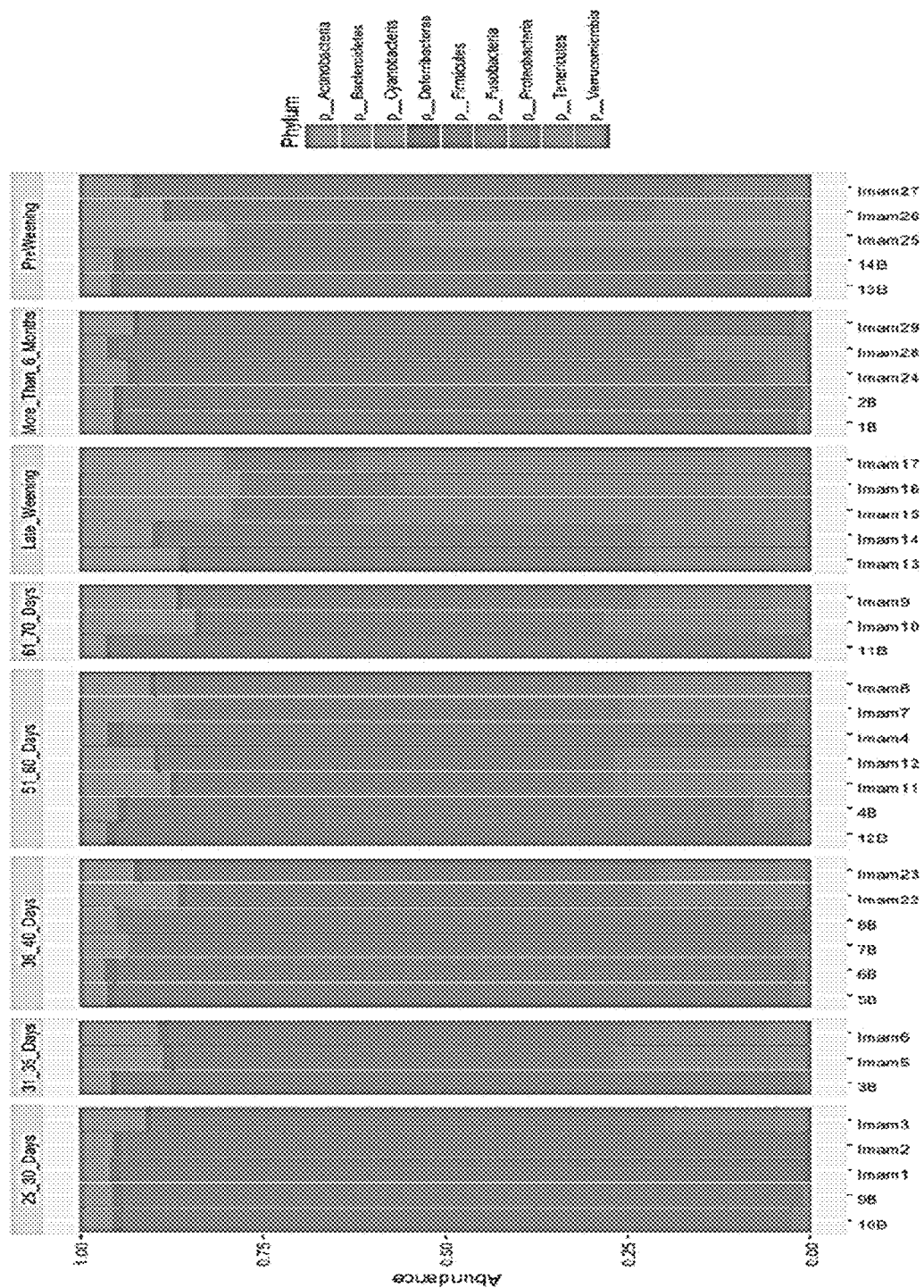
FIG. 20A: Shows phylum level summaries reveal differences in the general microbial community composition of fecal samples grouped by age. Here, a distinct difference is seen in the late weaning cohort in comparison to the remaining sample groupings, with elevated relative abundances of proteobacteria, cyanobacteria, and fusobacteria when compared to the remaining cohorts, which are dominated by firmictues.
Figure 20B:
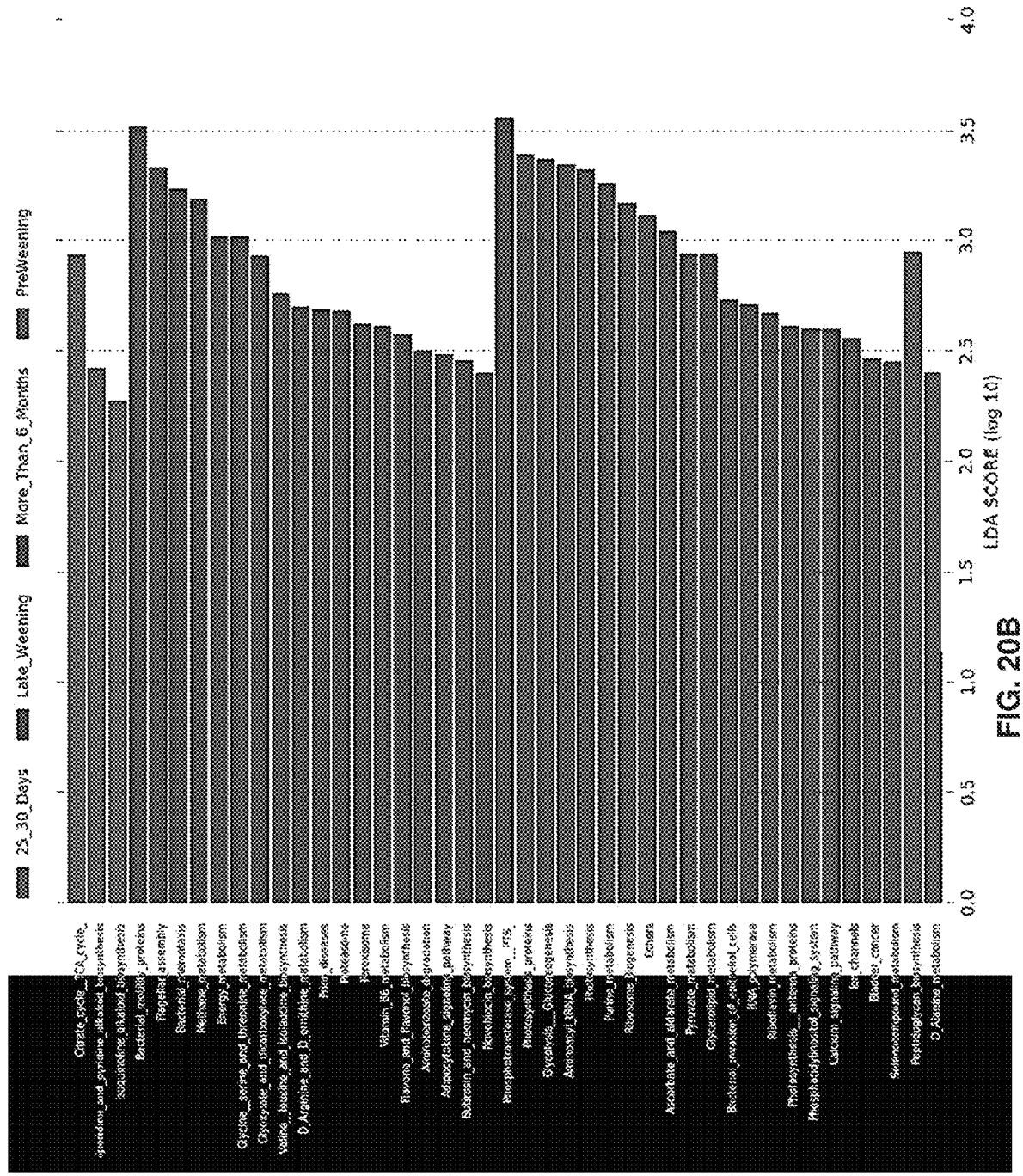
FIG. 20B: Shows LefSE plot generated to display enriched predicted metabolic functions within each respective cohort. The figure displays all functions found to be significantly (p<0.05, LDA>2.0) enriched within each sample cohort. The Y-axis displays each respective enriched function, whereas the X-axis displays the corresponding LDA enrichment score, which quantifies the strength of enrichment within each respective cohort (separated by color).
Figure 20C:
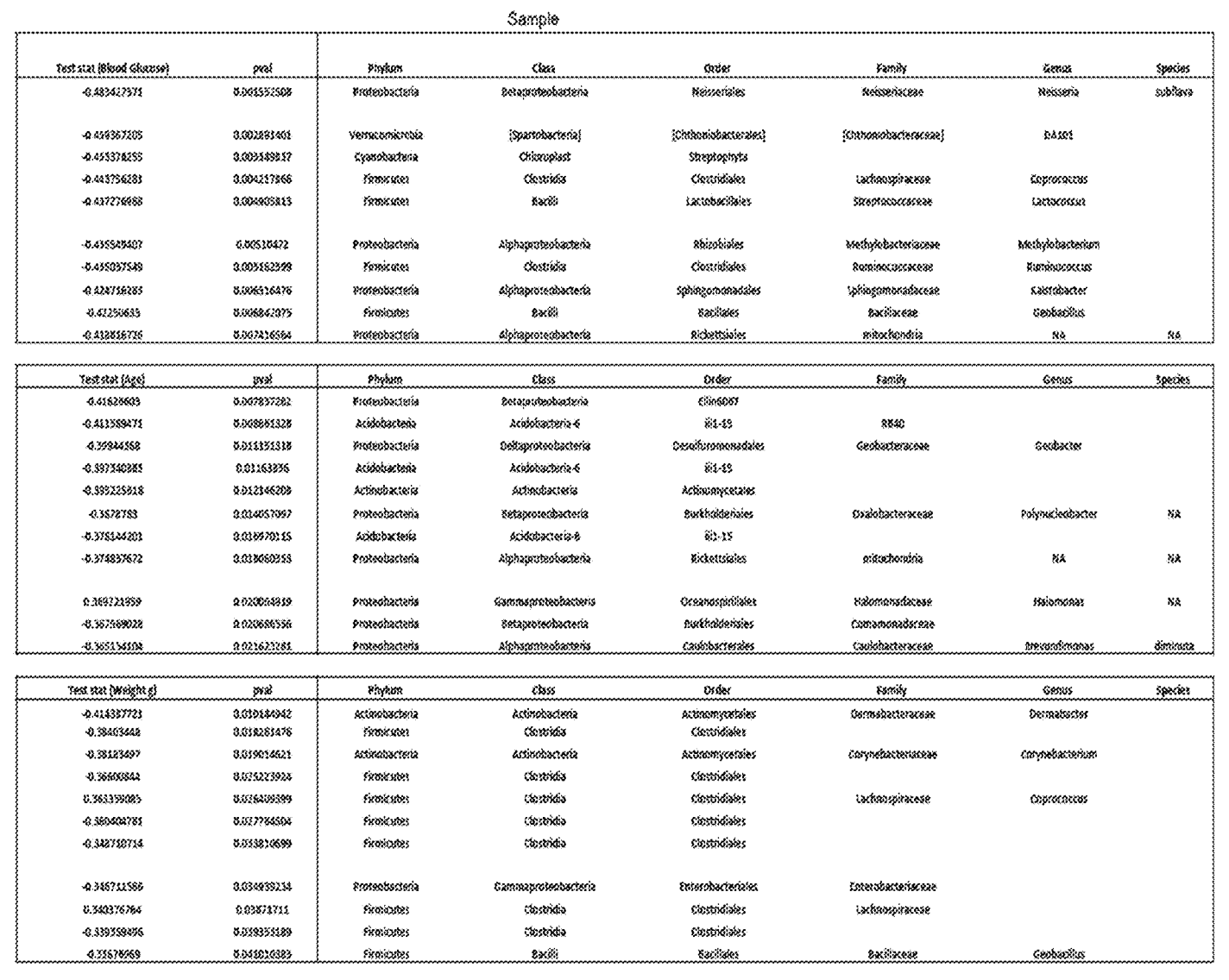
Figure 20D:
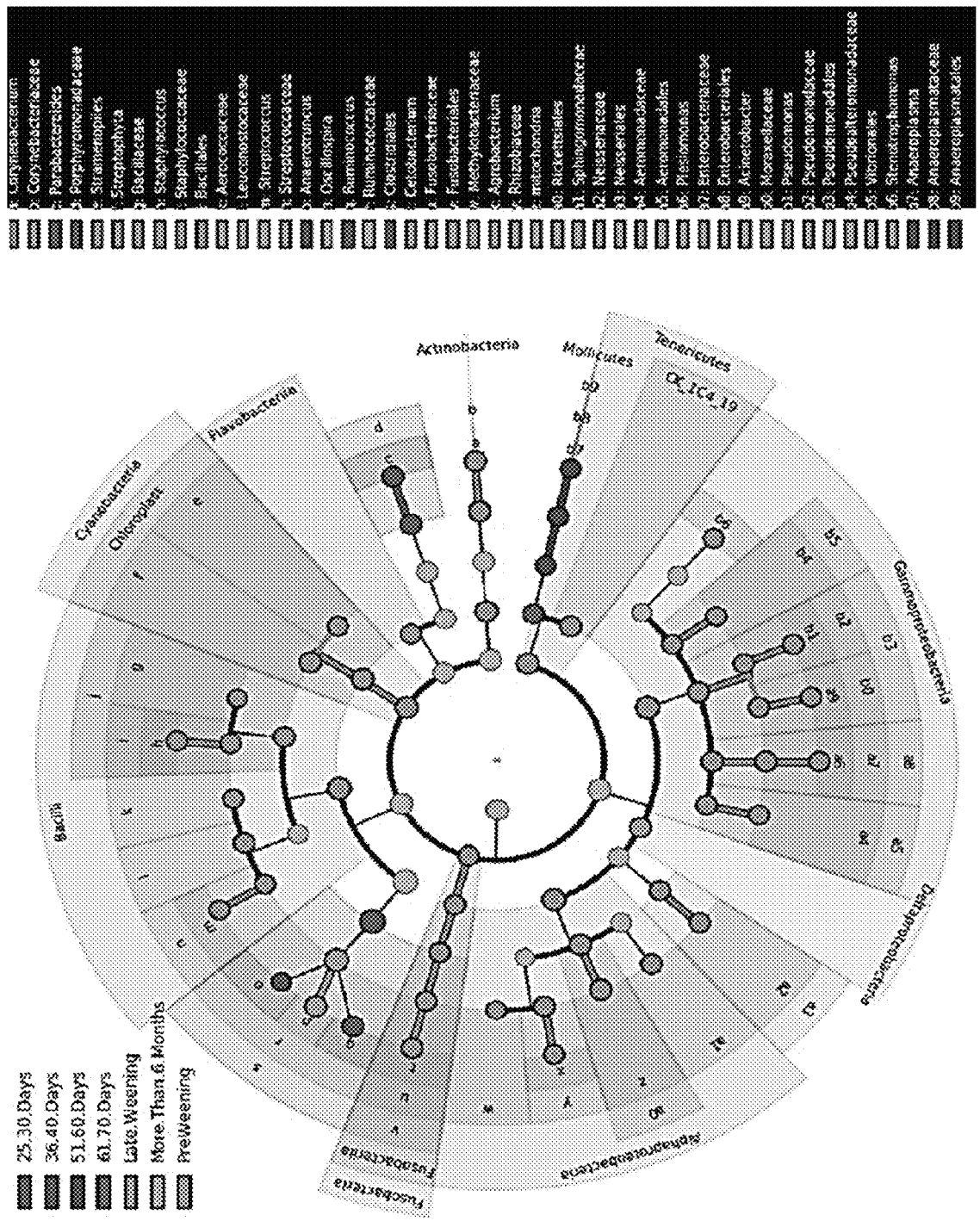
FIG. 20D: Shows a cladogram generated using the Galaxy platform presents significantly (Kruskal Wallis & Wilcoxon correction p<0.05, LDA>3.0) enriched bacterial taxa identified within each group. Taxonomy is organized in a tree formation with the kingdom "Bacteria" serving as the central root. As indicated by the phyla summaries, the late weaning cohort yields a unique microbial community composition, with a total of 44 significantly enriched taxa. Therefore, as in humans, delayed weaning (nursing) in these diabetes genetically susceptible mice has a substantial impact on the microbiome.

Interestingly, high-throughput sequencing of 16S rRNA gene revealed that late weaning litters have an enriched bacterial diversity as compared to the normal weaning group (FIG. 20D). There were a total of 46 distinct taxa from Tenericutes, Fusobacteria, Bacilli, Proteobacteria, and others that were significantly enriched in the later weaning samples as compared to the normal weaning group (FIGS. 20A, 20D).

Additionally, the predicted microbial gene content was calculated, and showed several metabolic pathways that are enriched within different time point samples (FIG. 20B). Impressively, more than 20 metabolic pathways were enriched in the late weaning microbiome samples, including a variety of amino acid biosynthetic pathways, signaling pathways, and ion transport, indicating that these pathways may be involved in promoting a healthy or eubiotic gut environment that could delay disease onset/progression. This functional analysis demonstrates that unique metabolic signatures within the gut microbiome may underlay the different stages of type 1 diabetes onset and progression.

The data from the normal weaning and late weaning groups indicate that the dynamic changes in gut microbiome are responsive to initial pathophysiological changes in the host. While the microbial communities converge at later time point samples (6 months), this enrichment in the microbial community was captured in the late weaning group. This dynamic change in the bacterial community mirrors the observed lower glucose levels in the late weaning population and indicates that the microbiome may play a role in at least delaying the onset/progression of T1D in the humanized mouse model.

Discussion

During the first three years of life, the gut microbiota undergoes a dynamic change in taxonomic diversity, and this is also a time during which T1D disease progression is initiated. Development of gut microbiota in early life is important, and this microbiota has a limited resilience and is vulnerable to perturbation, whereas the microbiota of adults is resilient. The WHO has recommended that infants be breastfed exclusively until six months of age, with breast feeding continuing as an important part of the infant's diet until at least two years of age. Breast milk is considered the gold standard for infant nutrition. As a baby gets older, the composition of breast milk continues to change to meet his or her nutritional needs. There is no known age at which breast milk is considered to become nutritionally insignificant for a child. As long as breast feeding is continued, the cells, hormones, and antibodies in breast milk continue to bolster the baby's immune system. Research has indicated that the longer breast-feeding continues, and the more breast milk a baby drinks, the better his or her health may be.

Worldwide, babies are weaned on average between ages 2 and 4. In some cultures, breast-feeding continues until children are age 6 or 7. In other parts of the world, however, extended breast-feeding is less common.

In this example, fecal pellets were collected at the time of weaning. By mistake, one of the litters were weaned after 33 days (n=6), whereas normally pups were weaned on day 21 (n=6). There was a significant difference in blood glucose between both groups. Animals who weaned at a normal time had an aggressive diabetes development as compared to late weaning mice. However, after 10 weeks of age, no statistically significant differences were noticed in their blood glucose levels (Data not shown).

The bacterial community profiles of the T1D mouse model were investigated before, during, and after the onset of type 1 diabetes. The longitudinal collection of fecal pellets enabled insight into the earliest bacterial effects that may be associated with disease onset and progression. High-throughput sequencing of the 16S rRNA gene enabled robust bacterial profiling of fecal samples collected from 39 mice from an age of 19 days to more than six months of age. Analysis revealed significant longitudinal changes in fecal bacterial profiles as well as biomarker taxa that correlated with blood glucose measurements. Principal coordinates analysis demonstrated a consistent and distinct bacterial community structure stratified by age, indicating a distinct microbial gut ecology common to the progression of T1D that can be measured, described, and studied. Clustering of samples between age groups was found to be significant and explained 12% of the variation in the bacterial community.

Interestingly, sequencing of 16S rRNA gene revealed that late weaning litters have an enriched bacterial diversity as compared to the normal weaning group. This dynamic change in the bacterial community mirrors the observed lower glucose levels in the late-weaning population.

Example V

Prolonged Nursing

The humanized transgenic mice model of T1D, spontaneously develop diabetes. This mouse model mimics clinical human T1D, allowed us to carry out phase 1 controlled studies where diabetes development and gut microbiota were investigated after normal weaning (NW) and late weaning (LW) stages. The data revealed that the gut microbiota changes as weaning is delayed, and that disease progression correlates with these changes.

While not wishing to be bound by theory, it is now believed that to halt T1D or delay its progression, enrichment of regulatory T (Treg) cells secondary to increased diversity of gut microbiome may be induced with prolonged nursing.

The breeder's cages with larger litter sizes (8 pups) were separated in two groups. The breeder mice were allowed for a second time pregnancy, and after birth, the second litters were sacrificed and the first litters (late weaning group, LW) were allowed to stay with their mothers until day 45. Normal weaning (NW) group were separated at day 21. At day 60 and 150, mice from both groups (n=10-12) were sacrificed. Organs (Peyer's patches (PP), peri-pancreatic lymph nodes (PLN), pancreas (PN) and spleen) were harvested and lymphocytes isolated.

Figure 21A:
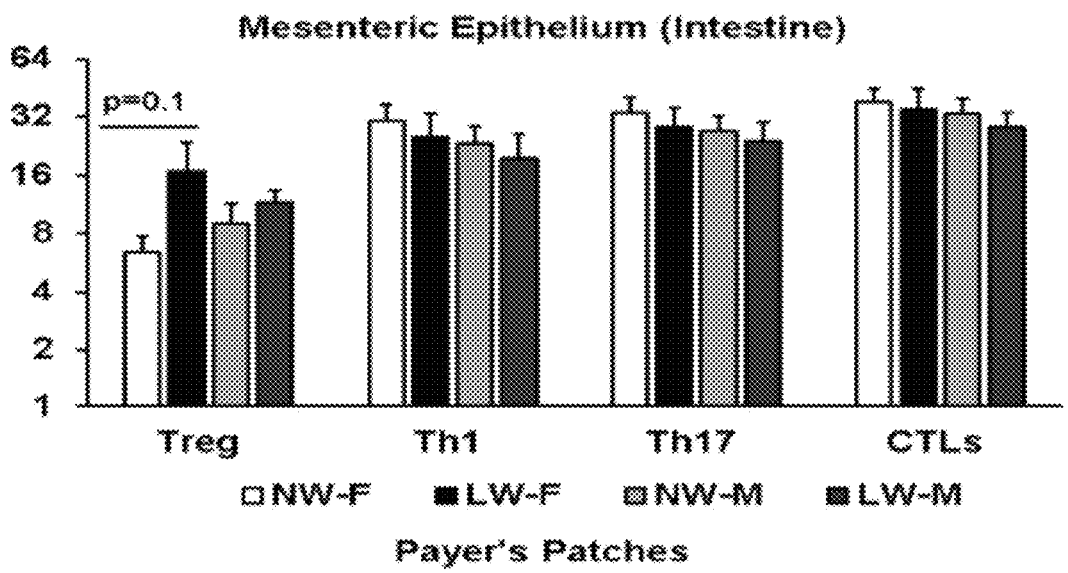
FIG. 21A: Immune profiling at 60 days, for mesenteric epithelium (intestine), showing the percentage of total T cells for: normal weaning female (NW-F), late weaning female (LW-F), normal weaning male (NW-M), and late weaning male (LW-M).
Figure 21B:
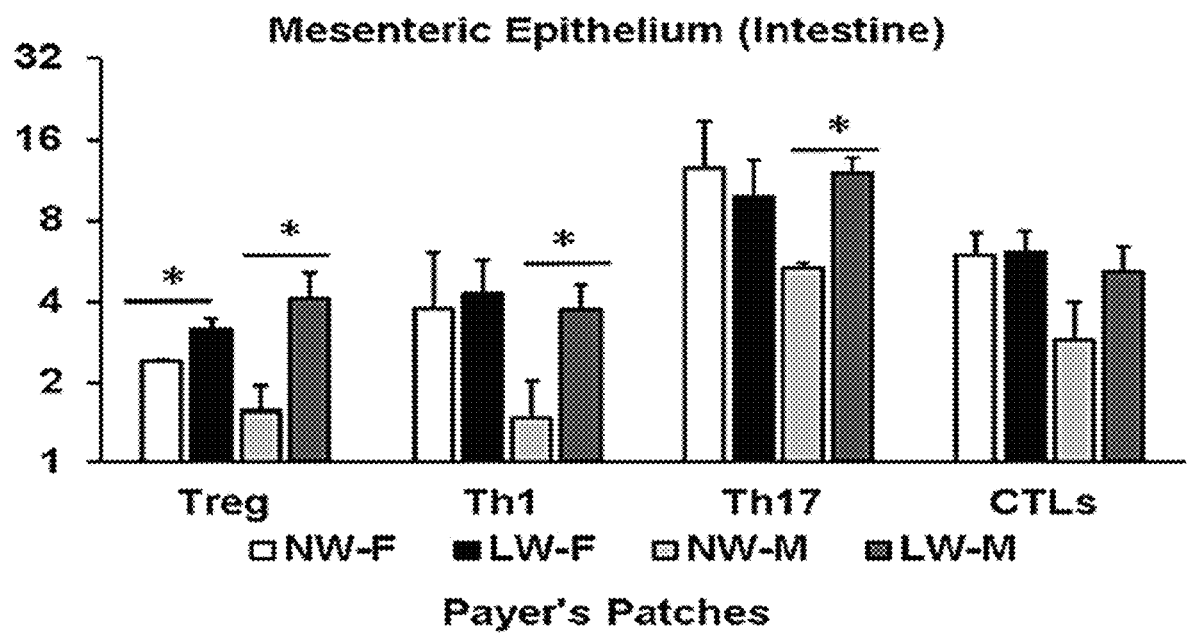
FIG. 21B: Immune profiling at 150 days, for mesenteric epithelium (intestine), showing the percentage of total T cells for: normal weaning female (NW-F), late weaning female (LW-F), normal weaning male (NW-M), and late weaning male (LW-M).

Immune Profiling:

A group of mice from LW and NW (n=10-12) were sacrificed on day $60^{th}$ and $150^{th}$. Organs (intestinal mesenteric epithelial, payer's patches, peri-pancreatic lymph nodes, pancreas and spleen) were harvested and lymphocytes were isolated. Flow cytometric analysis of the mesenteric epithelium (point of first interaction) revealed that Treg were significantly increased in LW group sacrificed at day $150^{th}$, the effect were more pronounce and significant (FIG. 21A, FIG. 21B, respectively).

Figure 21C:
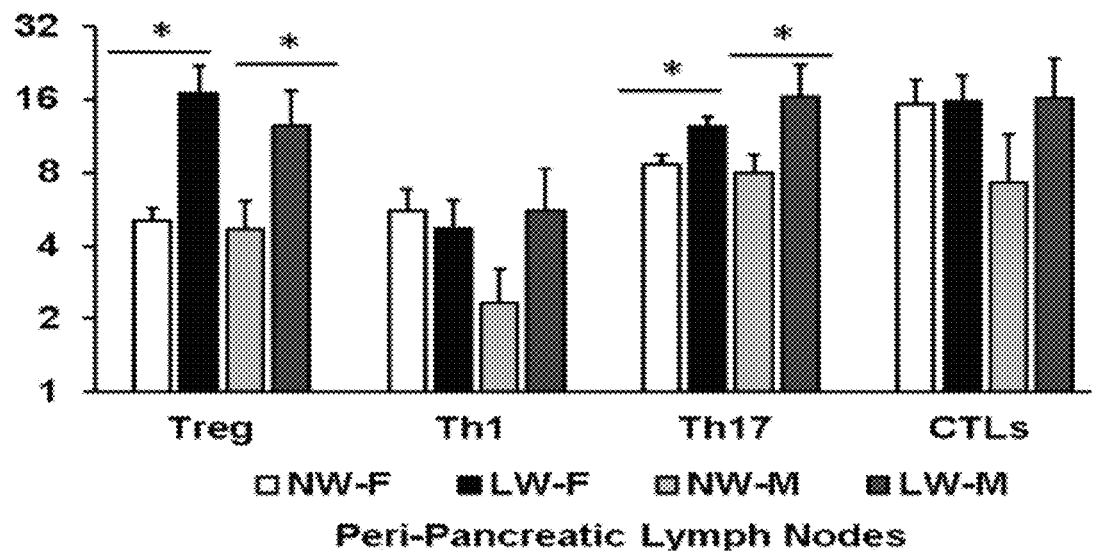
FIG. 21C: Immune profiling at 60 days, for Payer's Patch, the showing percentage of total T cells for: normal weaning female (NW-F), late weaning female (LW-F), normal weaning male (NW-M), and late weaning male (LW-M).
Figure 21D:
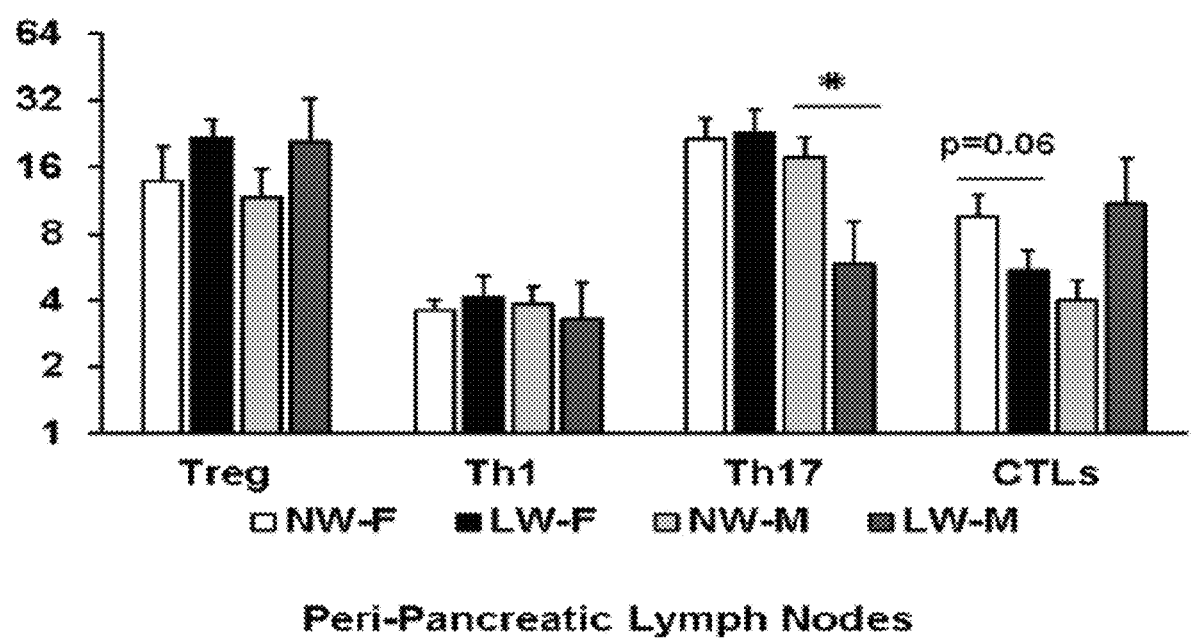
FIG. 21D: Immune profiling at 150 days, for Payer's Patch, the showing percentage of total T cells for: normal weaning female (NW-F), late weaning female (LW-F), normal weaning male (NW-M), and late weaning male (LW-M).

At mesenteric epithelium, the Th1 and Th17 were increased in the LW group especially on the group sacrificed on $150^{th}$ day. Flow cytometry of Payer's patches (first site of immune cells interaction/activation with gut antigen) revealed an increase in Treg cells in LW group and effect was significant in LW group sacrificed on $60^{th}$ day (FIG. 21C, FIG. 21D). Most interestingly LW group sacrificed on $60^{th}$ day, the Th17 population were significantly increased whereas; LW group sacrificed on $150^{th}$ day the Th17 population were significantly reduced in male.

Figure 21E:
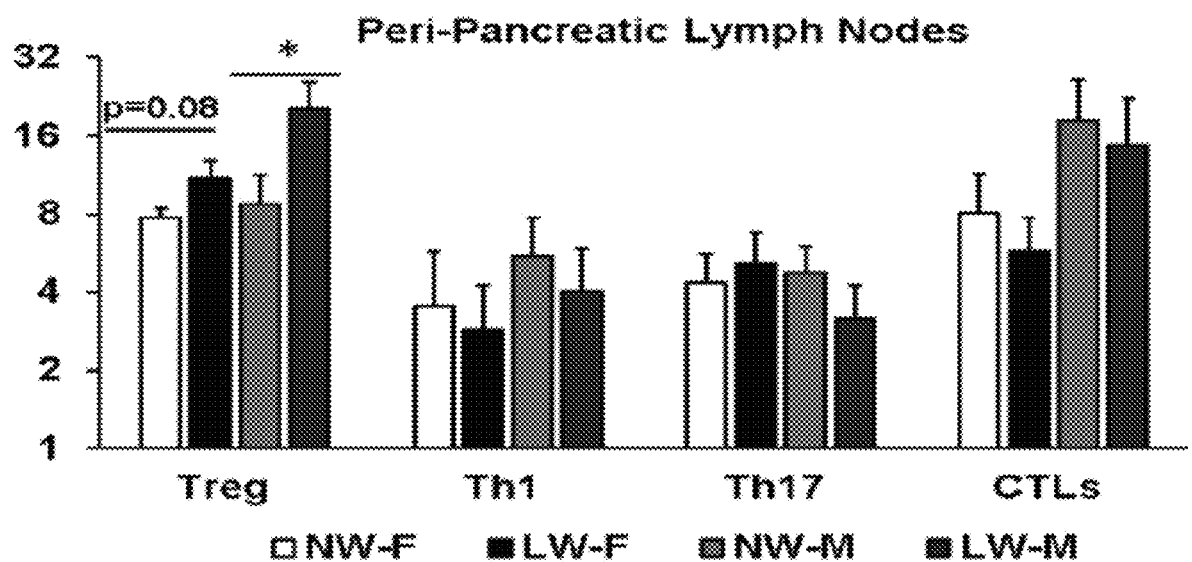
FIG. 21E: Immune profiling at 60 days, for peri-pancreatic lymph nodes, the showing percentage of total T cells for: normal weaning female (NW-F), late weaning female (LW-F), normal weaning male (NW-M), and late weaning male (LW-M).
Figure 21F:
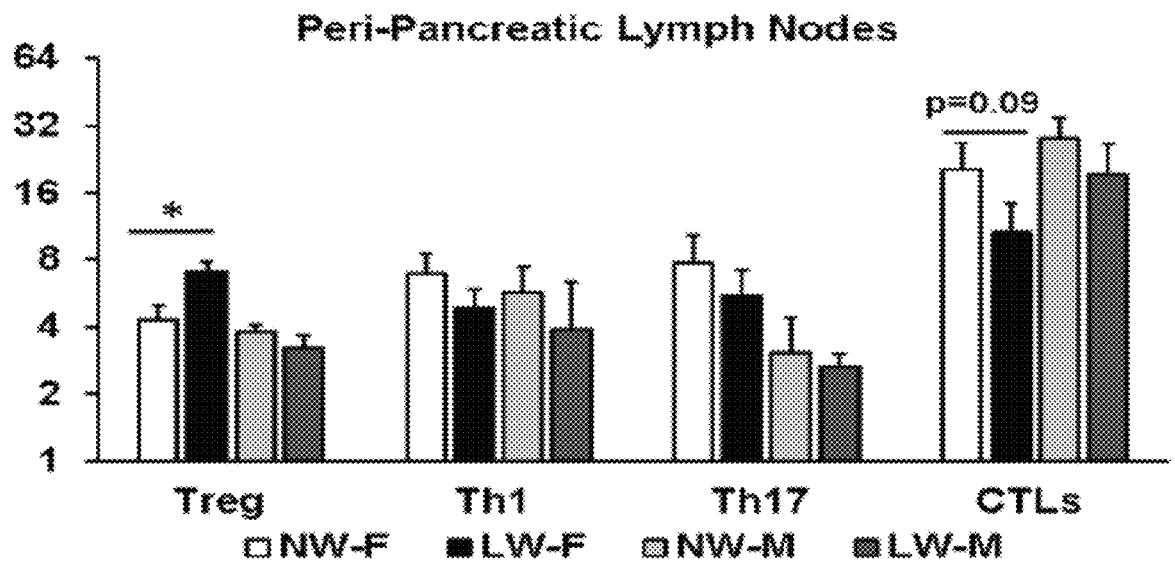
FIG. 21F Immune profiling at 150 days, for peri-pancreatic lymph nodes, the showing percentage of total T cells for: normal weaning female (NW-F), late weaning female (LW-F), normal weaning male (NW-M), and late weaning male (LW-M).

Flow cytometry analysis of peri-pancreatic lymph nodes (PLN) a point of islet antigen specific proliferation of T cells, revealed a significant increase in the Treg population which leads to reduction of CTLs in LW group (FIG. 21E, FIG. 21F).

Figure 21G:
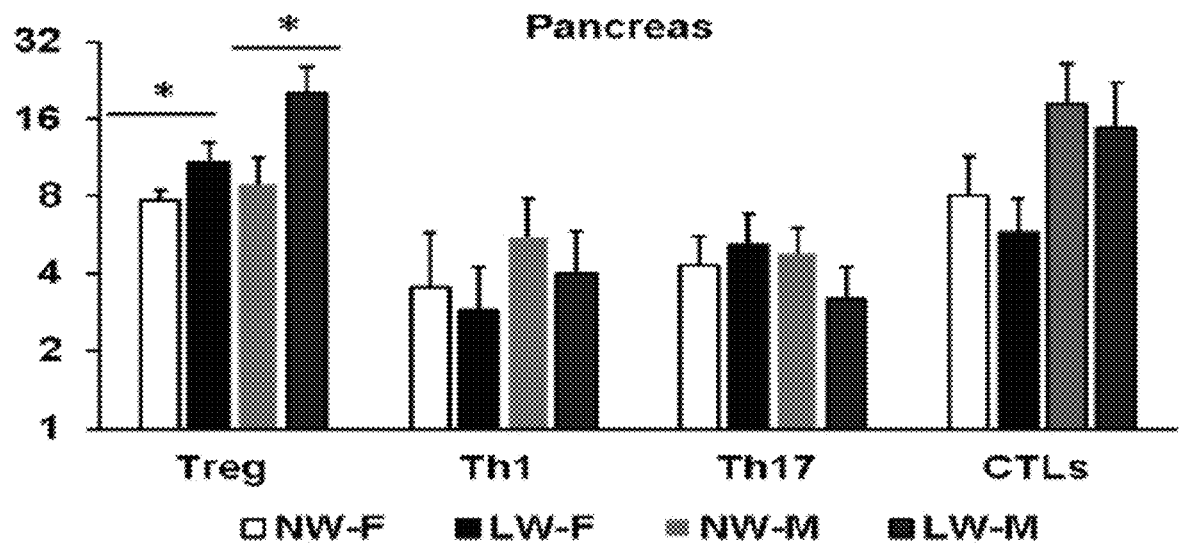
FIG. 21G: Immune profiling at 60 days, for pancreas, the showing percentage of total T cells for: normal weaning female (NW-F), late weaning female (LW-F), normal weaning male (NW-M), and late weaning male (LW-M).
Figure 21H:
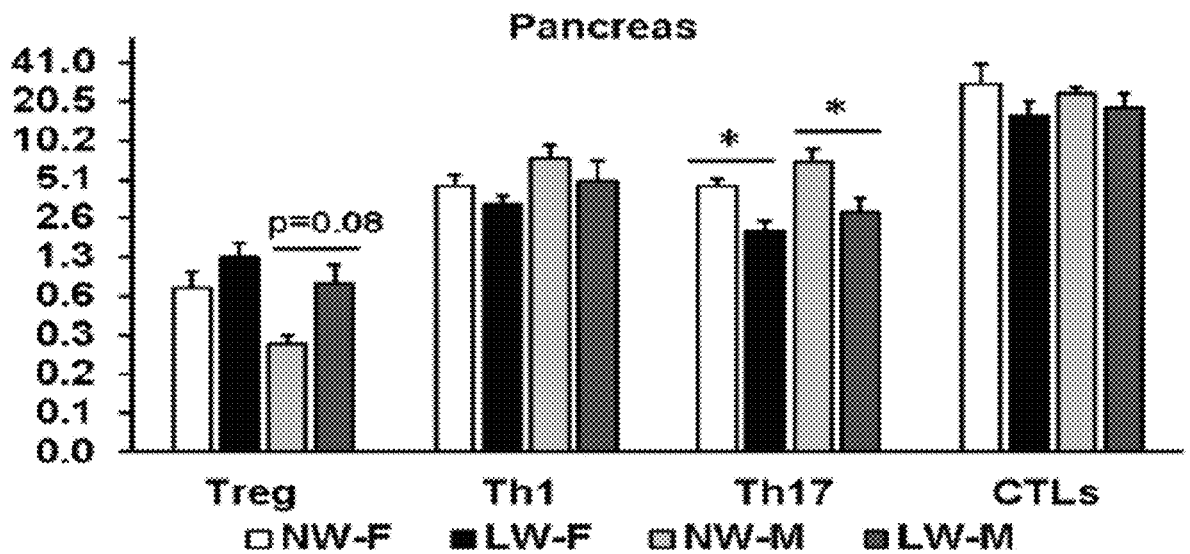
FIG. 21H: Immune profiling at 150 days, for pancreas, the showing percentage of total T cells for: normal weaning female (NW-F), late weaning female (LW-F), normal weaning male (NW-M), and late weaning male (LW-M).

Flow cytometry analysis of pancreas also revealed an increase in Treg population in LW group, which leads to reduce Th17 significantly in LW group (FIG. 21G, FIG. 21H).

Figure 21I:
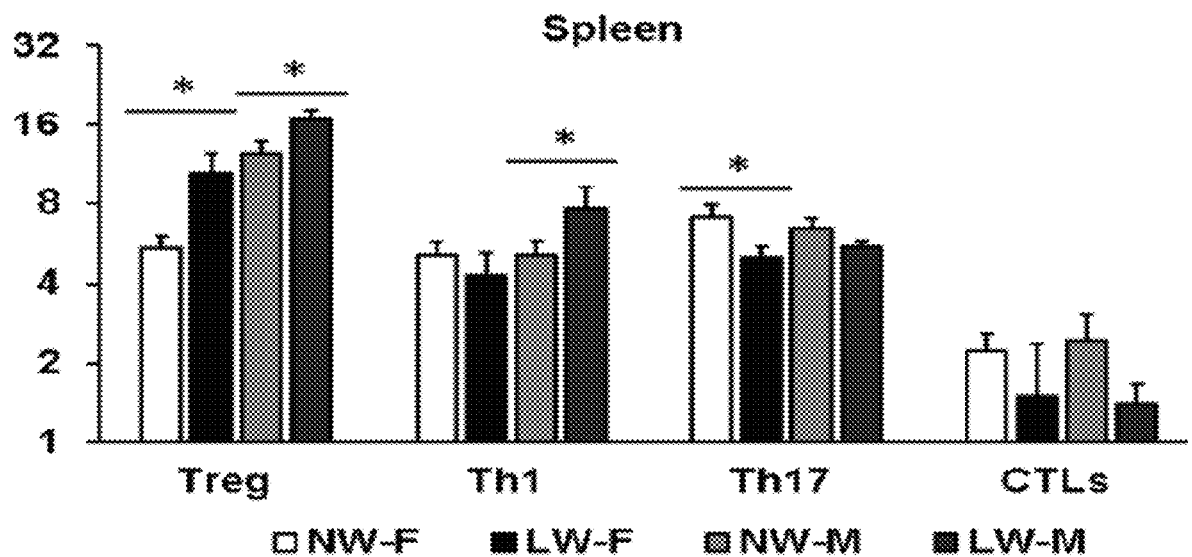
FIG. 21I: Immune profiling at 60 days, for spleen, the showing percentage of total T cells for: normal weaning female (NW-F), late weaning female (LW-F), normal weaning male (NW-M), and late weaning male (LW-M).
Figure 21J:
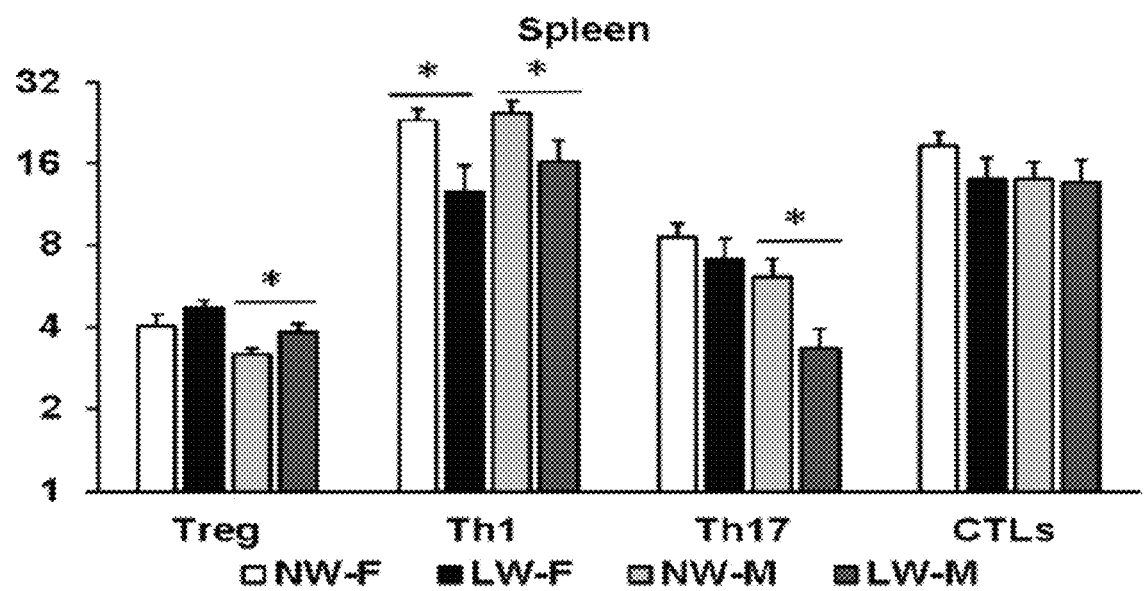
FIG. 21J: Immune profiling at 150 days, for spleen, the showing percentage of total T cells for: normal weaning female (NW-F), late weaning female (LW-F), normal weaning male (NW-M), and late weaning male (LW-M).

Flow cytometry analysis of spleen also revealed an increase in Treg population in LW group and consecutively leads to reduced Th1 and Th17 population in LW $60^{th}$ and $150^{th}$ day sacrificed group (FIG. 21I, FIG. 21J).

Flow cytometry data from harvested organs suggested that prolong nursing (late weaning) increase the immune tolerance in genetically susceptible mouse model of Type 1 Diabetes. The enrichment of Tregs may be because of more diverse microbiome and consecutively increase the immune tolerance which may had regulated the diabetogenic Th1 at pancreas and CTLs at peri-pancreatic lymph nodes and spleen. These data show prolong nursing (late weaning) may protect/delay the onset of T1D in genetically susceptible kids.

Increased in Immune Tolerance Improves the Islet Architecture.

Newborn mice littermates were divided into late weaning and normal weaning groups. Mice pancreases were fixed in 10% buffered formalin. Pancreatic sections were stained with hematoxylin/eosin (H&E) for histological identification and localization of islets and lymphocytic infiltrates. Late weaning groups, preserves the pancreatic islet architecture with fewer infiltration and having a significantly higher number of islet per H&E sections whereas, in normal weaning group, the islets were comparatively less in number, highly infiltrated, and smaller in size with partially disrupted islet architecture.

Figure 22:
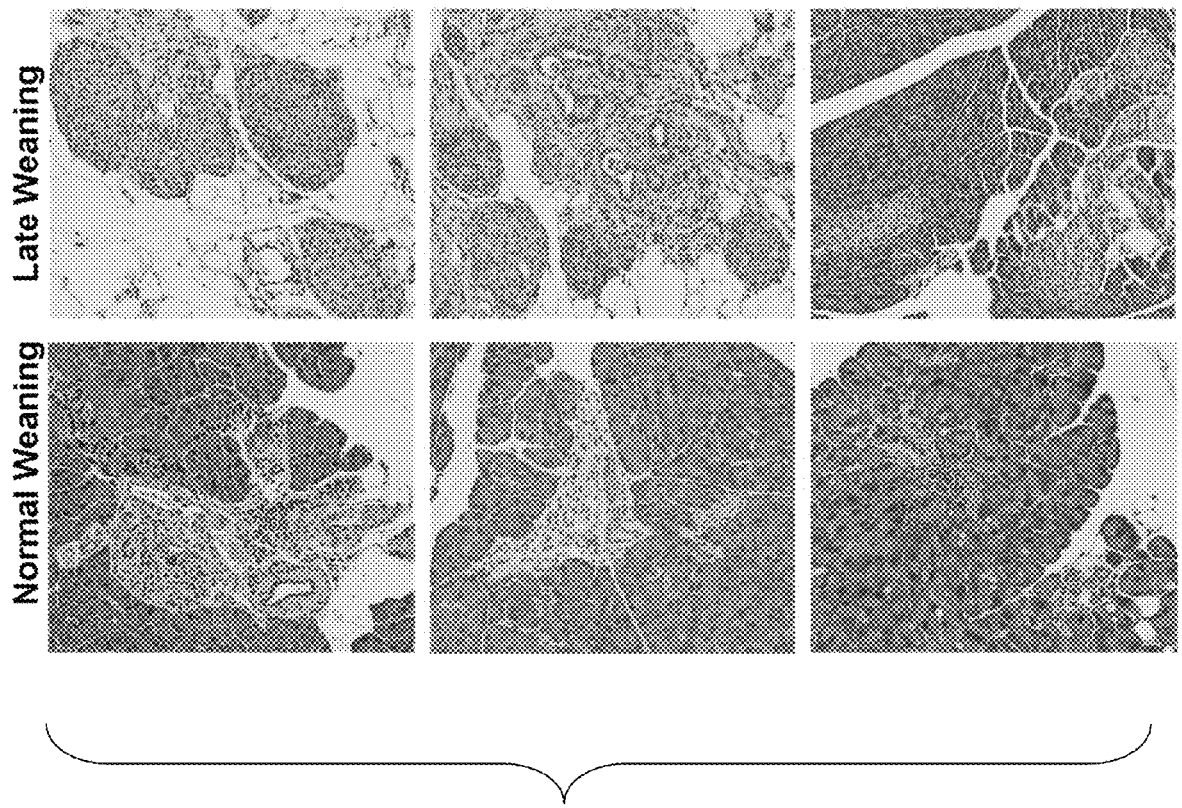
FIG. 22: A representative image of H&E staining of pancreas from humanized mice. Littermates were divided into late weaning (LW) and normal weaning (NW) groups. Mice pancreas were fixed in formalin block and sections were stained with H&E. Late weaning mice have more number of islets with intact islet architecture, whereas in normal weaning group, the islets were small with digested islet architecture.

FIG. 22 shows that late weaning enriches the Treg cells at all T cells recruitment and activation sites, and depletes the T cell population in pancreas, and is protective of islet architecture.

Example VI

Autoimmune Type 1 Diabetes (T1D) in Dogs

Autoimmune type 1 diabetes (T1D) is the most common form of diabetes in dogs, characterized by destruction of pancreatic β-cells leads to absolute insulin dependency. Some dogs develop a spontaneous immune mediated diabetes that resembles human Type 1 Diabetes (T1D). Dogs also develop other autoimmune disorders along with autoimmune diabetes like lymphocytic thyroiditis.

Dogs also develop a latent autoimmune diabetes of adult (LADA) form of T1D, characterized by gradual destruction of β-cells over a month or year and is not associated with obesity. Antibody pattern has been recognized and majority of these dogs are on absolute insulin deficient. Affected dog age is around seven years.

Genetic Predisposition of T1D has been well defined in human and similar HLA association has been reported in dogs. Dog leucocyte antigen (DLA) DQA1 alleles coding for arginine at position 55 (Arg55) in hypervariable region2, equivalent to HLA DQA1 (DQ8) Arg52 of human. (DLA) DQA1 haplotype has sequence similarity to human MHC allele associated with predisposition of type 1diabetes. Dogs having haplotype (DLA) DQA1 are three times more susceptible to develop diabetes than dogs with other haplotypes. The association between canine diabetes and MHC haplotype association strongly suggests that genetic predisposition and immune response have a role in pathophysiology of autoimmune type 1 diabetes in dogs.

Auto-antibodies against canine GAD65 and C-terminal region of canine islet antigen-2 has been reported in newly diagnosed dogs. There is a 96.8% homology between dog and human GAD65 sequence and is evolutionarily conserved across the species (FIG. 23A). Interspecies cross-reactivity has been well documented.

Insulitis in dogs are defined by initial peri-insular infiltration followed by intra-insular infiltration. Composition of diabetic dog islets comprises of 30% β-cells, 40% α-cells and 30% δ-cells which are different from healthy dogs islet cell architectural arrangements (78% β-cells, 11% α-cells and 11% δ-cells). Dog with longstanding autoimmune type 1 diabetes are devoid of β-cells.

Some reports revealed that canine autoimmune diabetes, pancreatic inflammation and regulation of gut immunity may be linked with disease pathogenesis.

Dog's autoimmune type 1 diabetes has a similarity to human type 1 diabetes in metabolic, genetic and pathophysiological characteristics. Therefore, it is now believed that the species that shares our lives closely develops autoimmune type 1 diabetes as like human.

The spontaneous humanized mouse model for T1D described herein is null for their own MHCII and express human MHCII (DQ8) in all antigen-presenting cells. The pancreatic islet β-cells of these mice express human Glutamic Acid Decarboxylase 65 isoform (GAD65). GAD65 antigen presentation activates T cells, which initiates the downstream events leading to spontaneously development of type 1 diabetes. This mouse model mimics human T1D at its best).

The mouse model of T1D resembles all characteristics of the human disease. These mice carry human diabetes susceptibility with a transgenic human MHCII gene known to occur in most T1D patients and spontaneously develop type 1 diabetes approximately 4-6 weeks of their age. The autoimmune attack to pancreatic β-cells progresses over time (chronicity) Animals initially develop anti-GAD65 antibodies while lymphocytic infiltration builds up in the peri- and intra-islet location. Initially glucose intolerance and later diabetes develops. Without intervention, animals die by developing the classic complications observed in humans with diabetes (i.e., retinopathy, nephropathy, and neuropathy).

As mention above, the (DLA) DQA1 haplotype of canine (dog) has sequence similarity to human MHC allele associated with predisposition of autoimmune type 1diabetes. There is a 96.8% homology between dog and human GAD65 sequence and is evolutionarily conserved across the species (FIG. 23A). Mounting of the canine immune cells against islet specific autoantigen GAD65 is same as like of human/now described T1D mice model. The clinical pathophysiology and progression of autoimmune diabetes in this mice model and canine (dogs) are same.

Figure 23B:
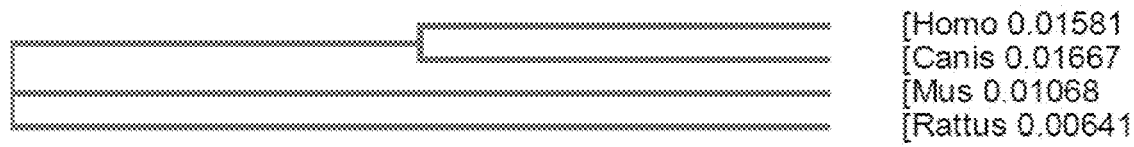
FIG. 23B: Phylogenic tree were created and Cladogram data revealed that Canine are more closure to human.
Figure 23A:
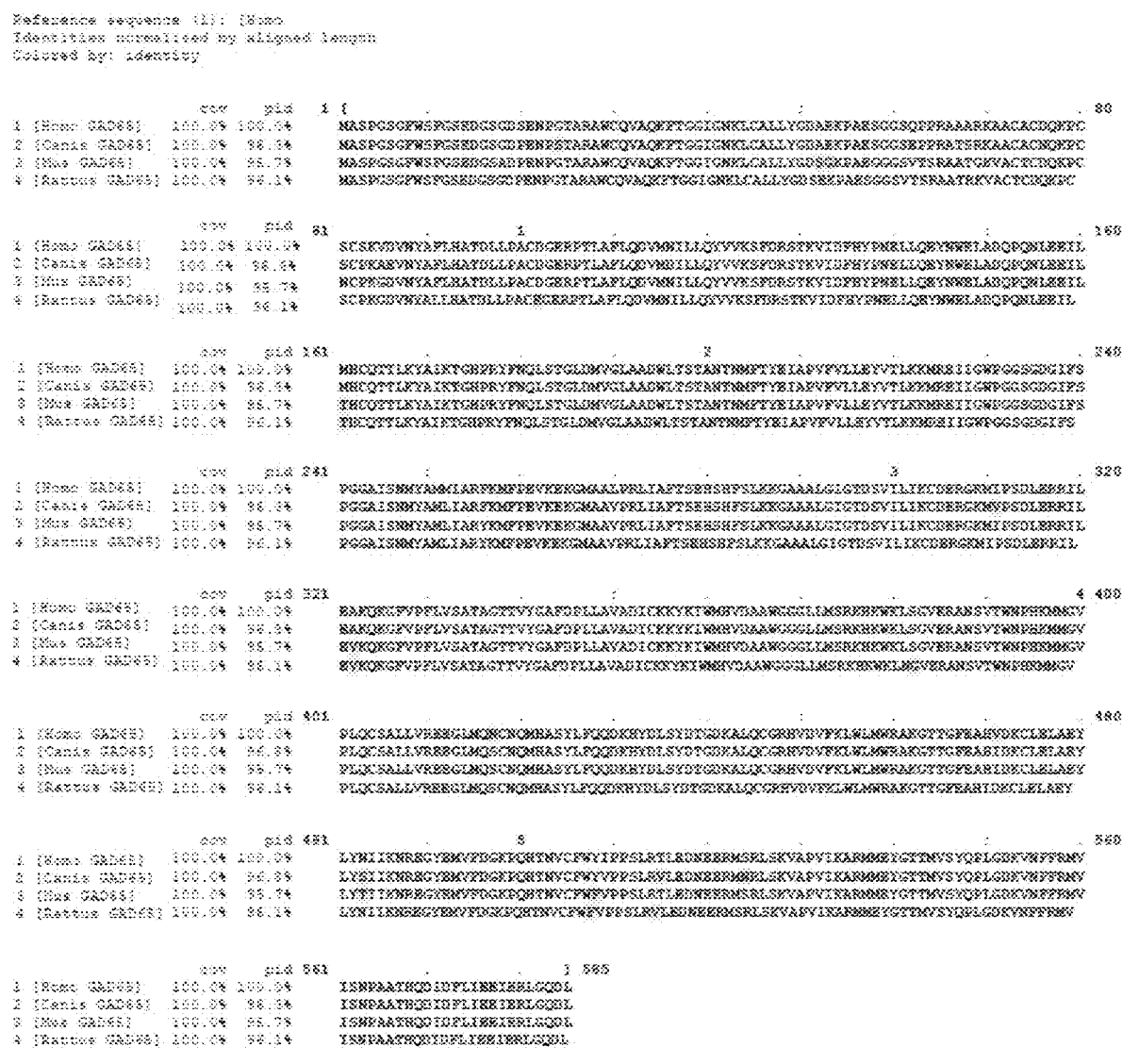

FIG. 23B shows the phylogenetic tree revealed there is a great similarity between canine and human GAD65 and they both have same phylogeny in case of GAD65.

Example VII

Methods of Using the Mouse Model

Method for identifying a compound useful in the treatment and/or prevention of type 1 diabetes (T1D) are also within the contemplated scope of the inventions. For example, one method comprises the steps of: (a) administering a test compound to a mouse model of claim 1 or a cell from the mouse model, and (b) determining the effect of the test compound on the initiation, maintenance, or progression of at least one parameter in the mouse model; thereby identifying a compound that treats or inhibits T1D and/or complications of T1D.

The at least one parameter can be one or more of: diabetic retinopathy; diabetic nephropathy; focal segmental mesangial matrix increase and hyaline deposit in glomerular arterioles of the kidneys; lymphocytic infiltration of islets of Langerhans in the pancreas; proliferation of acellular capillaries in the retina; compromised β-cell neogenesis and/or proliferation.

In certain embodiments the cells are beta cells, kidney cells, islets of Langerhans, pancreatic cells, retinal cells Yet another aspect of the invention provides the use of the genetically modified non-human mammal according to the invention for screening or validation of an agent useful as a medicament for treatment of type 1 diabetes (T1D) and/or complications of T1D.

In one aspect, the invention provides a method of validating an agent, comprising the steps of: a) providing a mouse model according to the present invention, b) contacting the mouse model with an agent for validation, and, c) determining whether the mouse model is responsive to the agent after the contact.

Another aspect of the invention provides use of the mouse model according to the invention for screening and/or validation of an agent useful as a medicament for treatment and/or prevention of T1D. In particular, the screening and/or validation process may combine biochemical, electrophysiological, histological and behavioral evaluations, including, but not limited to effects on diabetic nephropathy; focal segmental mesangial matrix increase and hyaline deposit in glomerular arterioles of the kidneys; lymphocytic infiltration of islets of Langerhans in the pancreas; proliferation of acellular capillaries in the retina. compromised β-cell neogenesis and/or proliferation.

Another aspect of the invention provides a method of validating an agent comprising the steps of: a) providing a mouse model as described above, b) contacting the mouse with an agent for validation, c) determining whether the non-human mammal is responsive to the agent after the contact.

One or more aspects of the present invention may each be combined with any of the other aspects. These and other aspects of the invention will be apparent from and elucidated with reference to the embodiments described hereinafter.

In particular, the use according to the invention may involve determination of pharmacokinetics, pharmacodynamics, ADME (absorptioin, distribution, metabolism and excretion), toxicity and possible side effects of single dosing of the agent. In addition the use may involve analysis at different time points after dosing in order to determine the time-dependency of therapeutic effects.

Also, the use according to the invention may involve repeated injection of the agent for instance in order to optimize dosage regimen, including dosage size and administration intervals and/or to evaluate possible side effects, including immunological side effects, of repeated treatment. The use according to the invention may also involve long-term studies to evaluate the full therapeutic potential of administration of the agent.

Methods of Screening

The invention provides methods for identifying compounds, e.g., small organic or inorganic molecules (e.g., those with a molecular weight of less than 1,000 Da), oligopeptides, oligonucleotides, or carbohydrates, capable of treating T1D and/or complications of T1D.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules. In addition, a number of libraries, including small molecule libraries, are commercially available.

In some embodiments, test compounds and libraries thereof can be obtained by systematically altering the structure of a first test compound. For example, in one embodiment, a general library of small molecules is screened, e.g., using the methods described herein, to select a first test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In certain embodiments, screening methods of the present invention utilize libraries of test compounds. As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound).

Certain embodiments of the transgenic mice, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A transgenic C57BL/6-BTBR mouse whose genome comprises:
   a) a replacement of an endogenous major histocompatibility complex (MHC) II gene with a nucleic acid sequence encoding a human leukocyte antigen (HLA)-DQ8 protein; and
   b) a nucleic acid sequence encoding human glutamic acid decarboxylase 65 (hGAD65) operably linked to a rat insulin promoter,
   wherein the transgenic mouse has a deficiency in beta-cell neogenesis and exhibits symptoms of type 1 diabetes (T1D) by 4-6 weeks of age.

2. The transgenic mouse of claim 1, wherein the symptoms of T1 D include diabetic retinopathy.

3. The transgenic mouse of claim 1, wherein the symptoms of T1D include diabetic nephropathy.

4. The transgenic mouse of claim 1, wherein the symptoms of T1D include focal segmental mesangial matrix increase and hyaline deposit in glomerular arterioles of the kidneys.

5. The transgenic mouse of claim 1, wherein the symptoms of T1D include lymphocytic infiltration of islets of Langerhans in the pancreas.

6. The transgenic mouse of claim 1, wherein the symptoms include proliferation of acellular capillaries in the retina.

7. A method for identifying a compound that treats T1 D, the method comprising:
   a) administering a compound to the transgenic mouse of claim 1, wherein the transgenic mouse exhibits symptoms of T1 D, and
   b) determining whether the compound decreases the symptoms of T1 D, thereby identifying a compound that treats T1 D.

8. The method of claim 7, wherein the symptoms of T1D include focal segmental mesangial matrix increase and hyaline deposit in glomerular arterioles of the kidneys.

9. A method of delaying onset of symptoms of T1 D, the method comprising:
   weaning the transgenic mouse of claim 1 after at least 45 days such that the onset of symptoms of T1D is delayed as compared to weaning the mouse by 21 days.

10. A kit comprising a male transgenic mouse and a female transgenic mouse of claim 1.

11. The transgenic mouse of claim 1, wherein the hGAD65 is expressed in beta-cells of the mouse.

* * * * *

SEQUENCE LISTING

```
<160> NUMBER OF SEQ ID NOS: 4

<210> SEQ ID NO 1
<211> LENGTH: 585
<212> TYPE: PRT
<213> ORGANISM: Homo sapiens

<400> SEQUENCE: 1

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
```

-continued

```
            130                 135                 140
Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
                180                 185                 190

Ala Asp Trp Leu Thr Ser Thr Ala Asn Thr Asn Met Phe Thr Tyr Glu
                195                 200                 205

Ile Ala Pro Val Phe Val Leu Leu Glu Tyr Val Thr Leu Lys Lys Met
                210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
                260                 265                 270

Leu Ile Ala Phe Thr Ser Glu His Ser His Phe Ser Leu Lys Lys Gly
                275                 280                 285

Ala Ala Ala Leu Gly Ile Gly Thr Asp Ser Val Ile Leu Ile Lys Cys
                290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
                355                 360                 365

Gly Gly Leu Leu Met Ser Arg Lys His Lys Trp Lys Leu Ser Gly Val
                370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
                435                 440                 445

His Val Asp Val Phe Lys Leu Trp Leu Met Trp Arg Ala Lys Gly Thr
                450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
                500                 505                 510

Leu Arg Thr Leu Glu Asp Asn Glu Glu Arg Met Ser Arg Leu Ser Lys
                515                 520                 525

Val Ala Pro Val Ile Lys Ala Arg Met Met Glu Tyr Gly Thr Thr Met
                530                 535                 540

Val Ser Tyr Gln Pro Leu Gly Asp Lys Val Asn Phe Phe Arg Met Val
545                 550                 555                 560
```

Ile Ser Asn Pro Ala Ala Thr His Gln Asp Ile Asp Phe Leu Ile Glu
            565                 570                 575

Glu Ile Glu Arg Leu Gly Gln Asp Leu
            580                 585

<210> SEQ ID NO 2
<211> LENGTH: 585
<212> TYPE: PRT
<213> ORGANISM: Canis sp.

<400> SEQUENCE: 2

Met Ala Ser Pro Gly Ser Gly Phe Trp Ser Phe Gly Ser Glu Asp Gly
1               5                   10                  15

Ser Gly Asp Pro Glu Asn Pro Ser Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Glu Pro Pro
        50                  55                  60

Arg Ala Thr Ser Arg Lys Ala Ala Cys Ala Cys Asn Gln Lys Pro Cys
65                  70                  75                  80

Ser Cys Pro Lys Ala Glu Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asp Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Leu Ile Ala Arg Phe
                245                 250                 255

Lys Met Phe Pro Glu Val Lys Glu Lys Gly Met Ala Ala Val Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Val Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp

```
                340                 345                 350
Ile Cys Lys Lys Tyr Lys Ile Trp Met His Val Asp Ala Ala Trp Gly
                355                 360                 365

Gly Gly Leu Leu Met Ser Arg Lys His Lys Trp Lys Leu Ser Gly Val
        370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Ser Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Ile Asp Lys Cys Leu Glu Leu Ala Glu Tyr
465                 470                 475                 480

Leu Tyr Ser Ile Ile Lys Asn Arg Glu Gly Tyr Glu Met Val Phe Asp
                485                 490                 495

Gly Lys Pro Gln His Thr Asn Val Cys Phe Trp Tyr Val Pro Pro Ser
            500                 505                 510

Leu Arg Val Leu Glu Asp Asn Glu Glu Arg Met Asn Arg Leu Ser Lys
        515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 3
<211> LENGTH: 585
<212> TYPE: PRT
<213> ORGANISM: Mus sp.

<400> SEQUENCE: 3

Met Ala Ser Pro Gly Ser Gly Phe Trp Ser Phe Gly Ser Glu Asp Gly
1               5                   10                  15

Ser Ala Asp Pro Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ser Gly Lys Pro Ala Glu Gly Gly Ser Val Thr Ser
    50                  55                  60

Arg Ala Ala Thr Gly Lys Val Ala Cys Thr Cys Asp Gln Lys Pro Cys
65                  70                  75                  80

Asn Cys Pro Lys Gly Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
    115                 120                 125
```

```
Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Thr His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Leu Ile Ala Arg Tyr
                245                 250                 255

Lys Met Phe Pro Glu Val Lys Glu Lys Gly Met Ala Ala Val Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Leu Glu Arg Arg Ile Leu
305                 310                 315                 320

Glu Val Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Ser Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
450                 455                 460

Thr Gly Phe Glu Ala His Ile Asp Lys Cys Leu Glu Leu Ala Glu Tyr
465                 470                 475                 480

Leu Tyr Thr Ile Ile Lys Asn Arg Glu Gly Tyr Glu Met Val Phe Asp
                485                 490                 495

Gly Lys Pro Gln His Thr Asn Val Cys Phe Trp Phe Val Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
530                 535                 540

Val Ser Tyr Gln Pro Leu Gly Asp Lys Val Asn Phe Phe Arg Met Val
```

```
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
            580                 585

<210> SEQ ID NO 4
<211> LENGTH: 585
<212> TYPE: PRT
<213> ORGANISM: Rattus sp.

<400> SEQUENCE: 4

Met Ala Ser Pro Gly Ser Gly Phe Trp Ser Phe Gly Ser Glu Asp Gly
1               5                   10                  15

Ser Gly Asp Pro Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ser Glu Lys Pro Ala Glu Ser Gly Gly Ser Val Thr Ser
    50                  55                  60

Arg Ala Ala Thr Arg Lys Val Ala Cys Thr Cys Asp Gln Lys Pro Cys
65                  70                  75                  80

Ser Cys Pro Lys Gly Asp Val Asn Tyr Ala Leu Leu His Ala Thr Asp
                85                  90                  95

Leu Leu Pro Ala Cys Glu Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Thr His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Leu Ile Ala Arg Tyr
                245                 250                 255

Lys Met Phe Pro Glu Val Lys Glu Lys Gly Met Ala Ala Val Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Val Lys Gln Lys Gly Phe Val Pro Phe Leu Val Ser Ala Thr Ala
                325                 330                 335
```

-continued

```
Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Asn Gly Val
        370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Ser Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
            450                 455                 460

Thr Gly Phe Glu Ala His Ile Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Phe Val Pro Pro Ser
                500                 505                 510

Leu Arg Val Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
            530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585
```